United States Patent [19]

Mori et al.

[11] Patent Number: 4,820,836

[45] Date of Patent: Apr. 11, 1989

[54] PROSTACYCLIN (PGI$_2$) ANALOGUES

[75] Inventors: Sachio Mori; Hikozo Iwakura; Shozo Takechi, all of Hyogo, Japan

[73] Assignee: Shionogi & Co., Ltd., Osaka, Japan

[21] Appl. No.: 25,807

[22] Filed: Mar. 13, 1987

[30] Foreign Application Priority Data

Mar. 31, 1986 [JP] Japan ................................. 61-74932

[51] Int. Cl.$^4$ ............................................. C07D 209/52
[52] U.S. Cl. ........................................ 548/512; 548/468
[58] Field of Search ................................ 548/512, 468

[56] References Cited

U.S. PATENT DOCUMENTS

| 4,371,542 | 2/1983 | Beck | 514/412 |
| 4,487,960 | 12/1984 | Lin | 560/256 |
| 4,588,823 | 5/1986 | Aristoff | 549/422 |

FOREIGN PATENT DOCUMENTS 77209  4/1983  European Pat. Off. ............ 514/412

Primary Examiner—Robert Gerstl
Attorney, Agent, or Firm—Wenderoth, Lind & Ponack

[57] ABSTRACT

Prostacyclin (PGI$_2$) analogues represented by the formula:

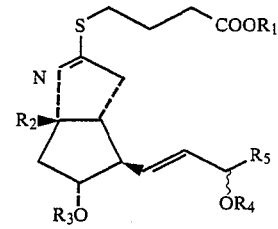

wherein $R_1$ is hydrogen or lower alkyl; $R_2$ is alkynyl; $R_3$ and $R_4$ each is hydrogen; $R_5$ is straight or branched alkyl which may be substituted with heterocycle, straight or branched alkynyl, or cycloalkyl; the wavy line indicates R- or S-configuration, or their mixture; or a salt thereof being used as antithrombotic and antiulcer drugs.

20 Claims, No Drawings

PROSTACYCLIN (PGI₂) ANALOGUES

BACKGROUND OF THE INVENTION

1. Field of the Invention

This invention relates to prostacyclin (PGI$_2$) analogues which are used as antithromboic and antiulcer drugs in the field of medicines. In more detail, this invention relates to the compounds represented by the general formula (I) or their salts, which have prostacyclin (PGI$_2$)-like inhibitory activity against platelet agglutination and antiulcer activity.

2. General Formula

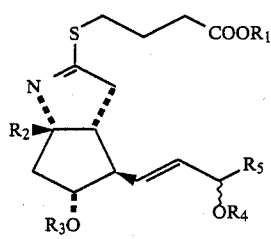

where R$_1$ is hydrogen or lower alkyl; R$_2$ is lower alkyl, lower alkenyl, lower alkynyl, lower aralkynyl, lower alkyloxy, arylthio, or cyano; R$_3$ and R$_4$ each is hydrogen or hydroxy-protecting group; R$_5$ is straight or branched alkyl which may be substituted with heterocycle, straight or branched alkynyl, or cycloalkyl; the wavy line indicates R- or S-configuration, or their mixture:

PGI$_2$ is produced mainly in the vascular cell or leukocytes as follows. Phospholipase A$_2$ activated by chemical or physical stimulation of the vascular cell, accelerates release of arachidonic acid which is converted into PGI$_2$ by the action of cyclooxygenase and PGI$_2$ synthetase, PGI$_2$ has a potent inhibitory activity against platelet agglutination and vasodilative activity and is used as an antiplatelet agent for patients who have been treated with artificial dialysis or pump-oxygenator. As the other clinical applications of PGI$_2$, the applications to thrombotic diseases such as peripheral circulatory insufficiency, e.g., vibration disease, collagen diseases, Buerger disease, and arteriosclerosis obliterans; ischemic heart diseases, e.g., angina pectoris and myocardial infarction; and disturbance of cerebral circulation, e.g., cerebral thrombosis, cerebral embolis and cerebral infarction, are expected. However, PGI$_2$ also has several problems; for example, it is chemically unstable and has hypotensive activity, which is undesirable for antithromboic drugs. Therefore, it has been desired that the chemically stable PGI$_2$ analogues having more potent platelet agglutination inhibitory activity and higher selectivity of the action are developed.

The present inventors have prepared the prostacyclin analogues represented by the general formula (I), and found that these novel compounds have a potent activity as PGI$_2$ receptor agonists and are chemically stable. The present invention is based upon these findings.

DESCRIPTION OF THE PRIOR ART

Thrombosis is induced with occurrence of hemangio-endothelium injury or inflammation, alteration of blood flow volume, or raise of blood coagulation ability. A white thrombus, often induced by Buerger disease, arteriosclerosis obliteran and so on, is also known as conglutination thrombus which is generated by gathering of platelets, leukocytes, fibrin, or erythrocytes on the injury, ulcer or rough surface of the intima, obliterates or strangulates the lumen, readily adheres to the wall of artery and causes the organic diseases. In the vein, alteration of the blood flow volume and congestion of the blood flow which are provoked by many causes generate intravascular cagulation to form red thrombus. Usually, the red thrombus is adhered to the surface of the white thrombus to gradually induce the obliteration extending over a wide area. When the main artery is rapidly blocked by thrombus, a strong disturbance of peripheral circulation is caused accompanied by the necrosis of tissue. Thus, it is thought that the agglutination activity of platelet is an important factor in vascular diseases such as thrombosis and arterial sclerosis. Therefore, it has been recognized that the administration of antithromboic drugs, especially the drugs which possess inhibitory activity against platelet agglutination will be efficacious for the prevention or treatment of those vascular diseases. In addition to the conventional antithrombic drugs such as heparin and coumarin compounds, a certain type of prostaglandins (hereinafter abbreviated to PG) are known to have a potent inhibitory activity against platelet agglutination. From these facts, prostaglandin derivatives have attached public attention as antithromboic drugs. For example, PG analogues which act as agonists of the receptor of PE E$_1$ and I$_2$, having potent inhibitory activity against platelet agglutination and vasodilating activity, have been developed as well as, inhibitors which inhibit synthesis of thromboxane A$_2$ adversely acting to PGI$_2$. As the PGI$_2$ analogues, Hoe-892 [B. A. Schölkens et.al., Prostaglandins Leukotrienes. Med., 10, 231–256, (1983)], OP-41483 [P. G. Adaikan et.al., Prostaglandins Leukotrienes. Med., 10, 53~64, (1983)], ZK-36374 [J. J. F. Belch et.al., Prostaglandins, 28, 67~77, (1984)] Nitrilo-PGI$_2$ [R. R. Gorman et.al., Prostaglandins, 19, 2~14, (1980)], and 9-substituted carbacyclin analogue [P. A. Aristoff et.al., J. Org. Chem., 48, 5341~5348, (1983)] can be exemplified.

SUMMARY

Prostacyclin (PG I$_2$) analogues represented by the formula:

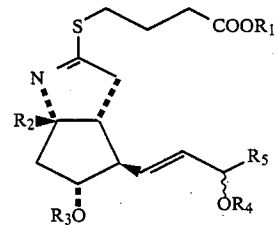

wherein R$_1$ is hydrogen or lower alkyl; R$_2$ is lower alkyl, lower alkenyl, lower alkynyl, lower aralkynyl, lower alkyloxy, arythio, or cyano; R$_3$ and R$_4$ each is hydrogen or hydroxy-protecting group; R$_5$ is straight or branched alkyl which may be substituted with heterocycle, straight or branched alkynyl, or cycloalkyl; the wavy line indicates R- or S-configuration, or their mixture; or a salt thereof. Said compounds are used as antithrombotic and antiulcer drugs.

DESCRIPTION OF THE PREFERRED EMBODIMENTS

The following definitions are given for various terms used throughout this specification.

The term "lower alkyl" refers to a straight or branched alkyl of $C_1$–$C_6$, e.g., methyl, ethyl, n-propyl, isopropyl, butyl, tert-butyl, pentyl and the like. The term "alkyl" refers to a straight or branched alkyl of $C_1$–$C_8$, e.g., methyl, ethyl, propyl, isopropyl, butyl, tert-butyl, pentyl, isopentyl, neopentyl, 1-methylpentyl, 1,1-dimethylpentyl, hexyl, heptyl, octyl and the like. The term "lower alkenyl" refers to a group having one or more double bonds in the above alkyl chain, e.g., ethenyl, 1-propenyl, 2-propenyl, butenyl, isobutenyl, pentenyl, isopentenyl, and the like. The term "lower alkynyl" refers to a group having one or more triple bonds in the above lower alkyl, e.g., ethynyl, 1-propynyl, 1-butynyl, 1,3-butadiynyl, 1-pentynyl, 1,3-pentadiynyl, 1-hexynyl, 1,3-hexadiynyl and the like. The term "alkynyl" refers to a group having one or more triple bonds in the above alkyl, e.g., ethynyl, 1-propynyl, 2-propynyl, 1-butynyl, 2-butynyl, 1-methyl-3-butynyl, 1,1-dimethyl-3-butynyl, 1,3-butadiynyl, 1-pentynyl, 2-pentynyl, 3-pentynyl, 4-pentynyl, 1-methyl-3-pentynyl, 1,1-dimethyl-3-pentynyl, 1-hexynyl, 3-hexynyl, 1-methyl-3-hexynyl, 1,1-dimethylhexynyl, and the like. The term "cycloalkyl" refers to $C_3$–$C_8$ cycloalkyl, e.g, cyclopropyl, cyclopentyl, cyclohexyl, cycloheptyl, cyclooctyl, and the like. The term "aryl" refers to substituted or unsubstituted phenyl, naphthyl, polycyclic aromatic hydrocarbon, and the like. Substituents on the aromatic ring include those such as alkyl, alkoxy, nitro or the like. The term "lower alkyloxy" refers to $C_1$–$C_6$ alkyloxy, e.g., methoxy, ethoxy, propoxy, isopropoxy, butoxy, isobutoxy, tert-butoxy, pentoxy, isopentoxy, and the like. The term "heterocycle" refers to nitrogen-, oxygen-, or sulfur-containing 5-membered one, e.g., 2-pyrrolyl, 3-pyrrolyl, 2-thienyl, 3-thienyl, 2-furyl, 3-furyl, and the like. The term "lower aralkynyl" refers to a group corresponding to the above lower alkynyl substituted with an aryl at optional position, e.g., phenylethynyl, 2-naphthylethynyl, 3-phenyl-1-propynyl, and the like. The term "arylthio" refers to phenylthio, naphtylthio, and the like. The hydroxy-protecting group, e.g., tetrahydropyranyl, trimethylsilyl, dimethyl-tert-butylsilyl, diphenyl-tert-butylsilyl, and the like.

The salts of the compound represented by the general formula (I) may include, for example, salts with alkaline metal such as lithium, sodium, and potassium, salts with alkaline earth metal such as calcium, ammonium salts, salts with organic base such as triethylamine, N-methylmorpholine and pyridine, and salts with amino acid such as glycine, valine and alanine.

In the above definition, preferable $R_1$ is hydrogen or lower alkyl; and more preferable $R_1$ is hydrogen, methyl, or ethyl. Preferable $R_2$ is lower alkyl, lower alkenyl, lower alkynyl, lower aralkynyl, lower alkyloxy, or arylthio; and more preferable $R_2$ is methyl, ethyl, ethenyl, ethynyl, 1-propynyl, 1,3-butadiynyl, phenylethynyl, methoxy, or phenylthio. Perferable $R_3$ and $R_4$ each is hydrogen or hydroxy-protecting group; and more perferable $R_3$ and $R_4$ each is hydrogen, diphenyl-tert-butylsilyl, or dimethyl-tert-butylsilyl. Preferable $R_5$ is straight or branched alkyl which may be substituted with heterocycle, straight or branched alkynyl, or cycloalkyl; and more perferable $R_5$ is pentyl, 1-methylpentyl, 1,1-dimethylpentyl, 2-(2-furyl)ethyl, 1-methyl-3-pentynyl, cyclopentyl, cyclohexyl.

Illustrative of the compounds (I) of present invention are as follows:

4-[7-hydroxy-6-(3-hydroxy-1-octenyl)-1-methoxy-2-azabicyclo[3.3.0]oct-2-en-3-yl]thiobutanoic acid, 4-[7-hydroxy-6-(3-hydroxy-1-octenyl)-1-phenylthio-2-azabicyclo[3.3.0]oct-2-en-3-yl]thiobutanoic acid, 4-[7-hydroxy-6-(3-hydroxy-1-octenyl)-1-methyl-2-azabicyclo[3.3.0]oct-2-en-3-yl]thiobutanoic acid, 4-[1-ethyl-7-hydroxy-6-(3-hydroxy-1-octenyl)-2-azabicyclo[3.3.0]oct-2-en-3-yl]thiobutanoic acid, 4-[1-ethynyl-7-hydroxy-6-(3-hydroxy-1-octenyl)-2-azabicyclo[3.3.9]-oct-2-en-3-yl]thiobutanoic acid, 4-[7-hydroxy-6-(3-hydroxy-1-octenyl)-1-(1-propynyl)-2-azabicyclo[3.3.0]oct-2-en-3-yl]thiobutanoic acid, 4-[1-(1,3-butadiynyl)-7-hydroxy-6-(3-hydroxy-1-octenyl)-2-azabicyclo[3.3.0]oct-2-en-3yl]thiobutanoic acid, 4-[7-hydroxy-6-(3-hydroxy-1-octenyl)-1-phenylethynyl-2-azabicyclo[3.3.0]oct-2-en-3-yl]thiobutanoic acid, 4-[1-ethenyl-7-hydroxy-6-(3-hydroxy-1-octenyl)-2-azabicyclo[3.3.0]oct-2-en-3-yl]thiobutanoic acid, 4-[1-cyano-7-hydroxy-6-(3-hydroxy-1-octenyl)-2-azabicyclo[3.3.0]oct-2-en-3-yl]thiobutanoic acid, 4-[1-ethenyl-7-hydroxy-6-(3-hydroxy-4-methyl-1-octenyl)-2-azabicyclo[3.3.0]oct-2-en-3-yl]thiobutanoic acid, 4-[1-ethynyl-7-hydroxy-6-(3-hydroxy-4-methyl-1-octenyl)-2-azabicyclo[3.3.0]oct-2-en-3-yl]thiobutanoic acid, 4-[7-hydroxy-6-(3-hydroxy-4-methyl-1-octenyl)-1-(1-propynyl)-2-azabicyclo[3.3.0]oct-2-en-3-yl]thiobutanoic acid, 4-[1-cyano-7-hydroxy-6-(3-hydroxy-4-methyl-1-octenyl)-2-azabicyclo[3.3.0]oct-2-en-3-yl]thiobutanoic acid, 4-[1-ethenyl-7-hydroxy-6-(3-hydroxy-4,4-dimethyl-1-octenyl)]-2-azabicylo[3.3.0]oct-2-en-3-yl]thiobutanoic acid, 4-[1-ethynyl-7-hydroxy-6-(3-hydroxy-4,4-dimethyl-1-octenyl)]-2-azabicylo[3.3.0]oct-2-en-3-yl]thiobutanoic acid, 4-[7-hydroxy-6-(3-hydroxy-4,4-dimethyl-1-octenyl)-1-(1-propynyl)-2-azabicyclo[3.3.0]oct-2-en-3-yl]thiobutanoic acid, 4-[1-cyano-7-hydroxy-6-(3-hydroxy-4,4-dimethyl-1-octenyl)-2-azabicyclo[3.3.0]oct-2-en-3-yl]thiobutanoic acid, 4-[1-ethenyl-7-hydroxy-6-(3-hydroxy-4-methyl-1-octen-6-ynyl)-2-azabicylo[3.3.0]oct-2-en-3-yl]thiobutanoic acid, 4-[1-ethynyl-7-hydroxy-6-(3-hydroxy-4-methyl-1-octen-6-ynyl)-2-azabicyclo[3.3.0]oct-2-en-3-yl]thiobutanoic acid, 4-[7-hydroxy-6-(3-hydroxy-4-methyl-1-octen-6-ynyl)-1-(1-propynyl-2-azabicyclo[3.3.0]oct-2-en-3-yl]thiobutanoic acid, 4-[1-cyano-7-hydroxy-6-(3-hydroxy-4-methyl-1-octen-6-ynyl)-2-azabicylo[3.3.0]oct-2-en-3-yl]thiobutanoic acid, 4-[6-(3-cyclopentyl-3-hydroxy-1-propenyl)-1-ethenyl-7-hydroxy-2-azabicyclo[3.3.0oct-2-en-3-yl]thiobutanoic acid, 4-[6-(3-cyclopentyl-3-hydroxy-1-propenyl)-1-ethynyl-7-hydroxy)-2-azabicyclo[3.3.0]oct-2-en-3-yl]thiobutanoic acid, 4-[6-(3-cyclopentyl-3-hydroxy-1-propenyl)-1-(1-propynyl)-7-hydroxy)-2-azabicyclo[3.3.0]oct-2-en-3-yl]thiobutanoic acid, 4-[1-cyano-6-(3-cyclopentyl-3-hydroxy-1-propenyl)-7-hydroxy-2-azabicyclo[3.3.0]oct-2-en-3-yl]thiobutanoic acid, 4-[6-(3-cyclohexyl-3-hydroxy-1-propenyl)-1-ethenyl-7-hydroxy-2-azabicyclo[3.3.0]oct-2-en-3-yl]thiobutanoic acid, 4-[6-(3-cyclohexyl-3-hydroxy-1-propenyl)-1-ethynyl-7-hydroxy-2-azabicyclo[3.3.0]oct-2-en-3-yl]thiobutanoic acid, 4-[6-(3-cyclohexyl-3-hydroxy-1-propenyl)-7-hydroxy-1-(1-propynyl)-2-azabicyclo[3.3.0]oct-2-en-3-yl]thiobutanoic acid, 4-[1-cyano-6-(3-cyclohexyl-3-hydroxy-1-propenyl)-7-hydroxy-2-azabicyclo[3.3.0]oct-2-en-3-yl]thiobutanoic acid, 4-[1-ethynyl-6-[5-(2-furyl)-3-hydroxy-1-pentenyl]-7-hydroxy-2-azabicyclo[3.3.0]oct-2-en-3-yl]thiobutanoic acid.

The above compounds can be converted into the desired esters or their salts.

The compound of the present invention represented by the general formula (I) may be prepared from (1S,5R,6R,7R)-2-oxa-3-oxo-6-[(3S)-3-hydroxyoct-1-enyl]-7-hydroxybicyclo[3.3.0]octane [E. J. Corey et.al., J. Am. Chem. Soc., 92, 397, (1970)] or (1S,5R,6S,7R)-2-oxa-3-oxo-6-hydroxymethyl-7-hydroxybicyclo[3.3.0]octane [E. J. Corey et.al., J. Am. Chem. Soc., 93, 1490, (1971)] according to the following process.

All the compounds described in the following reaction schemes are optically active substances which have the absolute configuration defined in the reaction schemes. The abbreviation for methyl is Me, ethyl is Et, tert-butyl is $^t$Bu or Bu$^t$, and phenyl is Ph.

Reaction Scheme 1

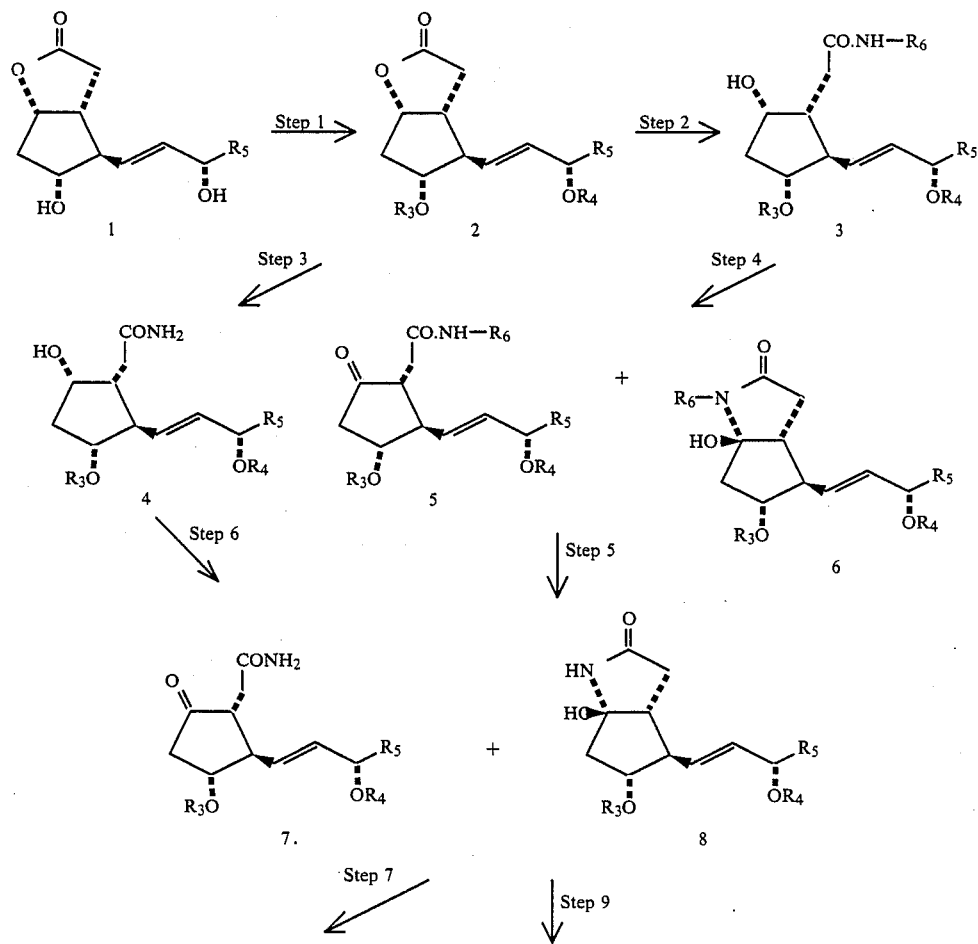

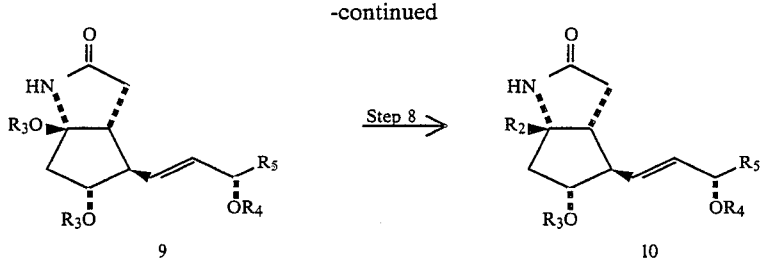

10a: R$_2$ = arylthio
10b: R$_3$ = alkyloxy

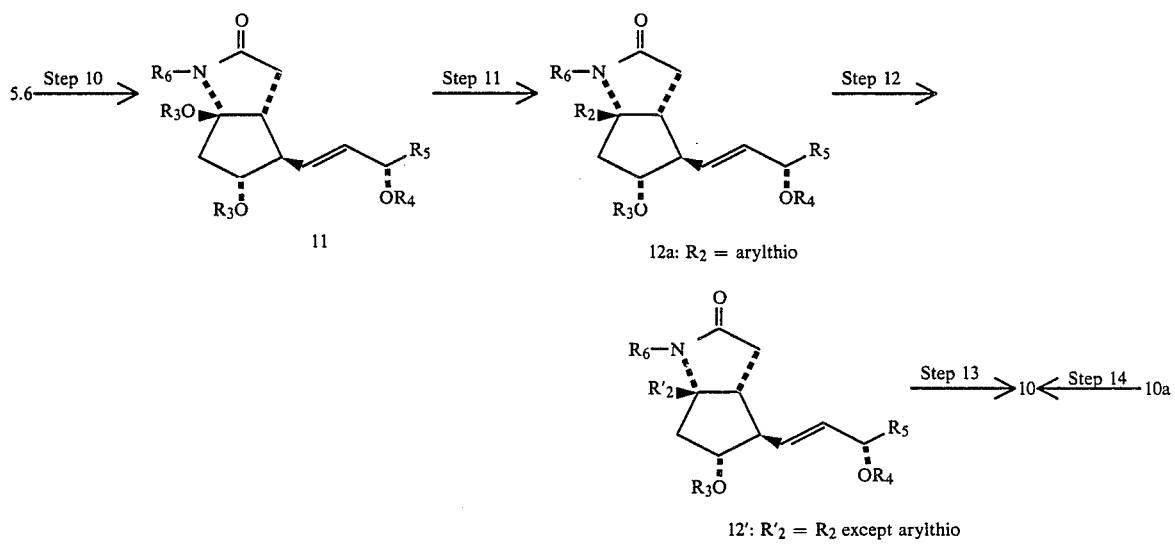

12′: R′$_2$ = R$_2$ except arylthio

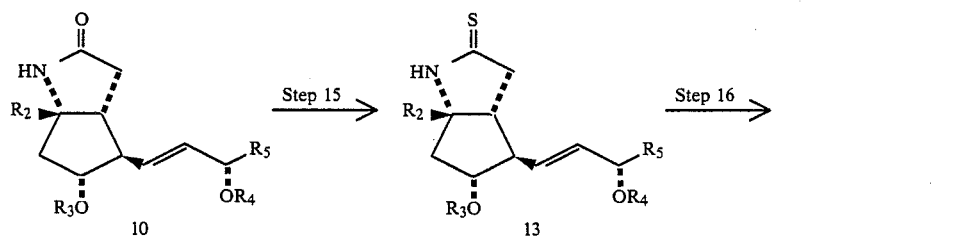

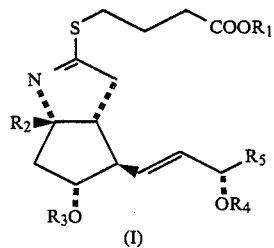

15 R$_3$.R$_4$: Protecting group
17 R$_3$.R$_4$: H, R$_1$: Carboxylate ester
18 R$_3$.R$_4$: H, R$_1$: Carboxylate salt
19 R$_3$.R$_4$: H, R$_1$: Free carboxylic acid Process 1

(Step 1)

In this step, a hydroxy-protecting group is introduced into hydroxy groups of the compound 1 in order to protect them in the succeeding reaction steps. The reaction may be carried out with tert-butyldimethylsilyl chloride, tert-butyldiphenylsilyl chloride, trimethylsilyl chloride, or the like in the presence of a base such as triethylamine, pyridine, or 4-dimethylaminopyridine at room temperature or under warming for a period of several hours to several days. As a solvent used in this reaction, an aromatic hydrocarbon, e.g., benzene, toluene; a chlorinated hydrocarbon, e.g., chloroform, dichloromethane; or dimethylformamide, is exemplified. The hydroxy-protection may also be achieved by treating the compound 1 with dihydropyrane in the presence of an acid catalyst such as p-toluenesulfonic acid, pyridinium p-toluenesulfonate, Amberlyst 15 (Rohm & Haas Co.) at room temperature. As a solvent, an ethereal solvent, e.g., diethyl ether, tetrahydrofuran; a hydrocarbon, e.g., hexane; an aromatic hydrocarbon, e.g., benzene, toluene; or a chlorinated hydrocarbon, e.g., chloroform, dichloromethane is exemplified.

(Step 2)

In this step, the lactone 2 is allowed to react with an amine to give the hydroxyamide 3. The reaction is carried out with an amine such as an alkylamine, e.g., methylamine, ethylamine, n-propylamine, 2-propylamine, n-butylamine, 2-butylamine; an cycloalkylamine, e.g., cyclopentylamine, cyclohexylamine; benzylamine; or a substituted benzylamine, e.g., 2-chlorobenzylamine, 2,4,6-trimethylbenzylamine, 2-methoxybenzylamine, 2,4-dimethoxybenzylamine, 3,4-dimethoxybenzylamine, in a solvent, (when the aforementioned amine is liquid, it also works as solvent), or water; an alcohol, e.g., methanol, ethanol; an ethereal solvent, ethyl ether, tetrahydrofuran, dioxane; or an aromatic hydrocarbon solvent, e.g. benzene, toluene, xylene, at room temperature or under warming for a period of several tens of hours. In order to accelerate the reaction, a base such as 2-hydroxypyridine or sodium methoxide may be added as a catalyst.

(Step 3)

In this step, the lactone 2 is allowed to react gradually with ammonia to give the hydroxylactone 4. This step may be carried out, for example, by reacting the lactone 2 with ammonia in an alcohol solvent, e.g., methanol, ethanol, under heating for a period of several tens of hours. This reaction may be carried out preferably in an autoclave. If required, sodium methoxide may be used as a catalyst.

(Step 4)

In this step, the compound 3 is oxidized into the keto-amide 5 and the hydroxy-lactam 6. The reaction is carried out in the following manners: (1) usuing a chromic acid derived oxidizing agent, e.g., Jones' reagent, Collins' reagent, pyridinium chlorochromate or pyridinium dichromate; or (2) using dimethylsulfoxide combined with oxalyl chloride, sulfuryl chloride or the like, or pyridinium sulfur trioxide combined with a base such as triethylamine, 4-dimethylaminopyridine as an oxidizing agent. The reaction is achieved in a solvent, e.g., acetone, benzene, chloroform, dichloromethane, ether, which may be chosen according to the property of the agent used under cooling or warming within a period of several tens of minutes to several hours.

(Step 5)

In this step, the substituent $R_6$ of the N-substituted keto-amide 5 is removed oxidatively to give the keto-amide 7 and hydroxy-lactam 8. As an oxidizing agent used in this reaction, 2,3-dichloro-5,6-dicyano-1,4-benzoquinone, potassium persulfate, cerium ammonium nitrate, or the like is exemplified. As a solvent, an aromatic solvent, e.g., benzene, xylene; a chlorinated hydrogen, e.g., chloroform, dichloromethane; an ethereal solvent, e.g., ethyl ether, tetrahydrofuran, dioxane; or an alcohol, e.g., methanol, ethanol is used with a proper amount of water, which may be used singly or combined according to the property of the agent. The reaction is achieved at room temperature or under heating within a period of several tens of minutes to several hours.

(Step 6)

In this step, the hydroxyamide 4 is oxidized into the keto-amide 7. The reaction is carried out by the use of an oxidizing agent such as chromic acid derived one, e.g., Jones' reagent. Collins' reagent, pyridinium chlorochromate, pyridinium dichromate, in a solvent such as chlorinated hydrocarbon, e.g., chloroform, dichloromethane; an ethereal solvent, e.g., ethyl ether, tetrahydrofuran; acetone; or benzene under cooling or at room temperature for a period of several hours.

(Step 7)

In this step, the keto-amide 7 and/or hydroxy-lactam 8 is silylated to give the compound 9. The reaction may be carried out by the use of an alkylsilylating agent such as trimethylsilyl chlorie, trimethylsilyl bromide, triethylsilyl chloride, triethylsilyl bromide, hexamethyldisilazane, tert-butyldimethylsilyl chloride or tert-butyldiphenylsilyl chloride, in the presence of a base such as triethylamine, pyridine, or 4-dimethylaminopyridine in a dry solvent such as chlorinated hydrocarbon, e.g., chloroform, dichloromethane; ethereal solvent, e.g., ethyl ether, tetrahydrofuran; aromatic solvent, e.g., benzene, toluene, xylene, pyridine; dimethylsulfoxide; or dimethylformamide, or in a mixture of two or more solvents at room temperature or under heating for a period of several hours.

(Step 8)

In this step, the compound 9 is allowed to react with a substituted or unsubstituted benzenethiol or an alcohol in the presence of an acid catalyst to give the compound 10. As an acid catalyst, p-toluenesulfonic acid, formic acid, hydrochloric acid, sulfuric acid, boron trifluoride ethereate or the like is exemplified. As a substituted benzenethiol having the preferable substituent, methoxybenzenethiol, nitrobenzenethiol, toluenethiol, ethylbenzenethiol, or dimethylbenzenethiol is exemplified. As an alcohol, methanol, ethanol, propanol, isopropanol, butanol, or isobutanol is exemplified. The reaction is carried out in a solvent such as an ethereal solvent, e.g., ethyl ether, tetrahydrofuran; acetonitrile; dimethylsulfoxide; dimethylformamide; acetone, at room temperature for several tens of minutes to several hours. The aforementioned alcohol also works as solvent.

(Step 9)

In this step, the hydroxy-lactam 8 is allowed to react with an alcohol to give the compound 10. The reaction is achieved in the same manner as in Step 8.

(Step 10)

In this step, the keto-amide 5 and hydroxy-lactam 6 is silylated to give the compound 11. The reaction is achieved in the same manner as in Step 7.

(Step 11)

In this step, the compound 11 is allowed to react with a benzenethiol derivative in the presence of an acid catalyst to give the compound 12a. The reaction is achieved in the same manner as in Step 8.

(Step 12)

In this step, the desired alkyl group or alkynyl group is introduced into the compound 12a. The alkylation is carried out with an alkylating agent such as dialkyl zinc. The alkynylation is carried out with an alkynylating agent such as a mixture of dialkynyl zinc and alkynyl zinc halogenide. Both reactions are carried out in a solvent such as chlorinated hydrocarbon, e.g., chloroform, dichloromethane; aromatic solvent, e.g., benzene, toluene, xylene; or dioxane, under heating for a period of several tens of minutes to several tens of hours. The alkyl of the alkylating agent used includes $C_1$-$C_5$ straight or branched alkyl such as methyl, ethyl, propyl, isopropyl, butyl, isobutyl, tert-butyl, pentyl, isopentyl, and the like. The alkynyl of the alkynylating agent includes ethynyl or substituted ethynyl, e.g., 2-trimethylsilylethynyl, 1-propynyl, 1-butynyl, 1-pentynyl, 3-buten-1-ynyl, 3-penten-1-ynyl-, 4-penten-1-ynyl, 1,3-butadiynyl, 4-trimethylsilyl-1,3-butadiynyl, 1,3-pentadiynyl, 1,4-pentadiynyl, 2-phenylethynyl, methoxyphenylethynyl, nitrophenylethynyl, tolylethynyl, dimethylphenylethynyl, and the like.

(Step 13)

In this step, the substituent $R_6$ of the N-substituted lactam 12 is removed oxidatively to give the lactam 10. As an oxidizing agent used in this reaction, 2,3-dichloro-5,6-dicyano-1,4-benzoquinone, potassium persulfate, cerium ammonium nitrate, or the like is exemplified.

As a solvent, an aromatic solvent, e.g., benzene, xylene; a chlorinated hydrocarbon, e.g., chloroform, dichloromethane; an ethereal solvent, e.g., ethyl ether, tetrahydrofuran, dioxane; an alcohol, e.g., methanol, ethanol; or acetonitrile; is used with a proper amount of water and they are used singly or in a combination according to the property of the agent used. The reaction is achieved at room temperature or under heating within several tens of minutes to several hours.

(Step 14)

In this step, the phenylthio group of the compound 10a is displaced with a desired alkyl or alkynyl. The reaction is achieved in the same manner as in Step 12.

(Step 15)

In this step, the lactam 10 is converted into the thiolactam 13. This step is carried out in the following manners: (1) heating in an aromatic solvent such as benzene, toluene or xylene containing 2,4-bis(4-methoxyphenyl)-1,3-dithia-2,4-diphosphetan-2,4-disulfide (Lawesson's Reagent), if required, with a base such as triethylamine, pyridine, or 4-methylaminopyridine; or (2) reacting with phosphorus pentasulfide, phosphorus pentasulfide-pyridine complex, or the like in a solvent such as toluene, dimethoxyethane or pyridine. In this step, compounds having a mercapto group at the 1-position may sometimes be produced as by-product.

(Step 16)

In this step, the thiolactam 13 is alkylated with an alkyl halide to give the thiolactim ether 15. The reaction is carried out in a solvent such as chlorinated hydrocarbon, e.g., chloroform, dichloromethane; an ethereal solvent, e.g., tetrahydrofuran, dioxane, dimethoxyethane; an aromatic solvent, e.g., benzene, toluene, xylene; dimethylsulfoxide; or dimethylformamide, in the presence of a base such as potassium carbonate or sodium hydride under cooling or heating for a period of several tens of minutes to several hours. As an alkyl halide, methyl 4-iodibutyrate, ethyl 4-iodobutyrate, propyl 4-iodobutyrate, methyl 4-bromobutyrate, ethyl 4-bromobutyrate, propyl 4-bromobutyrate, methyl 4-chlorobutyrate, ethyl 4-chlorobutyrate or propyl 4-chlorobutyrate is exemplified. In this step, the thiolactim, the compound of the present invention is prepared. In this step, N-alkylated compounds may sometimes be produced as by-product.

(Step 17)

In this step, silyl groups of the compound 15 are removed to give the compound 17. The reaction is carried out in a solvent such as alcohol, e.g., methanol, ethanol; ether, e.g., ethyl ether, tetrahydrofuran; acetonitrile; or water, if necessary, using an agent such as acetic acid, hydrochloric acid, p-toluenesulfonic acid, hydrofluoric acid and pyridine or tetrabutylammonium fluoride at room temperature or under heating for a period of several tens of minutes to several hours. In this step, the compound of the present invention, of which hydroxy groups are not protected is prepared.

(Step 18)

In this step, the ester 17 is applied to an ester-exchange reaction or hydrolyzed with a proper base catalyst to give the compound of the present invention; the ester having a desired ester group or the carboxylate salt 18, respectively. The ester exchange reaction is easily achieved by the usual method, that is, the ester may be allowed to react with an alcohol having a desired alkyl in the presence of a base such as sodium methoxide at room temperature. The hydrolysis may also be carried out in a usual manner. If necessary, the carboxylate salt 18 may be converted into the free carboxylic acid 19, the compound of the present invention, by the use of a proper acid such as hydrochloric acid, acetic acid, phosphoric acid, citric acid or boric acid, or a buffer solution such as acetic acid/sodium acetate, citric acid/disodium hydrogenphosphate, citric acid/sodium hydroxide, phosphoric acid/sodium hydroxide, boric acid/sodium hydroxide or acetic acid/sodium hydroxide.

Reaction Scheme 2

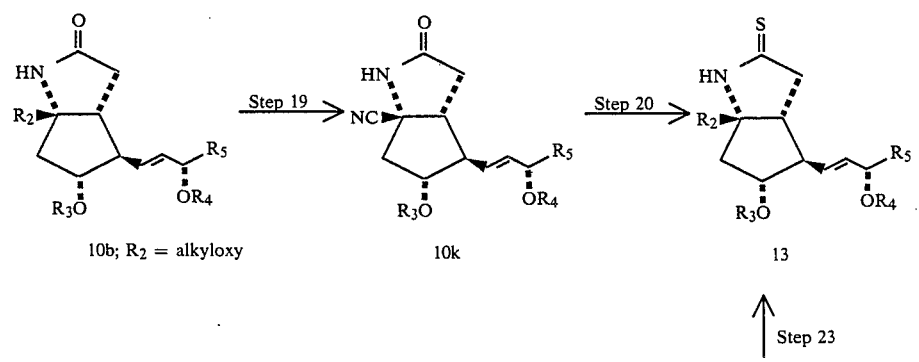

-continued
Reaction Scheme 2

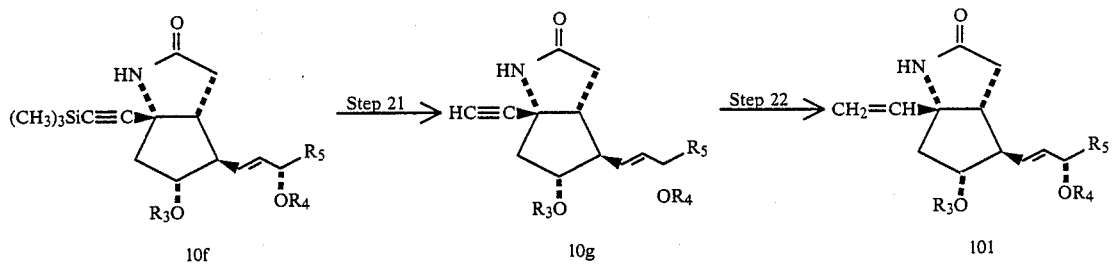

Process 2

(Step 19)
In this step, the 1-methoxy group of the compound 10b is displaced with cyano group. This step may be carried out by reacting cyanotrimethylsilane in the presence of a Lewis acid such as boron irfluoride ethereate. The reaction is achieved at room temperature within a period of several hours.

(Step 20)
In this step, the lactam 10k is converted into the thiolactam 13. This step may be carried out in the same manner as in Step 15.

(Step 21)
In this step, the trimethylsilyl group of the compound 10f is selectively removed. This step may be carried out by using base, e.g., potassium carbonate, sodium carbonate, as a catalyst in an alcohol, e.g., methanol, ethanol. The reaction is achieved at room temperature within a period of several hours.

(Step 22)
In this step, the ethynyl group is reduced into ethenyl group. As a catalyst, Lindler catalyst, palladium-barium sulfate with quinoline, or Raney Nickel may be used. As a solvent, an alcohol, e.g., methanol, ethanol or an aromatic solvent, e.g., benzene is used. The reaction is carried out at ordinary temperature and atmospheric pressure in an atmosphere of hydrogen for several hours. As an alternative manner, an ammonia solution of alkali metal, e.g., lithium, sodium, may be used.

(Step 23)
In this step, the lactam 10l is converted into the thiolactam 13. This step may be carried out in the same manner as in Step 15.

(Step 24)
In this step, the thiolactam 13 is alkylated with an alkyl halide to give the thiolactim ether 15. This step may be carried out in the same manner as in Step 16.

In this step, the thiolactim, the compound of the present invention is prepared.

(Step 25)
In this step, silyl groups of the compound 15 are removed to give the compound 17. The reaction may be carried out in the same manner as in Step 17.

In this step, the compound of the present invention, of which hydroxy groups are not protected is prepared.

Reaction Scheme 3

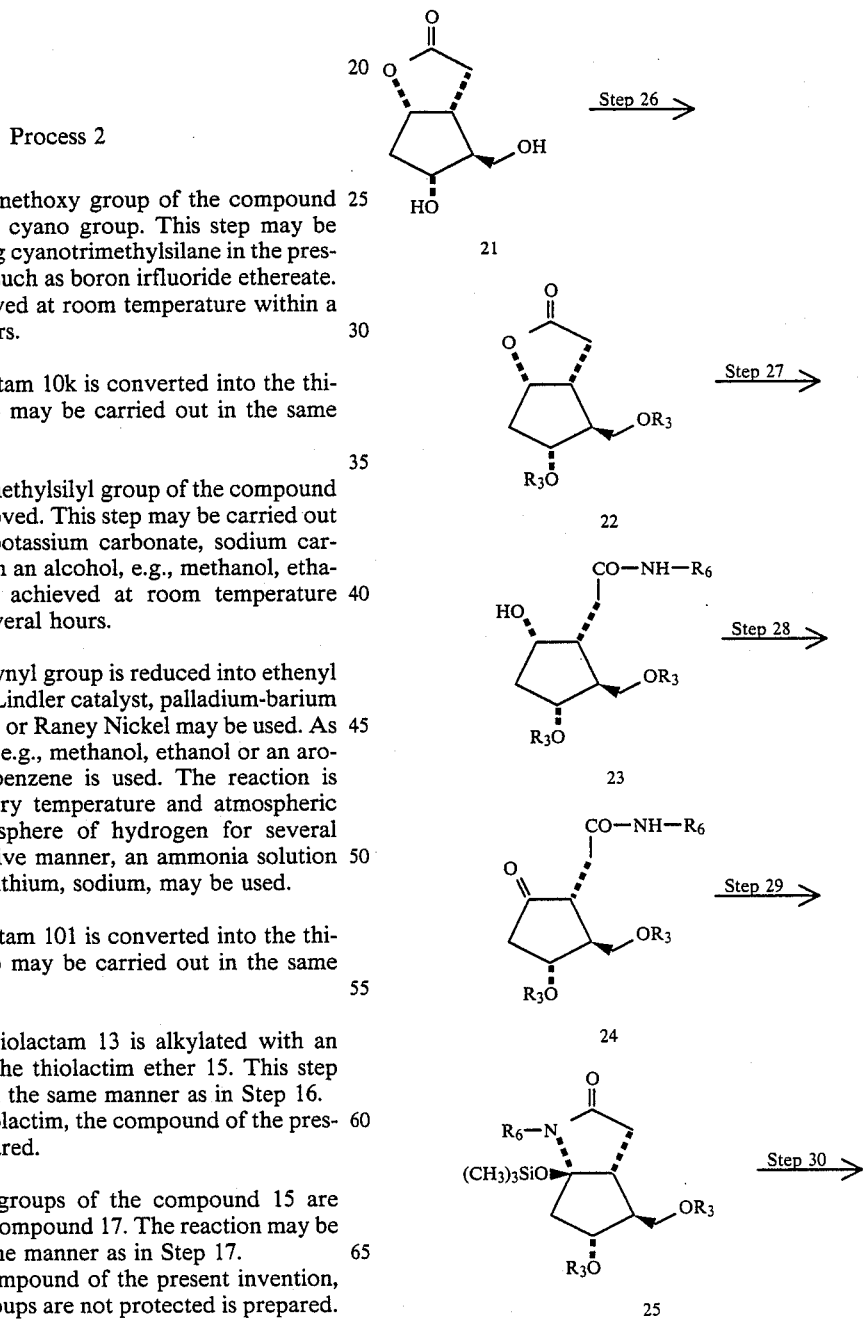

-continued
Reaction Scheme 3

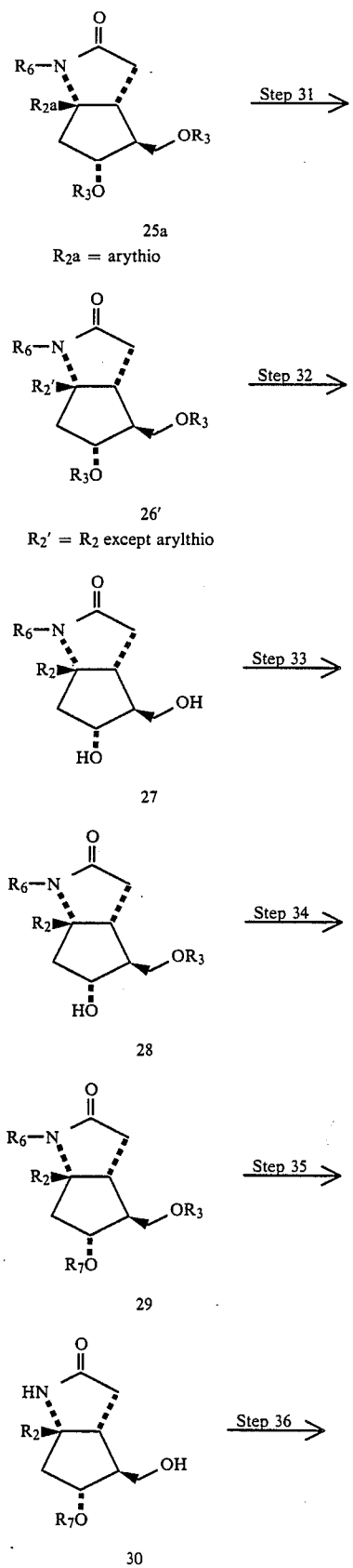

25a
R$_{2a}$ = arythio

26'
R$_2$' = R$_2$ except arylthio

27

28

29

30

-continued
Reaction Scheme 3

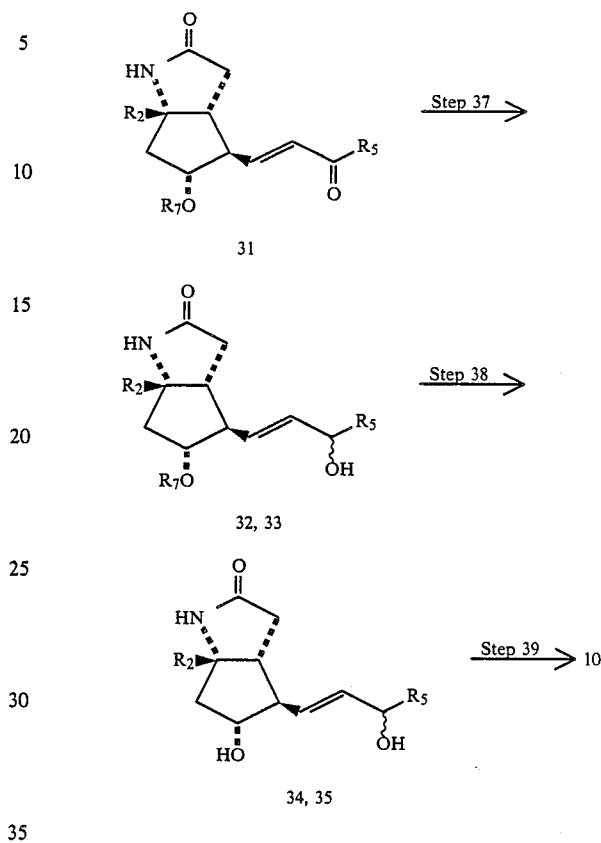

31

32, 33

34, 35

Process 3

(Step 26)
In this step, a hydroxy-protecting group is introduced into the hydroxy groups of the compound 21. This step may be carried out in the same manner as in Step 1.

(Step 27)
In this step, the lactone 22 is allowed to react with an amine to give the hydroxyamide 23. This step may be carried out in the same manner as in Step 2.

(Step 28)
In this step, the compound 23 is oxidized into the keto-amide 24. This step may be carried out in the same as in Step 4.

(Step 29)
In this step, the keto-amide 24 is silylated to give the compound 25. This step may be carried out in the same manner as in Step 7.

(Step 30)
In this step, the compound 25 is allowed to react with a substituted or unsubstituted benzenethiol in the presence of an acid catalyst to give the compound 26a. This step may be carried out in the same manner as in Step 8.

(Step 31)
In this step, the desired substituent is introduced into the compound 26a. This step may be carried out in the same manner as in Step 12.

(Step 32)
In this step, silyl groups of the compound 26' are removed to give the compound 27. This step may be carried out in the same manner as in Step 17. In this reaction, when the 1-substituent is trimethylsilylethynyl, it is converted into ethynyl.

(Step 33)

In this step, the hydroxy group of the 6-side chain of the compound 27 is selectively protected. The reaction is carried out using trimethylsilyl chloride, tert-butyldimethylsilyl chloride, tert-butyldiphenylsilyl chloride or the like in the presence of a base such as triethylamine, pyridine, or 4-dimethylaminopyridine at room temperature or under warming for a period of several hours to several days. As a solvent, an aromatic solvent, e.g., benzene, xylene; a chlorinated hydrocarbon, e.g. chloroform, dichloromethane; or dimethylformamide is exemplified.

(Step 34)

In this step, the alcohol 28 is protected with a protecting group which is relatively stable in acidic condition. The reaction is carried out by reacting the alcohol 28 with an acid anhydride or acid chloride. As an acyl group forming an acid anhydride or acid chloride, acetyl, propionyl, benzoyl, a substituted benzoyl, e.g., 3-methylbenzoyl, 4-phenylbenzoyl, 2-nitrobenzoyl; or 1-naphthoyl, 2-naphthoyl; is exemplified.

The alcohol 28 is allowed to react with an acid anhydride or acid chloride in the presence of a base such as pyridine, triethylamine, or 4-dimethylaminopyridine in a solvent such as a chlorinated hydrocarbon, e.g., chloroform, dichloromethane, carbon tetrachloride; or dioxane at room temperature for a period of several hours. When the alcohol 28 is allowed to react with an acid anhydride, the reaction may be carried out without any solvent.

(Step 35)

In this step, the substituent $R_6$ of the N-substituted lactam 29 is removed oxidatively to give the lactam 30. This step may be carried out in the same manner as in Step 13. Depending on the condition, protecting group, and agent used, the silyl group may be removed.

When the silyl group remains, it may be removed by further acid treatment.

When the 1-substituent of the compound 30 is ethynyl, it may be reduced to prepare the 1-ethenyl compound in the same manner as in Step 22, if necessary.

(Step 36)

In this step, the alcohol 30 is oxidized into the aldehyde, which is further allowed to react with a phosphonic acid ester to give the enone 31. The oxidation may be carried out in the same manner as in Step 4.

The reaction to prepare the enone 31 may be carried by the Horner-Wadsworth-Emmons Reaction using a base such as sodium hydride or sodium amide in a solvent such as 1,2-dimethoxyethane or tetrahydrofuran.

The phosphonic acid esters used in this reaction are those having a desired side chain to be condensed, namely, dimethyl 2-oxoheptylphosphonate, dimethyl 2-oxo-3-methylheptylphosphonate, dimethyl 2-oxo-3,3-dimethylheptylphosphonate, dimethyl 2-oxo-3-methyl-5-heptynylphosphonate, dimethyl 2-oxo-2-cyclohexylethylphosphonate, dimethyl 2-oxo-2-cyclopentyl ethylphosphonate, dimethyl 4-(2-furyl)-2-oxo-butylphosphonate, or the like.

(Step 37)

In this step, the enone 31 is reduced into the unsaturated alcohol 32. As a reducing agent, aluminum isopropoxide, diisobornylaluminium isopropoxide, sodium cyanoborohydride, potassium tri-sec-butyl borohydride, zinc borohydride, sodium borohydride, a combination of sodium borohydride and cerium (III) chloride, diisobutyl aluminium 2,6-di-tert-butyl-4-methylphenoxide, lithium hexyllimonyl borohydride, BINAL-H or the like may be used. As a solvent, an ethereal solvent, e.g., diethyl ether, tetrahydrofuran, an alcohol, e.g., methanol, ethanol, an aromatic solvent, e.g., benzene, toluene, or a chlorinated hydrocarbon, e.g., dichloromethane, chloroform may be used singly or combined according to the property of the agent. The reaction is carried out under cooling or at room temperature for a period of several tens of minutes. The alcohol prepared in this step is a mixture of the epimers.

(Step 38)

In this step, the 7-hydroxy-protecting group is removed. The reaction is carried out using a base such as sodium methoxide, sodium hydroxide, sodium carbonate, or calcium carbonate in an alcohol solvent such as methanol or ethanol at room temperature for a period of several hours.

(Step 39)

In this step, the hydroxy group of the compound 34 or 35 is protected. This step may be carried out in the same manner as in Step 1.

(Step 40)

In this step, the lactam 10 is converted into the thiolactam 13. This step may be carried out in the same manner as in Step 15.

When the 1-substituent of the compound 13 is ethynyl, the ethenyl compound may be prepared by reduction carried out in the same manner as in Step 22, if necessary.

(Step 41)

In this step, the thiolactam 13 is alkylated with an alkyl halide to give the thiolactim ether 15. This step may be carried out in the same manner as in Step 16.

In this step, the thiolactim ether the compound of the present invention is prepared.

(Step 42)

In this step, silyl groups of the compound 15 are removed to give the compound 17. This step may be carried out in the same manner as in Step 17.

In this step, the compound of the present invention, of which hydroxy groups are not protected is prepared.

(Step 43)

In this step, the ester 17 is applied to an ester-exchange reaction or hydrolyzed with a proper base catalyst to give the compound of the present invention. This step may be carried out in the same manner as in Step 18.

In the reaction scheme, $R_1$, $R_2$, $R_3$, $R_4$ and $R_5$ each is the same as defined in the general formula (I). $R_6$ is straight or branched lower alkyl, cycloalkyl, substituted or unsubstituted benzyl (e.g., benzyl, 2-chlorobenzyl, 2,4,6-trimethylbenzyl, 2-methoxybenzyl, 2,4-dimethoxybenzyl, 3,4-dimethoxybenzyl), or the like. $R_7$ is alkanoyl, e.g., acetyl, propionyl, benzoyl, substituted benzoyl (e.g., 3-methylbenzoyl, 4-phenylbenzoyl, 2,4-dihydrobenzoyl, 2-nitrobenzoyl), 1-napthoyl, 2-naphthoyl, or the like.

The following Examples are included to explain the embodiment of the present inventin in more detail, but these are not intended to limit the scope of the invention.

All the compounds described in the following Examples are optically active substances which have the absolute configuration defined in the reaction formulae. The absolute configuration of the starting material is designated by the R and S denotations, which, however, are omitted in the subsequent intermediates and final products in Examples, since the original configuration is retained to the final product.

The abbreviation for phenyl is Ph, methyl is Me, ethyl is Et, and tert-butyl is $^t$Bu or Bu$^t$.

EXAMPLE

Example for the Preparation of the Intermediates

Example I-1

Preparation of 2-oxa-3-oxo-6-[(3S)-3-tert-butyldiphenylsilyloxyoct-1-enyl]-7-tert-butyldiphenylsilyloxybicyclo[3.3.0]octane 2

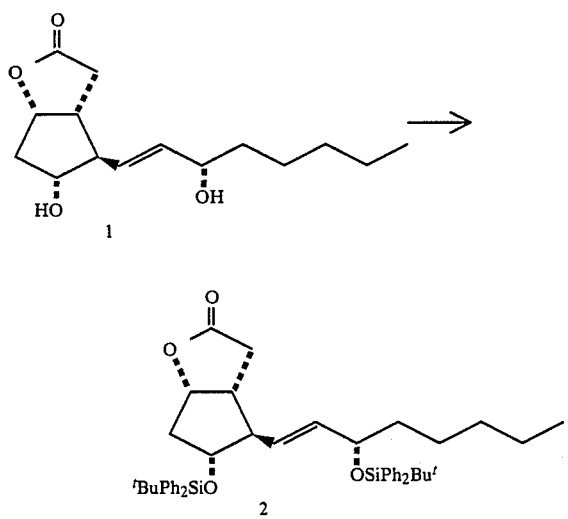

In an atmosphere of nitrogen, 5.52 g (45.24 mmol) of 4-dimethylaminopyridine and 9.51 g (34.72 mmol) of tert-butyldiphenylsilyl chloride are added to a solution of 3.03 g (11.30 mmol) of (1S,5R,6R,7R)-2-oxa-3-oxo-6-[(3S)-3-hydroxyoct-1-enyl]-7-hydroxybicyclo[3.3.0]octane 1 in 90 ml of dry N,N-dimethylformamide, and the mixture is allowed to stand at room temperature for 3 days. The reaction mixture is poured into ice water, then extracted with ethyl acetate three times. The extract is washed with water and dried over anhydrous magnesium sulfate and evaporated to give 13.73 g of a residue, which is purified by column-chromatography (300 g of silica gel, eluted with benzene-benzene/ethyl acetate=20/1) to give 8.40 g of the compound 2 as an oil (quantitative yield).

MS: m/z 744(M+), m/z 687(M+ −tBu).

[α]$_D$−25.2±1.3° (23.5° C., c=0.5.11, CHCl$_3$).

IR: νmax(CHCl$_3$) 3080, 1768, 1592, 1112, 1082 cm$^{-1}$.

NMR: δppm(CDCl$_3$) 0.80(3H), 1.01(18H, s), 3.75–4.15(2H, m), 4.75 (1H, m), 4.8–5.35(2H, m), 7.1–7.8(20H, m).

Example I-2

Preparation of N-(2,4-dimethoxybenzyl)-[1-tert-butyldiphenylsilyloxy-2-[(3S)-3-tert-butyldiphenylsilyloxyoct-1-enyl]-4-hydroxycyclopent-3-yl]-acetoamide 3

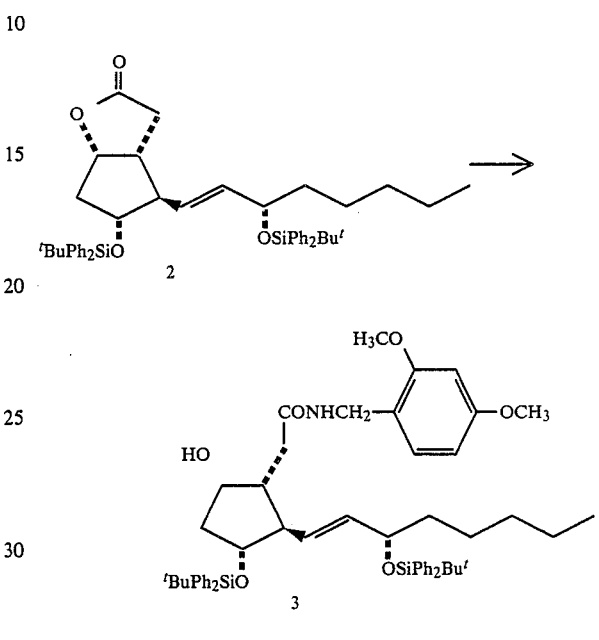

In an atmosphere of nitrogen, a mixture of 6.365 g (8.55 mmol) of the lactone 2 (prepared in Example I-1), 844 mg (8.77 mmol) of 2-hydroxypyridine, and 15 g (89.8 mmol) of 2,4-dimethoxybenzylamine is stirred on an oil bath at 100° C. for 2 hours and 10 minutes, and then allowed to stand at room temperature overnight. The reaction mixture is poured into a saturated aqueous solution of sodium chloride and extracted with ethyl acetate twice. The extract is washes successively with 1N hydrochloric acid, a saturated aqueous solution of sodium chloride, a dilute aqueous solution of sodium hydrogencarbonate, and a saturated aqueous solution of sodium chloride, dried over anhydrous magnesium sulfate and evaporated to give 12.65 g of residue, which is purified by column chromatography (260 g of silica gel, benzene:ethyl acetate=50:1–5:1) to give 7.32 g of the compound 3 as an oil (94% yield).

MS: m/z 912(MH+), m/z 854(M+ −tBu).

[α]$_D$+1.5±0.8° (23.5° C., c=0.500, CHCl$_3$).

IR: νmax(CHCl$_3$) 3450, 3005, 1650, 1616, 1590, 1508, 1111, 1036 cm$^{-1}$.

NMR: δppm(CDCl$_3$) 0.79(3H), 1.02(18H, s), 3.78(6H, s), 3.7–4.3 (2H, m), 4.32(2H, d, J=6 Hz), 5.25(2H, m), 5.98(1H, t, J=6 Hz), 6.45(2H, m), 7.1–7.8(21H, m).

EXAMPLE I-3

Preparation of
[1-tert-butyldiphenylsilyloxy-2-((3S)-3-tert-butyldi-phenylsilyloxyoct-1-enyl)-4-hydroxycyclopent-3-yl]acetoamide 4

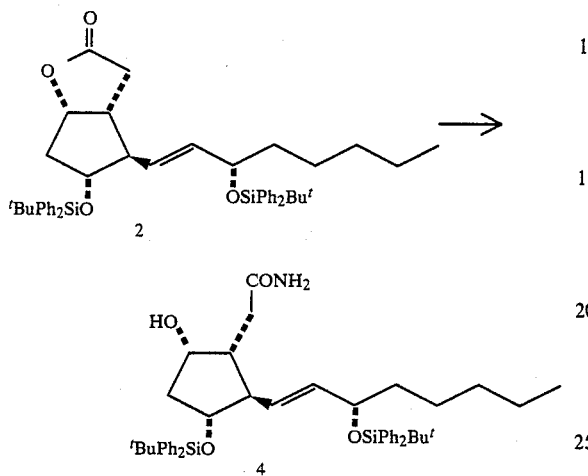

To 1.79 g (2.40 mmol) of the lactone 2 (prepared in Example I-1) are added 10 ml of methanol and 55 ml of saturated methanol solution of ammonia, and the mixture is heated in an autoclave at 100° C. for 27 hours. After cooling, the reaction mixture is evaporated to give 2.80 g of residue, which is purified by column chromatography (20 g of silica gel; eluted with benzene-benzene:ethyl acetate=1:1) to give 530 mg of the starting material lactone 2 (30% yield) and 1.12 g of the oily compound 4 (61% yield). MS: m/z 704(M+ −tBu). $[\alpha]_D+2.2\pm0.5°$ (25° C., c=0.820, CHCl$_3$).

IR: $\nu$max(CHCl$_3$) 3535, 3510, 3425, 3082, 3005, 1675, 1593, 1113 cm$^{-1}$.

NMR: $\delta$ppm(CDCl$_3$) 0.80(3H), 1.02(18H, s), 3.8–4.25(3H, m), 5.23 (2H, m), 5.78(2H, br.s), 7.15–7.75(20H, m).

Example I-4

Preparation of
N-(2,4-dimethoxybenzyl)-[3-((3S)-3-tert-butyldiphenyl-silyloxyoct-1-enyl)-4-tert-butyldiphenylsilyloxycyclopentan-1-on-2-yl]-acetoamide 5 and
N-2,4-dimethoxybenzyl)-1-hydroxy-2-aza-3-oxo-6-[(3S)-3-tert-butyldiphenylsilyloxyoct-1-enyl]-7-tert-butylphenylsilyloxybicyclo[3.3.0]octane 6

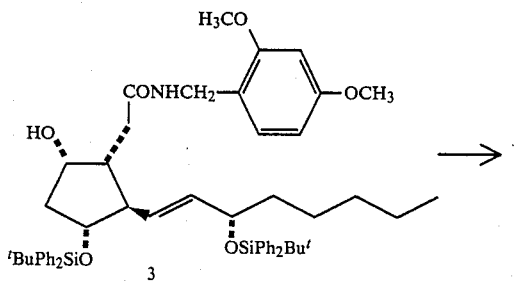

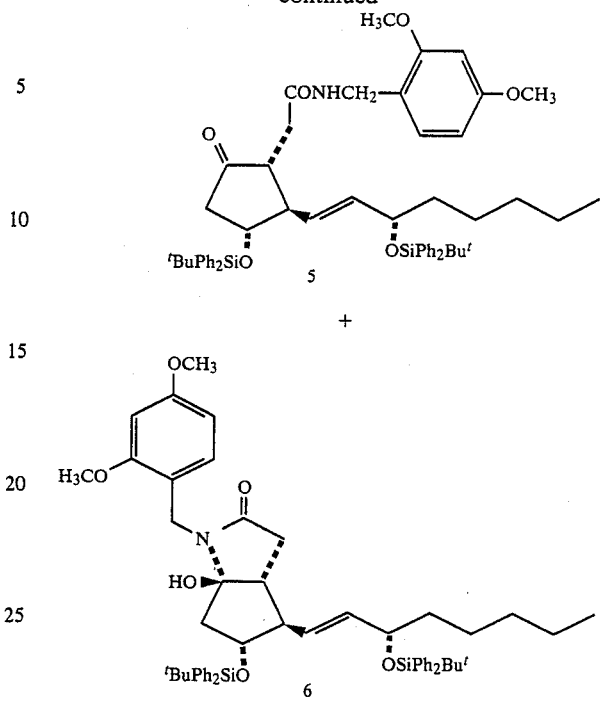

In an atmosphere of nitrogen, a solution of 2.47 g (19.49 mmol) of oxalyl chloride in 100 ml of dry dichloromethane is cooled to −60° C., then a solution of 3.19 g (40.83 mmol) of dimethylsulfoxide in 11 ml of dry dichloromethane is dropwise added thereto under stirring over a 6 minute period, and the mixture is stirred at the same temperature for 30 minutes. A solution of 7.32 g (8.03 mmol) of the alcohol (prepared in Example I-2) and 4.21 g (41.62 mmol) of triethylamine in 150 ml of dry dichloromethane is added dropwise to the above mixture over a 50 minute period, and the resulting mixture is stirred at the same temperature for additional 1 hour. After the reaction mixture is brought to room temperature, water is added and the reaction mixture is acidified with 1N hydrochloric acid, and extracted with dichloromethane three times. The extract is washed with water, dried over anhydrous magnesium sulfate and evaporated to give 7.52 g of residue, which is crystallized from a mixture of ethyl ether and n-pentane to give 4.87 g of the compound 5 (67% yield). The mother liquor (2.53 g) is applied to column chromatography (Merck; Lober column size C; eluted with benzene:ethyl acetate=9:1–3:1) to give further 1.97 g of the compound 5 (27% yield) and 143 mg of the compound 6 (2% yield ). The crude product 5 is recrystallized from a mixture of ethyl ether and n-pentane to give the compound 5 as crystals, mp. 97°–98° C.

Anal. Calcd. (%) for C$_{56}$H$_{71}$O$_6$NSi$_2$: C 73.89, H 7.86, N 1.54, Found (%): C 73.74, H 7.87, N 1.71.

MS: m/z 852(M+ −tBu).

$[\alpha]_D$−23.1±1.2° (23.5° C., c=0.510, CHCl$_3$).

IR: $\nu$max(CHCl$_3$) 3450, 3075, 3005, 1741, 1670, 1617, 1592, 1509, 1112 cm$^{-1}$.

NMR: $\delta$ppm(CDCl$_3$) 0.81(3H), 1.02(18H, s), 3.75(3H, s), 3.76(3H, s), 4.0(2H, m), 4.30(2H, d, J=6 Hz), 5.35(2H, m), 5.82(1H, t, J=6 Hz), 6.42(2H, m), 7.05–7.8(21H, m).

The crude product 6 is recrystallized from a mixture of ethyl ether and n-pentane to give the compound 6 as crystals, m.p. 123°–125° C.

Anal. Calcd. (%) for $C_{56}H_{71}O_6NSi_2$: C 73.89, H 7.86, N 1.54, Found (%): C 73.95, H 7.69, N 1.51.

$[\alpha]_D-5.2\pm0.9°$ (24° C., c=0.517, CHCl$_3$).

IR: $\nu$max(CHCl$_3$) 3460, 3075, 3005, 1678, 1616, 1591, 1508, 1112, 1042 cm$^{-1}$.

NMR: $\delta$ppm(CDCl$_3$) 0.80(3H), 0.98(9H, s), 1.04(9H, s), 3.68(3H, s), 3.73(3H, s), 4.07(2H, m), 4.19(1H, d, J=15 Hz), 4.47(1H, d, J=15 Hz), 5.41(2H, m), 6.41(2H, m), 7.2-7.75(21H, m).

Example I-5

Preparation of
[3-((3S)-3-tert-butyldiphenylsilyloxyoct-1-enyl)-4-tert-butyldiphenylsilyloxycyclopentan-1-on-2-yl]acetoamide 7 and
1-hydroxy-2-aza-3-oxo-6-[(3S)-3-tert-butyldiphenylsilyloxyoct-1-enyl]-7-tert-butyldiphenylsilyloxybicyclo[3.3.0]octane 8

(1) From N-benzylamide 5

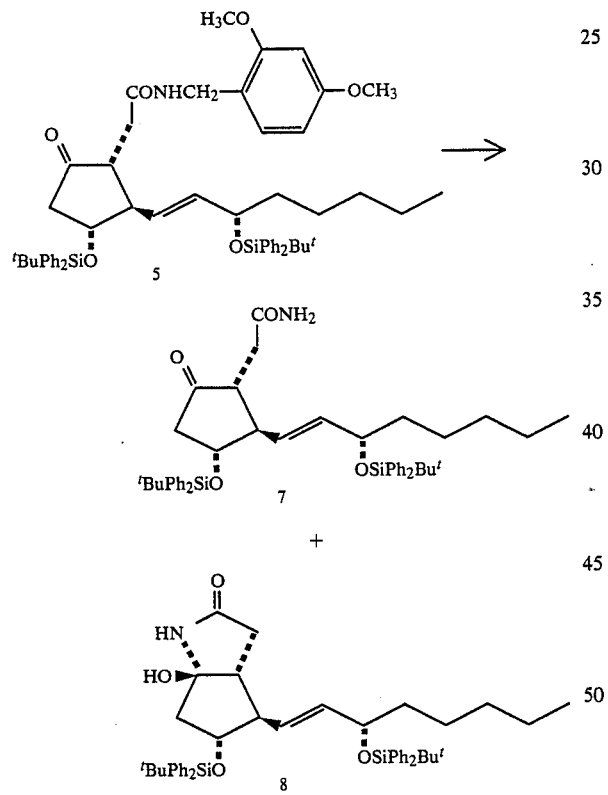

To a solution of 1.583 g (1.74 mmol) of N-benzylamide 5 (prepared in Example I-4) in 60 ml of dichloromethane/water (19:1) mixture is added 595 mg (2.62 mmol) of 2,3-dichloro-5,6-dicyano-1,4-benzoquinone and the mixture is stirred at room temperature for four and half hours. The reaction mixture is poured into water and extracted with dichloromethane three times. The extract is successively washed with 1N sodium thiosulfate and water, dried over anhydrous magnesium sulfate and evaporated to give 1.92 g of residue, which is applied to column chromatography (45 g of silica gel; eluted with benzene:ethyl acetate=20:1-ethyl acetate) to give 1.152 g of a mixture of keto-amide 7 and hydroxy-lactam 8. (This mixture may be applied to the following reaction without further purification.) Further, this mixture is purified by column chromatography (Lober column size B; elute with benzene:ethyl acetate=3:1-ethyl acetate) to give 751 mg of the compound 7 as a foamy material (57% yield) and 322 mg of the compound 8 as a foamy material (24% yield).

(2) From hydroxyamide 4

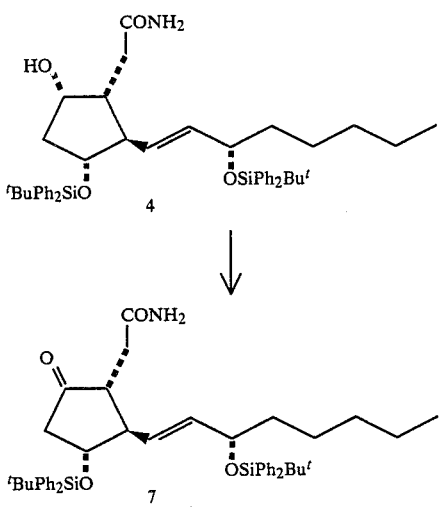

A solution of 317 mg (0.416 mmol) of the hydroxyamide 4 (prepared in Example I-3) in 10 ml of acetone is cooled to $-20°$ C., then 0.52 ml (0.624 mmol) of 1.2M Jones' reagent is added thereto under stirring over a 5 minute period, and the mixture is stirred at the same temperature for 5 hours and 45 minutes. Then, 0.5 ml of isopropanol is added, and further, the mixture is stirred at room temperature for 30 minutes. The reaction mixture is brought to room temperature and water is added, and then the mixture is neutralized with a dilute aqueous solution of sodium hydrogencarbonate and extracted with ethyl acetate three times. The extract is washed with eater, dried over anhydrous magnesium sulfate and evaporated to give 327 mg of the residue, which is purified by column chromatography (Lober column size B; eluted with benzene:ethyl acetate=4:1) to give 253 mg of the compound 7 as a foamy material (80% yield).

Keto-amide 7:

MS: m/z 759(M$^+$), 702(M$^+$ $-$tBu).

$[\alpha]_D-30.8\pm0.7°$ (22° C., c=1.007, CHCl$_3$).

IR: $\nu$max(CHCl$_3$) 3530, 3415, 3075, 3005, 1741, 1688, 1590, 1111 cm$^{-1}$.

NMR: $\delta$ppm(CDCl$_3$) 0.81(3H), 1.02(9H, s), 1.04 (9H, s), 4.07(2H, m), 5.46(4H, m), 7.0-7.8(20H, m).

Hydroxy-lactam 8:

MS: m/z 741(M$^+$ $-$H$_2$O), 702(M$^+$ $-$tBu).

$[\alpha]_D-4.4\pm0.6°$ (22.5° C., c=0.726, CHCl$_3$).

IR: $\nu$max(CHCl$_3$) 3590, 3430, 3080, 3010, 1693, 1591, 1112 cm$^{-1}$.

NMR: $\delta$ppm(CDCl$_3$) 0.80(3H), 1.00(9H, s), 1.03(9H, s), 4.03(2H, m), 5.30(2H, m), 6.75(1H, m), 7.0-7.8(20H, m).

Example I-6

Preparation of 1-trimethylsilyloxy-2-aza-3-oxo-6-[(3S)-3-tert-butyldiphenylsilyloxyoct-1-enyl]-7-tert-butyldiphenylsilyloxybicyclo[3.3.0]octane 9

(1) From the keto-amide 7

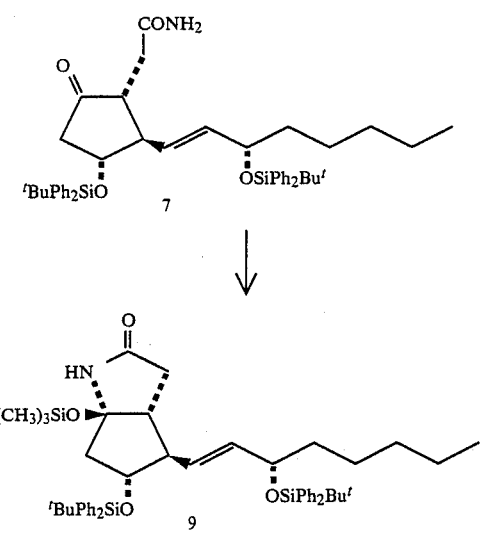

To a solution of 649 mg (0.855 mmol) of the keto-amide 7 (Example I-5) dissolved in 14 ml of a mixture of dried dichloromethane and dried pyridine (1:1) under a nitrogen atmosphere are added 1.05 g (8.60 mmol) of 4-dimethylaminopyridine and 470 mg (4.33 mmol) of trimethylsilyl chloride and the mixture is stirred for 3 hrs on an oil bath at 70° C. After cooling, the reaction mixture is concentrated, poured into ice water, and extracted 3 times with ethyl acetate. The extract is washed with water, dried over anhydrous magnesium sulfate, and evaporated to give 1.20 g of residue.

The residue is refined by column chromatography (silica gel 40 g, benzene:ethyl acetate (15:1)~ethyl acetate) to provide 560 mg (79% yield) of the compound 9 and 83 mg (13% yield) the hydroxy-lactam 8.

(2) From a mixture of the keto-amide 7 and the hydroxy-lactom 8

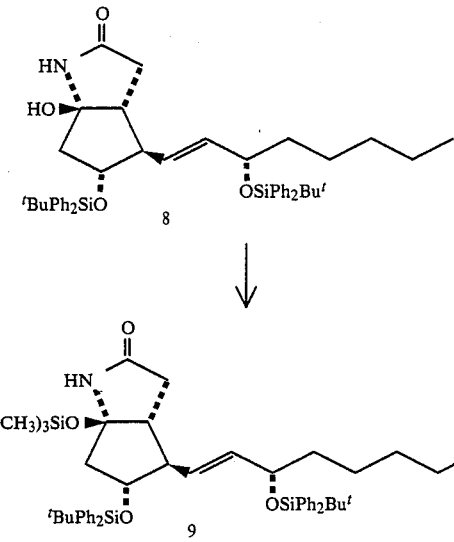

To a solution of 2.63 g (3.465 mmol) of a mixture of the keto-amide 7 and the hydroxy-lactam 8 (Example I-5) dissolved in 60 ml of a mixture of dry dichloromethane and dry pyridine (1:1) in a nitrogen atmosphere are added 4.24 g (34.70 mmol) of 4-dimethylaminopyridine and 1.88 g (17.41 mmol) of trimethylsilyl chloride and the mixture is stirred for 5 hrs on an oil bath at 70° C. After cooling, the reaction mixture is concentrated, poured into ice water, and extracted 3 times with ethyl acetate. The extract is washed with water, dried over anhydrous magnesium sulfate, and evaporated to give 3.77 g of residue. The residue is refined by column chromatography (silica gel 120 g, benzene:ethyl acetate (15:1)) to provide 2.61 g of compound 9 as a foamy material (90% yield).

MS: m/z 831 (M+), m/z 774 (M+ −tBu).

[α]$_D$ −11.1±0.9° (22.5° C., c=0.591, CHCl$_3$).

IR: νmax (CHCl$_3$) 3430, 3075, 3005, 1703, 1591, 111, 843 cm$^{-1}$.

NMR: δppm (CDCl$_3$) 0.0(9H, s), 0.80(3H, 1.01(9H, s), 1.04(9H, s), 4.04(2H, m), 5.34(2H, m), 6.83(1H, s), 7.1–7.8 (20H, m).

Example I-7

Preparation of 1-phenylthio-2-aza-3-oxo-6-[(3S)-3-tert-butyldiphenylsilyloxyoct-1-enyl]-7-tert-butyldiphenylsilyloxybicyclo[3.3.0]octane 10(S)a.

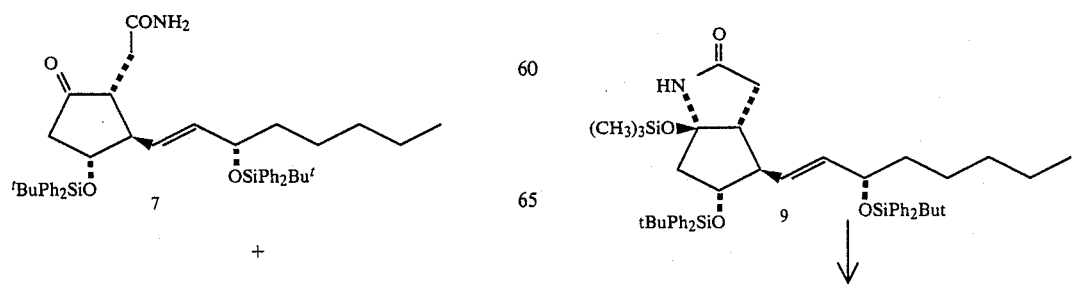

-continued

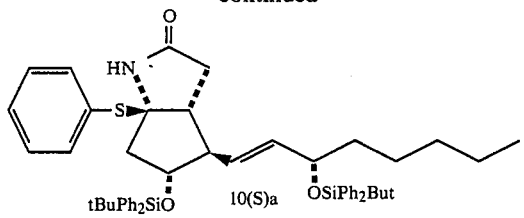

In a nitrogen atmosphere, 1.80 g (16.3 mmol) of thiophenol and 0.3 ml of 3N ethyl ether solution of hydrogen chloride are added to a solution of 2.676 g (3.22 mmol) of the trimethylsilyloxy-lactam 9 (Example I-6) in 30 ml dry ethyl ether and the mixture is stirred at room temperature for 2 hours. The reaction mixture is neutralized with powder sodium hydrogencarbonate and evaporated. The residue is purified by column chromatography (50 g of silica gel; eluted with benzene~benzene:ethyl acetate=2:1) to give 2.721 g of the compound 10(S)a as a foamy material (99% yield).

MS: m/z 794 (M+−tBu), m/z 742 (M+−PhS).

[α]$_D$+24.8±0.6° (23.5° C., c=1.015, CHCl$_3$).

IR: νmax (CHCl$_3$) 3435, 3090, 3020, 1704, 1594, 1115 cm$^{-1}$.

NMR: δppm (CDCl$_3$) 0.80(3H), 1.00(9H, s), 1.05(9H, s), 4.10(2H, m), 5.38(2H, m), 6.60(1H, s), 7.1–7.8(25H, m).

Example I-8

Preparation of 1-methoxy-2-aza-3-oxo-6-[(3S)-3-tert-butyldiphenylsilyloxyoct-1-enyl]-7-tert-butyldiphenylsilyloxybicyclo[3.3.0]octane 10(S)b (1) From hydroxy-lactam 8

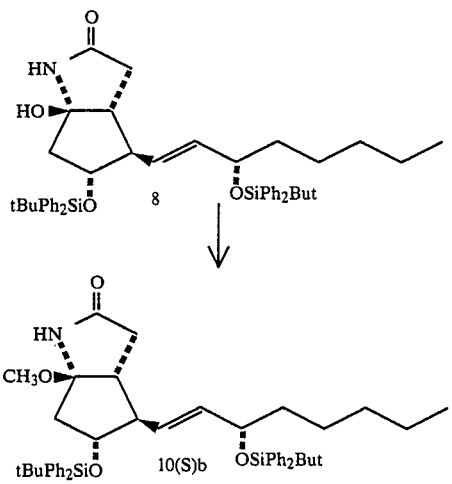

In 7 ml of methanol solution of hydrochloric acid (1N hydrochloric acid (1 ml) is dissolved in 50 ml of methanol) is dissolved 260 mg of the hydroxy-lactam 8 (Example I-5) and the mixture is stirred at room temperature for 1 hour and 40 minutes. The reaction mixture is neutralized with dilute aqueous solution of sodium hydrogencarbonate and then methanol is evaporated. The residue is poured into water and extracted 3 times with dichloromethane, and the extract is washed with water, dried over anhydrous magnesium sulfate, and evaporated to give 260 mg of residue, which is purified by column chromatography (10 g of silica gel, ben-zene:ethyl acetate=15:1–4:1) to give 230 mg of the compound 10(S)b (87% yield).

(2) From trimethylsilyloxy-lactam 9.

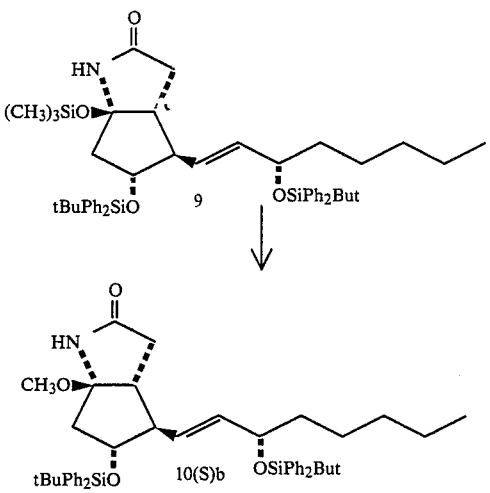

In 10 ml of methanol solution of hydrochloride acid (1N hydrochloric acid (1 ml) is dissolved in 50 ml of methanol.) is dissolved 435 mg of the trimethylsilyloxy-lactam 9 (Example I-6) and the mixture is stirred at room temperature for 55 minutes. Then, the reaction mixture is treated in the same manner as in Example I-8-(1) to give 400 mg of residue, which is purified by column chromatograhy (15 g of silica gel, benzene:ethyl acetate=4:1) to give 283 mg of the compound 10(S)b as a foamy material (95% yield).

MS: m/z 773 (M+), m/z 741 (M+−CH$_3$OH), 716 (M+−tBu).

[α]$_D$−3.2±0.6° (22.5° C., c=0.786, CHCl$_3$).

IR: νmax (CHCl$_3$) 3425, 3075, 3005, 1704, 1591, 1112 cm$^{-1}$.

NMR: δppm (CDCl$_3$) 0.81(3H), 1.01(9H, s), 1.04(9H, s), 3.01(3H, s), 4.03(2H, m), 5.33(2H, m), 6.77(1H, s), 7.1–7.8 (20H, m).

Example I-9

Preparation of N-(2,4-dimethoxybenzyl)-1-trimethylsilyloxy-2-aza-3-oxo-6-[(3S)-3-tert-butyldiphenylsilyloxyoct-1-enyl]-7-tert-butyldiphenylsilyloxybicyclo[3.3.0]octane 11

(1) From the keto-amide 5.

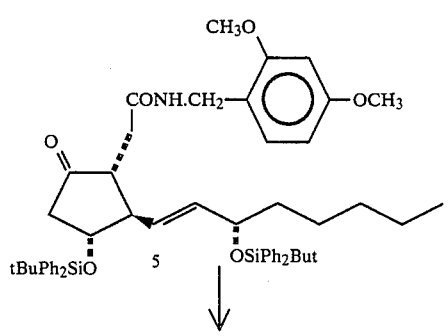

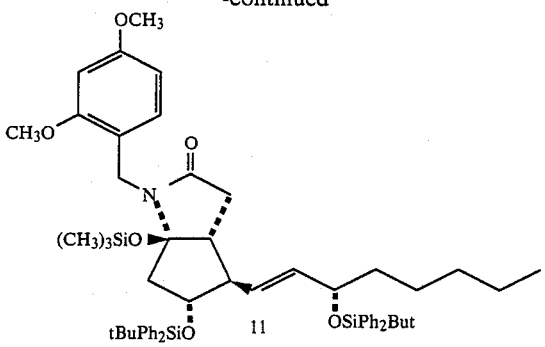

To a solution of 5.81 g (6.39 mmol) of the keto-amide 5 (Example I-4) dissolved in 100 ml of a mixture of dry dichloromethane and dry pyridine (1:1) are added 7.87 g (64.42 mmol) of 4-dimethylaminopyridine and 3.51 g (32.44 mmol) of trimethylsilyl chloride in a nitrogen atmosphere and the mixture is stirred for two and half hours on an oil bath at 70° C. After cooling, the reaction mixture is poured into iced water, and extracted 3 times with ethyl acetate. The extract is washed with water, dried over anhydrous magnesium sulfate, and evaporated to give 8.77 g of residue. The residue is refined by column chromatography (silica gel 200 g, benzene:ethyl acetate (30:1)) to provide 5.911 g of the compound 11 as an oil (94% yield).

(2) From the hydroxy-lactam 6

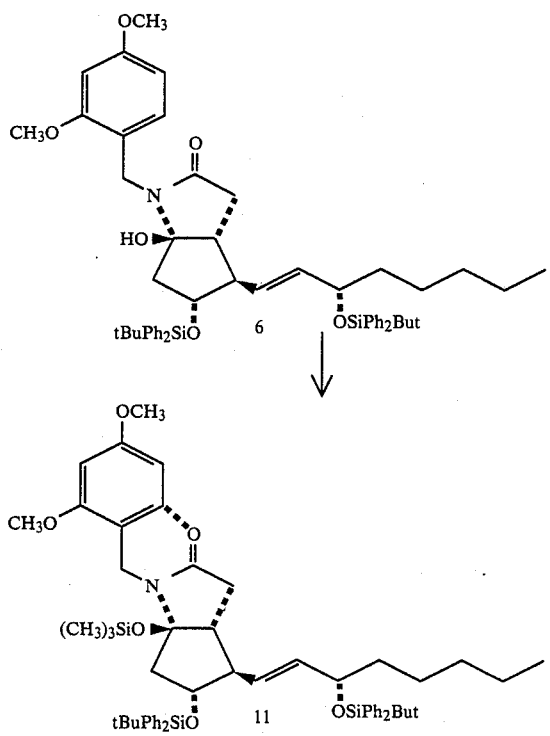

To a solution of 50 mg (0.055 mmol) of the hydroxy-lactam 6 (Example I-4) dissolved in 1 ml of a mixture of dry dichloromethane and dry pyridine (1:1) are added 68 mg (0.556 mmol) of 4-dimethylaminopyridine and 30 mg (0.277 mmol) of trimethylsilyl chloride in a nitrogen atmosphere and the mixture is stirred for 2 hrs on an oil bath at 70° C. Then, the reaction mixture is treated in the same manner as in Example I-9-(1) to give 64 mg of the residue, which is purified by column chromatography (3 g of silica gel; eluted with benzene:ethyl acetate=30:1) to give 54 mg of the compound 11 (quantitative yield).

MS: m/z 981 (M+), m/z 924 (M+−tBu).

[α]$_D$+11.0±1.0° (20° C., c=0.510, CHCl$_3$).

IR: νmax (CHCl$_3$) 3072, 3004, 1682, 1615, 1591, 1507, 1113, 842 cm$^{-1}$.

NMR: δppm (CDCl$_3$) −0.14 (9H, s), 0.79 (3H), 0.93 (9H, s), 1.05 (9H, s), 3.68 (3H, s), 3.73 (3H, s), 3.90 (1H, m), 4.13 (1H, m), 4.26 (1H, d, J=15 Hz), 4.39 (1H, d, J=15 Hz), 5.41 (2H, m), 6.36 (2H, m), 7.1–7.75 (21H, m).

Example I-10

Preparation of N-(2,4-dimethoxybenzyl)-1-phenylthio-2-aza-3-oxo-6-[(3S)-3-tert-butyldiphenylsilyloxyoct-1-enyl]-7-tert-butyldiphenylsilyloxybicyclo[3.3.0]octane 12a

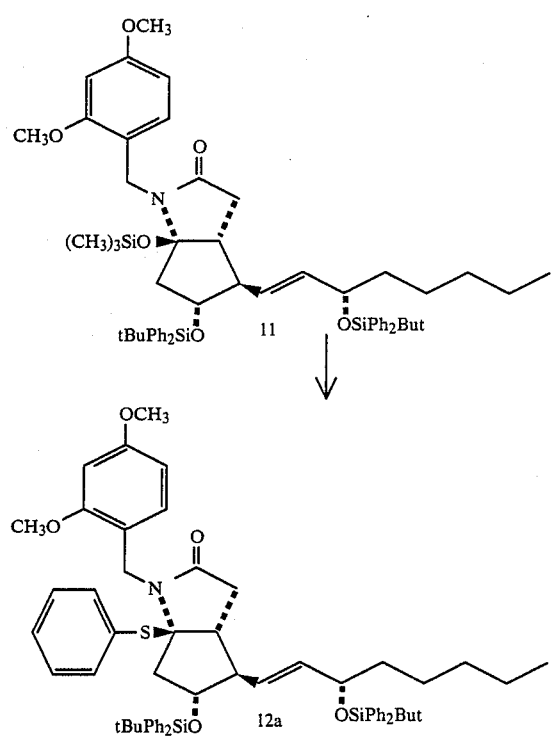

To a solution of 2.02 g (2.06 mmol) of the trimethylsilyloxylactam 11 (Example I-9) in 20 ml of dry ethyl ether are added 1.18 g (10.71 mmol) of thiophenol and 0.2 ml of 3N ethyl ether solution of hydrogen chloride in a nitrogen atmosphere, and the mixture is stirred at room temperature for 45 minutes. The reaction mixture is neutralized with powder sodium hydrogencarbonate and evaporated. The residue is purified by column chromatography (Lober column size B (two columns); eluted with cyclohexane:ethyl acetate=5:1) to give 1.83 g of the compund 12a as a foamy material (89% yield).

MS: m/z 944 (M+−tBu), m/z 892 (M+−PhS).

[α]$_D$+42.2±1.6° (20° C., c=0.51, CHCl$_3$).

IR: νmax (CHCl$_3$) 3072, 3004, 1682, 1615, 1591, 1508, 1112 cm$^{-1}$.

NMR: δppm (CDCl$_3$) 0.77 (3H), 0.92 (9H, s), 1.04 (9H, s), 3.71 (3H, s), 3.75 (3H, s), 4.05 (2H, m), 4.61 (1H, d, J=15 Hz), 4.75 (1H, d, J=15 Hz), 5.40 (2H, m), 6.43 (2H, m), 7.1–7.7 (26H, m).

Example I-11

Preparation of N-(2,4-dimethoxybenzyl)-1-ethyl-2-aza-3-oxo-6-[(3S)-3-tert-butyldiphenylsilyloxyoct-1-enyl]-7-tert-butyldiphenylsilyloxybicyclo[3.3.0]octane 12d

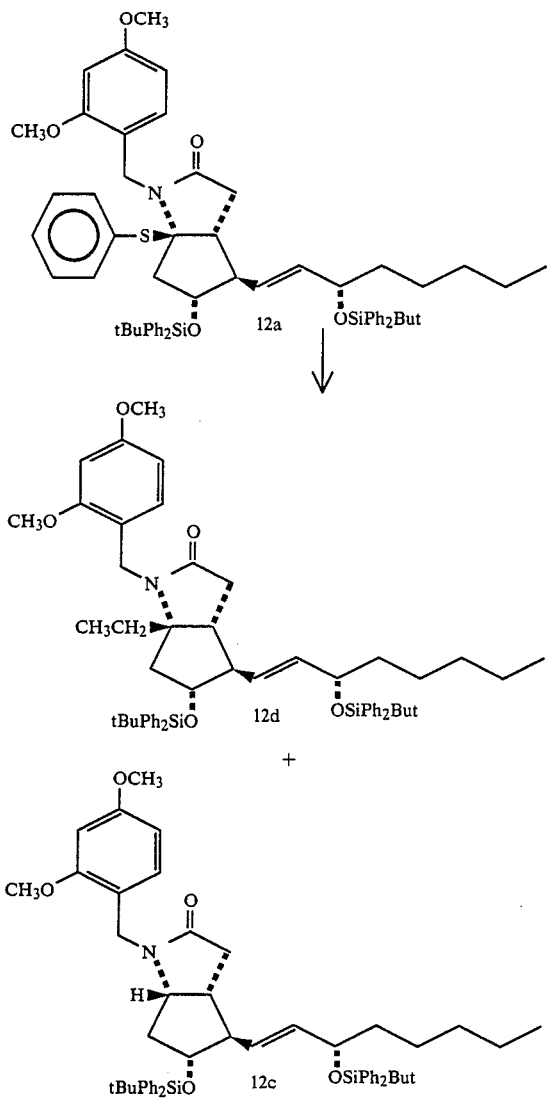

In an atmosphere of argon, 185 mg (0.185 mmol) of the phenylthio-lactam 12a (Example I-10) is dissolved in 7 ml of dry chloroform and 1 ml (2 mmol) of 2M n-hexane solution of diethyl zinc is added thereto, and then the mixture is stirred in a tightly closed vessel on an oil bath at 80° C. for 2 hours. After cooling, the reaction mixture is poured into iced water and a saturated aqueous solution of ammonium chloride is added. The mixture is extracted 3 times with dichloromethane and the extract is washed with water, dried over anhydrous magnesium sulfate, and evaporated to give 204 mg of residue, which is purified by column chromatography (Lober column size B; eluted with cyclohexane:ethyl acetate=3:1) to give 109 mg of the compound 12d as an oil (64% yield) and 57 mg of N-(2,4-dimethoxybenzyl)-2-aza-3-oxo-6-[(3S)-3-tert-butyldiphenylsilyloxyoct-1-enyl]-7-tert-butyldiphenylsilyloxybicyclo[3.3.0]octane 12c as an oil (34.5% yield).

Compound 12d
MS: m/z 922 (MH+), m/z 864 (M+ −tBu).
$[\alpha]_D$+7.5±0.8° (20° C., c=0.610, CHCl$_3$).
IR: $\nu$max (CHCl$_3$) 3072, 3004, 1661, 1615, 1591, 1507, 1111 cm$^{-1}$.
NMR: δppm (CDCl$_3$) 0.40 (3H, t, J=7 Hz), 0.79 (3H), 0.94 (9H, s), 1.04 (9H, s), 3.68 (3H, s) 3.78 (3H, s), 3.80 (1H, m), 4.15 (1H, m), 4.22 (1H, d, J=15 Hz), 4.38 (1H, d, J=15 Hz), 5.40 (2H, m), 6.40 (2H, m), 7.15–7.8 (21H, m).

Compound 12c
MS: m/z 894 (MH+), m/z 836 (M+ −tBu).
$[\alpha]_D$−29.7±2.3° (20° C., c=0.30, CHCl$_3$).
IR: $\nu$max (CHCl$_3$) 3072, 3004, 1668, 1614, 1590, 1508, 1112 cm$^{-1}$.
NMR: δppm (CDCl$_3$) 0.79 (3H), 1.01 (18H, s), 3.52 (1H, m), 3.67 (3H, s), 3.76 (3H, s), 3.96 (1H, d, J=14.5 Hz), 4.00 (2H, m), 4.74 (1H, d, J=14.5 Hz), 5.27 (2H, m), 6.38 (2H, m), 7.05–7.8 (21H, m).

Example I-12

Preparation of N-(2,4-dimethoxybenzyl)-1-methyl-2-aza-3-oxo-6-[(3S)-3-tert-butyldiphenylsilyloxyoct-1-enyl]-7-tert-butyldiphenylsilyloxybicyclo[3.3.0]octane 12e

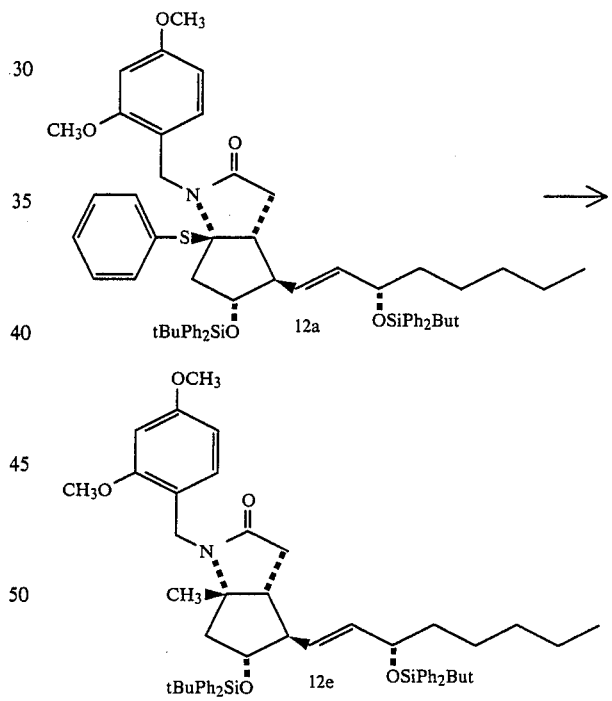

In an atmosphere of argon, 905 mg (0.904 mmol) of the compound 12a (Example I-10) is dissolved in 30 ml of dry chloroform and 30 ml (60 mmol) of 2M n-hexane solution of dimethyl zinc is added thereto, and then the mixture is stirred in a tightly closed vessel on an oil bath at 80° C. for 17 hours. After cooling, the reaction mixture is poured into iced water and a saturated aqueous solution of ammonium chloride is added. The mixture is extracted 3 times with dichloromethane and the extract is washed with water, dried over anhydrous magnesium sulfate, and evaporated to give 970 mg of residue, which is purified by column chromatography (Lober column size B; eluted with benzene:ethyl acetate=15:1)

to give 742 mg of the compound 12e as an oil (90.5% yield).

MS: m/z 908 (MH+), m/z 850 (M+ −tBu).

$[\alpha]_D$ −7.2±0.9° (20° C., c=0.557, CHCl$_3$).

IR: νmax (CHCl$_3$) 3072, 3004, 1663, 1615, 1591, 1507, 1113 cm$^{-1}$.

NMR: δppm (CDCl$_3$) 0.79 (3H), 0.88 (3H, s), 0.95 (9H, s), 1.03 (9H, s), 3.70 (3H, s), 3.75 (3H, s), 3.82 (1H, m), 4.12 (1H, m), 4.35 (2H, s), 5.35 (2H, m), 6.40 (2H, m), 7.1-7.8 (21H, m).

EXAMPLE I-13

Preparation of N-(2,4-dimethoxybenzyl)-1-trimethylsilylethynyl-2-aza-3-oxo-6-[(3S)-3-tert-butyldiphenylsilyloxyoct-1-enyl]-7-tert-butyldiphenylsilyloxybicyclo[3.3.0]octane 12f

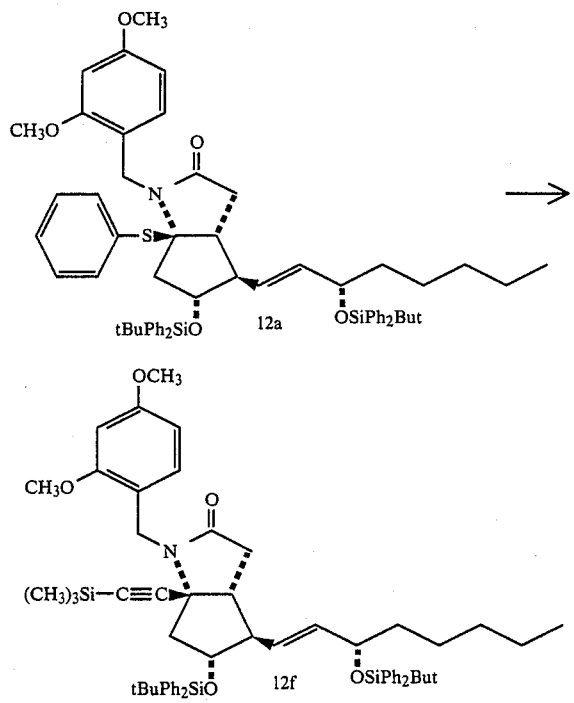

In an atmosphere of argon, 3.19 g (32.5 mmol) of trimethylsilylacetylene is dissolved in 45 ml of dry tetrahydrofuran and the solution is cooled in an ice water bath and 18 ml (30.6 mmol) of 1.7N n-hexane solution of n-butyl lithium is dropwise added in small portions thereto. The mixture is stirred at the same temperature for 30 minutes, then 0.68M tetrahydrofuran solution of zinc chloride is added to adjust it to around neutral (added about 32 ml), and the mixture is stirred at the same temperature for additional 15 minutes. Subsequently, the reaction vessel is tightly closed and the mixture stirred on an oil bath at 60° C. for 1 hour. The solvent is evaporated and to the residue is added a solution of 3.00 g (3.0 mmol) of the compound 12a (Example I-10) in 100 ml of dry xylene. The mixture is stirred in a tightly closed vessel on an oil bath at 140° C. for 30 minutes. After cooling, the reaction mixture is poured into a saturated aqueous solution of ammonium chloride and extracted 3 times with dichloromethane, and the extract is washed with water, dried over anhydrous magnesium sulfate, and evaporated to give 3.50 g of residue, which is purified by column chromatography (Lober column size C; eluted with benzene:ethyl acetate=20:1) to give 2.49 g of the compound 12f as an oil (84% yield).

MS: m/z 989 (M+), m/z 932 (M+ −tBu).

$[\alpha]_D$ −19.2±1.1° (20° C., c=0.562, CHCl$_3$).

IR: νmax (CHCl$_3$) 3072, 3004, 2164, 1675, 1615, 1591, 1508, 1112, 844 cm$^{-1}$.

NMR: δppm (CDCl$_3$) 0.03 (9H, s), 0.79 (3H), 0.97 (9H, s), 1.04 (9H, s), 3.70 (3H, s), 3.74 (3H, s), 4.00 (2H, m), 4.43 (1H, d, J=15 Hz), 4.54 (1H, d, J=15 Hz), 5.36 (2H, m), 6.33 (2H, m), 7.1-7.8 (21H, m).

Example I-14

Preparation of N-(2,4-dimethoxybenzyl)-1-propynyl-2-aza-3-oxo-6-[(3S)-3-tert-butyldiphenylsilyloxyoct-1-enyl]-7-tert-butyldiphenylsilyloxybicyclo[3.3.0]octane 12h

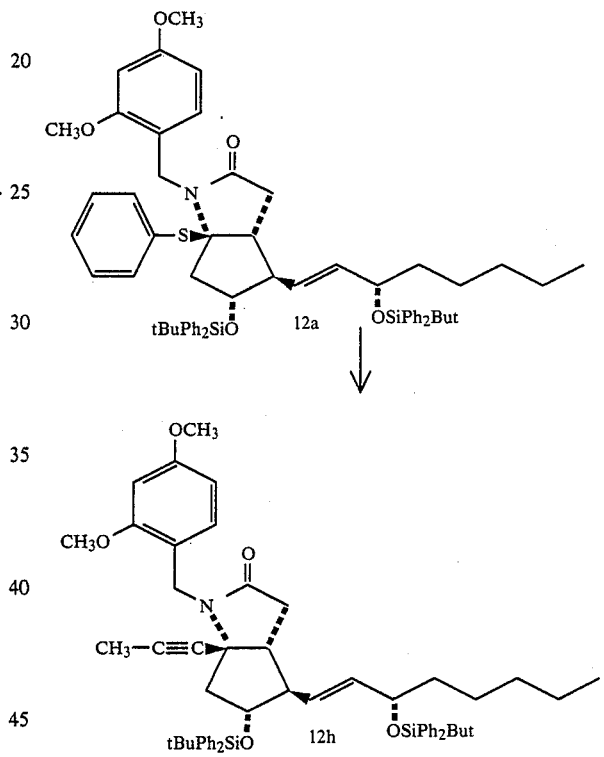

To a solution of 1.743 g (15.53 mmol) of 1-trimethylsilylpropyne in 25 ml of dry tetrahydrofuran is dropwise added 7.6 ml (12.16 mmol) of 1.6M ethyl ether solution of methyl lithium-lithium bromide complex in small portions in an atmosphere of argon, and the mixture is stirred at room temperature for 3 hours to become a white suspension. This suspension is cooled with ice water, and 0.69M tetrahydrofuran solution of zinc chloride is added in order to adjust it to around neutral (added about 15 ml). The mixture is stirred at the same temperature for 15 minutes to become a solution, which is then stirred in a tightly closed state on an oil bath at 60° C. for an hour, and then evaporated. To the residue is added a solution of 1.20 g (1.2 mmol) of the compound 12a (Example I-10) in 50 ml of dry xylene and the mixture is stirred in a tightly closed vessel on an oil bath at 140° C. for one and half hours. After cooling, the reaction mixture is poured into a saturated aqueous solution of ammonium chloride and extracted 3 times with dichloromethane, and the extract is washed with water, dried over anhydrous magnesium sulfate, and evaporated to give 1.61 g of residue, which is purified by column chromatography (Lober column size B (2 columns); eluted with benzene:ethyl acetate=20:1) to give 887 mg of the compound 12h as an oil (79.5% yield).

MS: m/z 931 (M+), m/z 874 (M+ −tBu).
$[\alpha]_D$ −18.8±1.1° (25° C., c=0.537, CHCl$_3$).
IR: $\nu$max(CHCl$_3$) 3072, 3004, 1673, 1615, 1591, 1508, 1113 cm$^{-1}$.
NMR: δppm (CDCl$_3$) 0.79 (3H), 0.94 (9H, s), 1.03 (9H, s), 1.58 (3H, s), 3.71 (3H, s), 3.75 (3H, s), 4.05 (2H, m), 4.46 (2H, s), 5.36 (2H, m), 6.37 (2H, m), 7.15–7.75 (21H, m).

Example I-15

Preparation of N-(2,4-dimethoxybenzyl)-1-phenylethynyl-2-aza-3-oxo-6-[(3S)-3-tert-butyldiphenylsilyloxyoct-1-enyl]-7-tert-butyldiphenylsilyloxybicyclo[3.3.0]octane 12i

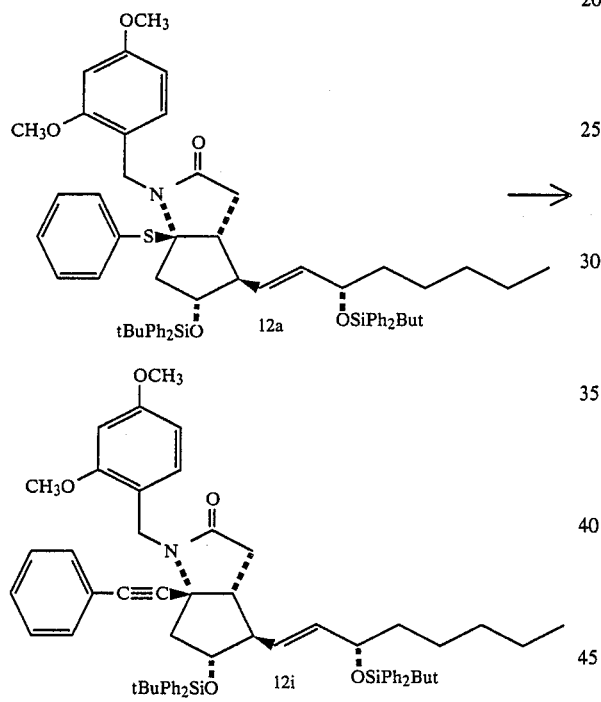

In an atmosphere of argon, 1.11 g (1.08 mmol) of phenylacetylene is dissolved in 2 ml of dry tetrahydrofuran, and the solution is cooled in an ice water bath, and then 0.64 ml (0.998 mmol) of 1.56N n-hexane solution of n-butyl lithium is dropwise added thereto. The mixture is stirred at the same temperature for 35 minutes, then 0.68M tetrahydrofuran solution of zinc chloride is added to adjust it to around neutral (added about 0.97 ml), and further, the mixture is stirred at the same temperature for 5 minutes. Then, the reaction mixture is stirred in a tightly closed state on an oil bath at 60° C. for about 1 hour. The solvent is evaporated and to the residue is added a solution of 100 mg (0.10 mmol) of the compound 12a (Example I-10) in 5 ml of dry xylene. The mixture is stirred in a tightly closed vessel on an oil bath at 140° C. for 30 minutes. After cooling, the reaction mixture is poured into a saturated aqueous solution of ammonium chloride and extracted with dichloromethane twice, and the extract is washed with water, dried over anhydrous magnesium sulfate, and evaporated to give 126 mg of residue, which is purified by column chromatography (Lober column size A; eluted with benzene:ethyl acetate=10:1) and thin layer chromatography (Merck, precoating plate, size 20×20, thickness 0.25 mm, 5 sheets; eluted with benzene:ethyl acetate=15:1) to give 85 mg of the compound 12i as a foamy material (85% yield).

MS: m/z 993 (M+), m/z 936 (M+ −tBu).
$[\alpha]_D$ −51.3±1.8° (24° C., c=0.518, CHCl$_3$).
IR: $\nu$max (CHCl$_3$) 3072, 3004, 1674, 1615, 1591, 1508, 1113 cm$^{-1}$.
NMR: δppm (CDCl$_3$) 0.77 (3H), 0.97 (9H, s), 1.01 (9H, s), 3.67 (3H, s), 3.70 (3H, s), 3.85–4.25 (2H, m), 4.55(2H, s), 5.40 (2H, m), 6.35 (2H, m), 7.05–7.8 (26H, m).

Example I-16

Preparation of 1-ethyl-2-aza-3-oxo-6-[(3S)-3-tert-butyldiphenylsilyloxyoct-1-enyl]-7-tert-butyldiphenylsiloxybicyclo[3.3.0]octane 10(S)d (1) From N-(2,4-dimethoxybenzyl)-1-ethyl-lactam 12d

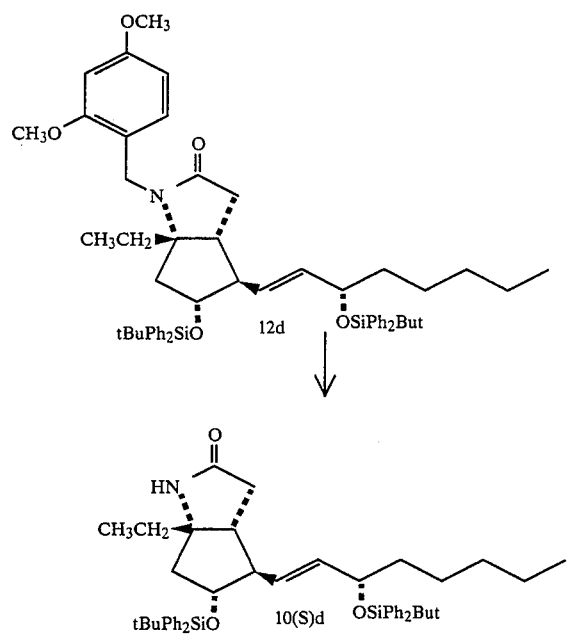

In 3 ml of a chloroform-water (19:1) mixture is dissolved 109 mg (0.118 mmol) of the N-benzyl-lactam 12d, and 55 mg (0.242 mmol) of 2,3-dichloro-5,6-dicyano-1,4-benzoquinone is added thereto. The mixture is refluxed by heating for 1 hour under stirring, then additional 55 mg (0.242 mmol) of 2,3-dichloro-5,6-dicyano-1,4-benzoquinone is added, and the mixture is refluxed by heating for additional 2 and half hours. After cooling, the reaction mixture is poured into water and extracted 3 times with dichloromethane, and the extract is washed with 1N sodium thiosulfate aqueous solution and with water successively, dried over anhydrous magnesium sulfate and evaporated to give 138 mg of residue, which is purified by column chromatography (Lober column, size A (2 columns); eluted with benzene:ethyl acetate=4:1) to give 58 mg of the compound 10(S)d as a foamy material (64% yield).

(2) From the 1-phenylthio-lactam 10(S)a

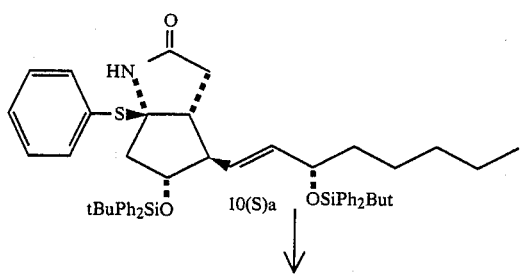

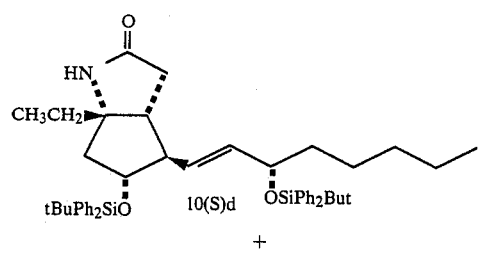

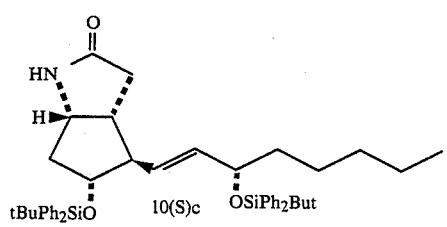

In the same manner as in Example I-11, 1.10 g of the phenylthio-lactam 10a is allowed to react with diethyl zinc to give foamy materials, that is, 548 mg of the compound 10(S)d (55% yield), 190 mg of 2-aza-3-oxo-6-[(3S)-3-tert-butyldiphenylsilyloxyoct-1-enyl]-7-tert-butyldiphenylsilyloxybicyclo[3.3.0]octane 10(S)c (20% yield), and 69 mg of the compound 8 (7% yield). In addition, the compound 10(S)c can also be prepared from the compound 12(S)c (Example I-11) on the reaction with 2,3-dichloro-5,6-dicyano-1,4-benzoquinon in chloroform-water (19:1) mixture by refluxing under heating.

Compound 10(S)d

MS: m/z 771 (M+), m/z 714 (M+ —tBu).

$[\alpha]_D$ —15.2±1.0° (25° C., c=0.533, CHCl3).

IR: $\nu$max (CHCl3) 3435, 3085, 3010, 1687, 1591, 1113 cm$^{-1}$.

NMR: δppm (CDCl3) 0.69 (3H, t, J=7 Hz), 0.80 (3H, s), 1.01 (9H, s), 1.04 (9H, s), 3.82 (1H, m), 4.12 (1H, m), 5.32 (2H, m), 6.66 (1H, s), 7.1–7.8 (20H, m).

Compound 10(S)c

MS: m/z 743 (M+), m/z 686 (M+ —tBu).

IR: $\nu$max (CHCl3) 3440, 3080, 3005, 1688, 1591, 1112 cm$^{-1}$.

NMR: δppm (CDCl3) 0.80 (3H), 1.03 (18H, s), 3.83 (2H, m), 4.10 (1H, m), 5.27 (2H, m), 6.76 (1H, s), 7.2–7.8 (20H, m).

Example I-17, 18-(1), 19, and 20

Removal of the benzyl group carried out in the same manner as in Example I-16-(1) affords the compounds shown in Table 1.

Example I-18-(2)

Preparation of 1-trimethylsilylethynyl-2-aza-3-oxo-6-(3-tert-butyldiphenylsilyloxyoct-1-enyl)-7-tert-butyldiphenylsilyloxybicyclo[3.3.0]octane 10(S)f From 1-phenylthio-lactam 10(S)a

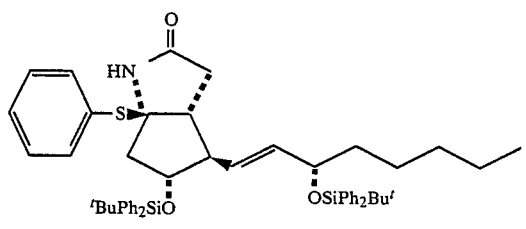

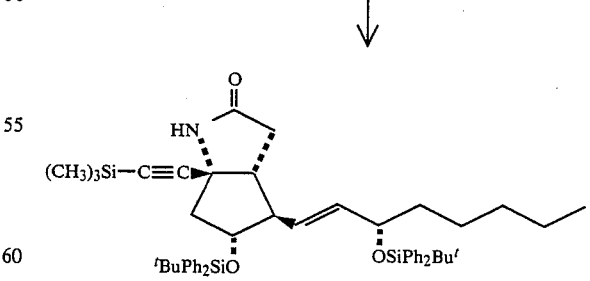

The substitution reaction carried out in the same manner as in Example I-13 affords the trimethylsilylethynyl-lactam 10(S)f in 86% yield.

TABLE 1

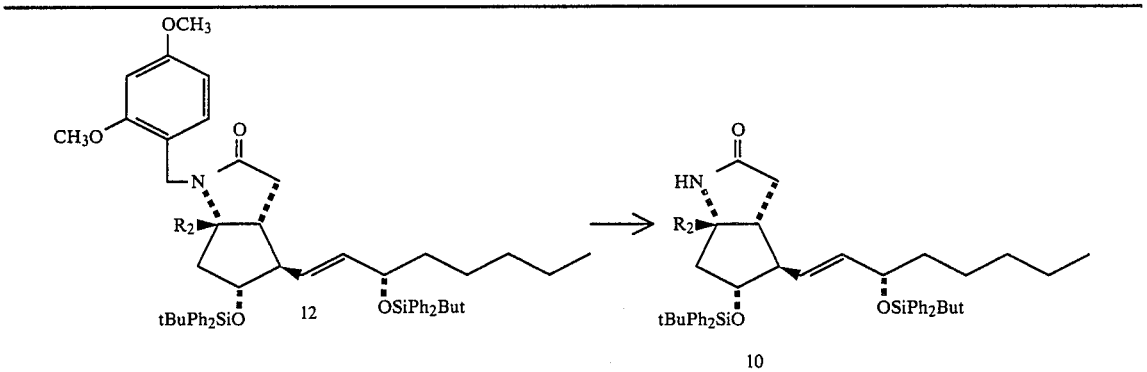

| Ref. Ex. No. | Compd. Number | R₂ | Yield (%) | MS m/z | Specific Rotation [α]$_D$ | IR νmax IR [cm$^{-1}$] | NMR δppm |
|---|---|---|---|---|---|---|---|
| 17 | 10e | —CH₃ | 63 | 757 (M⁺) 700 (M⁺—tBu) | −10.0 ± 1.0° (22° C., c = 0.514, CHCl₃) | (CHCl₃) 3428, 3072, 3004, 1686, 1590, 1112 | (CDCl₃) 0.80 (3H), 1.01 (9H,s), 1.03 (9H,s), 3.85 (1H,m), 4.08 (1H,m), 5.30 (2H,m), 6.11 (1H,s), 7.2~7.7 (20H,m) |
| 18-(1) | 10f | —C≡C—Si(CH₃)₃ | 67 | 782 (M⁺—tBu) | 0.0° (20° C., c = 0.513, CHCl₃) | (CHCl₃) 3432, 3072, 3004, 2160, 1697, 1590, 1112, 844 | (CDCl₃) 0.09 (9H,s), 0.80(3H), 1.00 (9H,s), 1.03 (9H,s), 4.05 (2H,m), 5.30 (2H,m), 6.17 (1H,s), 7.15~7.8 (20H,m) |
| 19 | 10h | —C≡C—CH₃ | 53 | 782 (MH⁺) 724 (M⁺—tBu) | −5.2 ± 0.9° (21° C., c = 0.500, CHCl₃) | (CHCl₃) 3432, 3072, 3004, 1693, 1590, 1111 | (CDCl₃) 0.80 (3H), 1.01 (9H,s), 1.03 (9H,s), 1.71 (3H,s), 4.05 (2H,m), 5.31 (2H,m), 6.06 (1H,s), 7.25~7.75 (20H,m) |
| 20 | 10i | —C≡C—C₆H₅ | 47 | 844 (MH⁺) 786 (M⁺—tBu) | +2.3 ± 0.8° (24° C., c = 0.515, CHCl₃) | (CHCl₃) 3432, 3072, 3004, 1698, 1591, 1112 | (CDCl₃) 0.78 (3H), 1.04 (18H,s), 3.9~4.2 (2H,m), 5.33 (2H,m), 6.82 (1H,s), 7.05~7.75(25H,m) |

Example I-21

Preparation of N-(2,4-dimethoxybenzyl)-1-(4-trimethylsilyl-1,3-butadiynyl)-2-aza-3-oxo-6-[(3S)-3-tert-butyldiphenyl-silyloxyoct-1-enyl]-7-tert-butyldiphenylilsyloxybicyclo[3.3.0]octane 12j

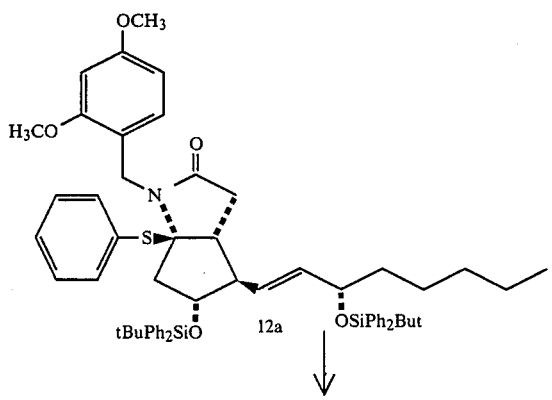

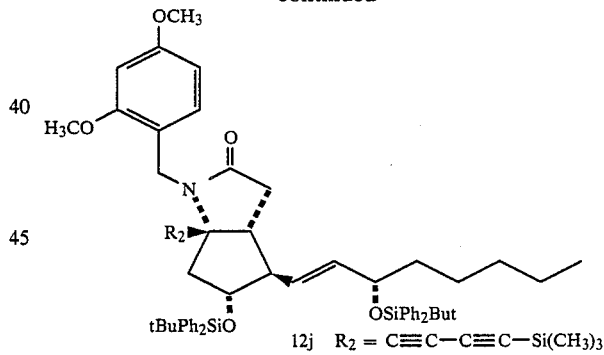

12j R₂ = C≡C—C≡C—Si(CH₃)₃

To a solution of 2.94 g (15.12 mmol) of 1,4-bis(trimethylsilyl)-1,3-butadiyne in 25 ml of dry tetrahydrofuran is dropwise added 7.6 ml (12.16 mmol) of 1.6M ethyl ether solution of methyl lithium-lithium bromide complex in small portions in an atmosphere of argon and the mixture is stirred at room temperature for 3 hours. After cooling in an ice water bath, the reaction mixture is adjusted to around neutral with 0.68M tetrahydrofuran solution of zinc chloride (added about 15.5 ml). The mixture is stirred in a tightly closed vessel on an oil bath at 60° C. for 1 hour and evaporated. A solution of 1.20 g (1.2 mmol) of the compound 12a (Example I-10) in 50 ml of dry xylene is added to the residue and the mixture is stirred in a tightly closed state on an oil bath at 140° C. for 2 hours. After cooling, the reaction mixture is poured into a saturated aqueous solution of ammonium chloride and extracted 3 times with dichloromethane. The extract is washed with water, dried over anhydrous magnesium sulfate and evaporated to give 1.894 g of a residue, which is purified by column chromatography (Lober column size B (2 columns); eluted with benzene:ethyl acetate=30:1) to give 952 mg of the compound 12j as a foamy material (78.5% yield).

MS: m/z 1014(MH+), m/z 956(M+−tBu).

$[\alpha]_D$ −71.4±2.2° (23° C., c=0.510, CHCl$_3$).

IR: νmax(CHCl$_3$) 3072, 3004, 2220, 2100, 1679, 1615, 1591, 1508, 1113, 845 cm$^{-1}$.

NMR: δppm(CDCl$_3$) 0.15(9H, s), 0.80(3H), 0.96(9H, s), 1.04(9H, s), 3.72(3H, s), 3.76(3H, s), 3.85–4.2(2H, m), 4.49(2H, s), 5.32(2H, m), 6.37(2H, m), 7.15–7.8(21H, m).

Example I-22

Preparation of 1-(4-trimethylsilyl-1,3-butadiynyl)-2-aza-3-oxo-6-[(3S)-3-tert-butyldiphenylsilyloxyoct-1-enyl]-7-tert-butyldiphenylsilyoxybicyclo[3.3.0]octane 10(S)j

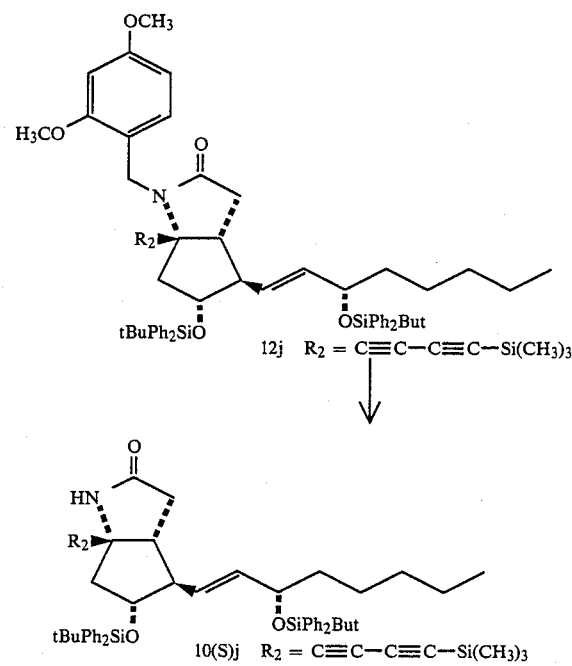

Removal of the benzyl group carried out in the same manner as in Example I-16-(1) using 2,3-dichloro-5,6-dicyano-1,4-benzoquinon affords 563 mg of the compound 10(S)j as a foamy material in 69.5% yield from 948 mg of N-benzyl-lactam 12j (Example I-21).

MS: m/z 806(M+−tBu).

$[\alpha]_D$ −7.9±1.0° (25° C., c=0.500, CHCl$_3$).

IR: νmax(CHCl$_3$) 3428, 3072, 3004, 2224, 2100, 1698, 1590, 1112, 845 cm$^{-1}$.

NMR: δppm(CDCl$_3$) 0.17(9H, s), 0.81(3H), 1.00(9H, s), 1.03(9H, s), 4.00(2H, m), 5.23(2H, m), 6.40(1H, s), 7.2–7.7(20H, m).

Example I-23

Preparation of 1-cyano-2-aza-3-oxo-6-[(3S)-3-tert-butyldiphenylsilyloxyoct-1-enyl]-7-tert-butyldiphenylsiloxybicyclo[3.3.0]octane 10(S)m

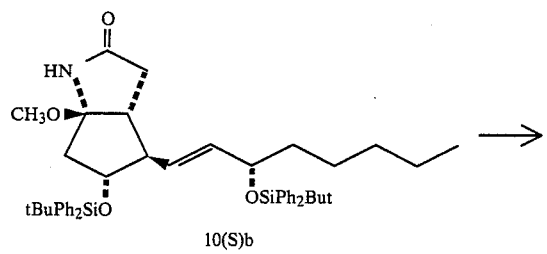

In an atmosphere of nitrogen, 900 mg (1.154 mmol) of 1-methoxy-2-aza-3-oxo-6-[(3S)-3-tert-butyldiphenylsilyloxyoct-1-enyl]-7-tert-butyldiphenylsilyloxybicyclo[3.3.0]octane 10(S)b (Example I-8) is dissolved in 45 ml of dry dichloromethane, 744 mg (7.50 mmol) of cyanotrimethylsilane and 58 mg (0.41 mmol) of boron trifluoride etherate are added thereto, and the mixture is stirred at room temperature for 4 hours. A dilute aqueous solution of sodium hydrogencarbonate is added to the reaction mixture, which is then extracted 3 times with dichloromethane. The extract is washed with water, dried over anhydrous magnesium sulfate, and evaporated to give 960 mg of residue, which is purified by column chromatography (Merck; Lober column, size B; eluted with benzene:ethyl acetate=10:1) to give 660 mg of the compound 10(S)m as a foamy material (74% yield).

MS: m/z 768(M+), m/z 711 (M+−$^t$Bu).

$[\alpha]_D^{23.5}$ −13.5±1.0° (c=0.512, CHCl$_3$).

IR: $\nu_{max}^{CHCl_3}$ 3428, 2240, 1713, 1591, 1113 cm$^{-1}$.

NMR: $\delta_{ppm}^{CDCl_3}$ 0.81 (3H), 1.00 (9H, s), 1.03 (9H, s), 4.00 (2H, m), 5.07 (1H, dd, J=15.5, 6.5 Hz), 5.33 (1H, dd, J=15,5, 5.5 Hz), 7.04 (1H, s), 7.15–7.7 (20H, m).

Example I-24

Preparation of 1-ethynyl-2-aza-3-oxo-6-[(3S)-3-tert-butyldiphenylsilyloxyoct-1-enyl]-7-tert-butyldiphenylsilyloxybicyclo[3.3.0]octane 10(S)g

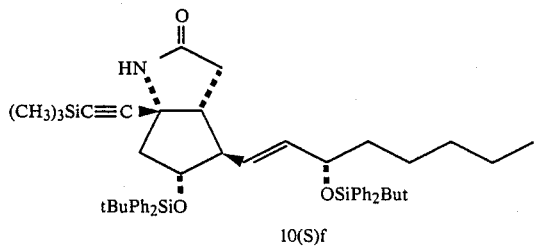

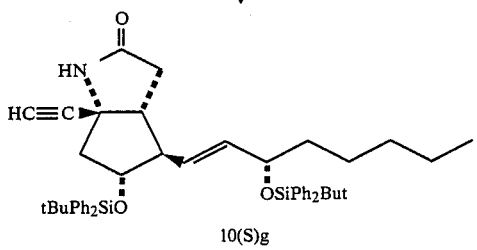

10(S)g

In an atmosphere of nitrogen, 689 mg of 1-trimethylsilylethynyl-2-aza-3-oxo-6-[(3S)-3-tert-butyldiphenylsilyloxyoct-1-enyl]-7-tert-butyldiphenylsilyloxybicyclo[3.3.0]octane 10(S)f [Example I-18-(2)] is dissolved in 20 ml of dry methanol, then 20 mg of anhydrous potassium carbonate is added thereto, and the mixture is stirred at room temperature for 3 hours and 50 minutes.

Water is added to the reaction mixture which is then extracted 3 times with dichloromethane. The extract is washed with water, dried over anhydrous magnesium sulfate, and evaporated to give 630 mg of residue, which is purified by column chromatography (20 g of silica gel; eluted with benzene:ethyl acetate=10:1) to give 618 mg of the compound 10(S)g as a foamy material (98% yield).

MS: m/z 767 (M+), m/z 710 (M+−$^t$Bu).
$[\alpha]_D^{25}$ −7.3±0.9° (c=0.514, CHCl$_3$).
IR: $\nu_{max}^{CHCl_3}$ 3432, 3312, 1698, 1590, 1112 cm$^{-1}$.
NMR: $\delta_{ppm}^{CDCl_3}$ 0.81 (3H), 1.01 (9H, s), 1.03 (9H, s), 2.30 (1H, s), 4.05 (2H, m), 5.28 (2H, m), 6.40 (1H, s), 7.2–7.75 (20H, m).

Example I-25

Preparation of 1-ethenyl-2-aza-3-oxo-6-[(3S)-3-tert-butyldiphenylsilyloxyoct-1-enyl]-7-tert-butyldiphenylsilyloxybicyclo[3.3.0]octane 10(S)l

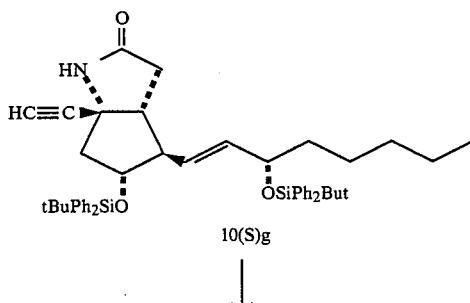

10(S)g

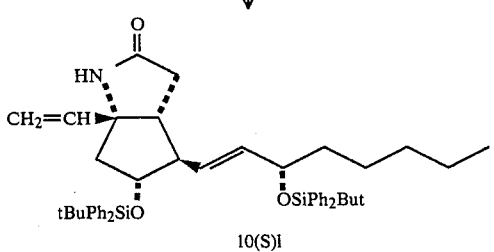

10(S)l

To a suspension of 507 mg (Example I-24) of the ethynyl-lactam 10(S)g in 50 ml of benzene are added 0.5 ml of quinoline and 25 mg of 5% palladium-barium sulfate and the mixture is stirred in an atmosphere of hydrogen at ordinary temperature and atmospheric pressure for 55 minutes. The insoluble material is removed by filtration and the filtrate is evaporated. The residue is dissolved in ethyl acetate and the resulting mixture is successively washed with 1N hydrochloric acid, water, dilute aqueous solution of sodium hydrogencarbonate, and water, dried over anhydrous magnesium sulfate, and evaporated to give 524 mg of residue, which is purified by column chromatography (Lober column, size B; eluted with benzene:ethyl acetate=5:1) to give 466 mg of the compound 10(S)l as a foamy material (91.5% yield).

MS: m/z 769 (M+), m/z 712 (M+−$^t$Bu).
$[\alpha]_D^{23}$ −23.1±1.2° (c=507, CHCl$_3$).
IR: $\nu_{max}^{CHCl_3}$ 3432, 1694, 1590, 1111 cm$^{-1}$.
NMR: $\delta_{ppm}^{CDCl_3}$ 0.80 (3H), 1.03 (18H, s), 3.8–4.2 (2H, m), 4.85 (1H, d, J=10.5 Hz), 4.91 (1H, d, J=17 Hz), 5.29 (2H, m), 5.57 (1H, dd, J=10.5, 17 Hz), 6.26 (1H, s), 7.2–7.75 (20H, m).

Example I-26

Preparation of 1-cyano-2-aza-3-thioxo-6-[(3S)-3-tert-butyldiphenylsilyloxyoct-1-enyl]-7-tert-butyldiphenylsilyloxybicyclo[3.3.0]octane 13(S)m

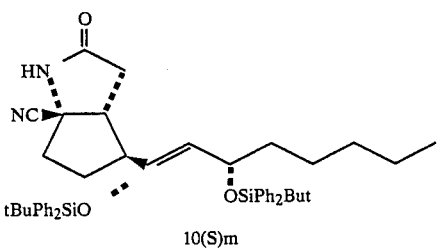

10(S)m

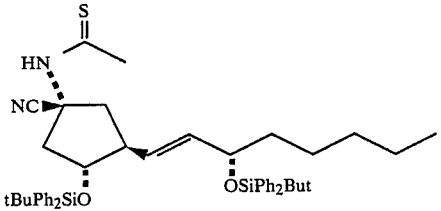

13(S)m

To a solution of 684 mg (0.89 mmol) of the cyano-lactam 10(S)m (Example-23) in 40 ml of dry benzene are added 2.84 g (35.85 mmol) of pyridine and 1.80 g (4.55 mmol) of Lawesson's Reagent in an atmosphere of nitrogen and the mixture is stirred on an oil bath at 70° C. for 1 hour and 45 minutes. After cooling, the reaction mixture is directly purified by column chromatography (70 g of silica gel; eluted with benzene) to give 637 mg of the compound 13(S)m as a foamy material (91% yield).

MS: m/z 784 (M+), m/z 727 (M+−$^t$Bu).
$[\alpha]_D^{23.5}$ −14.7±1.1° (c=0.510, CHCl$_3$).
IR: $\nu_{max}^{CHCl_3}$ 3400, 2240, 1591, 1472, 1113 cm$^{-1}$.
NMR: $\delta_{ppm}^{CDCl_3}$ 0.82 (3H), 1.03 (18H, s), 4.03 (2H, m), 5.05 (1H, dd, J=15.5, 6.5 Hz), 5.32 (1H, dd, J=5.5, 5.5 Hz), 7.15–7.7 (20H, m), 8.24 (1H, s).

Example I-27

Preparation of 1-ethenyl-2-aza-3-thioxo-6-[(3S)-3-tert-butyldiphenyl-silyloxyoct-1-enyl]-7-tert-butyldiphenylsilyloxybicyclo[3.3.0]octane 13(S)l

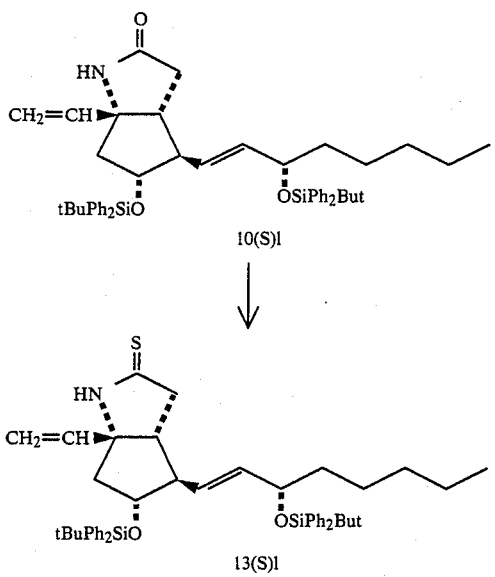

In the same manner as in Example I-26, 419 mg of the ethenyllactam 10(S)l (Example I-25) is allowed to react to give 423 mg of the compound 13(S)l as a foamy material (99% yield).

MS: m/z 785 (M+), m/z 728 (M+ — $^t$Bu).
$[\alpha]_D^{23}$ −11.8±1.0° (c=0.502, CHCl$_3$).
IR: $\nu_{max}^{CHCl_3}$ 3400, 1590, 1485, 1112 cm$^{-1}$.
NMR: $\delta_{ppm}^{CDCl_3}$ 0.80 (3H), 1.04 (18H, s), 3.8–4.2 (2H, m), 4.90 (1H, d, J=17.5 Hz), 4.92 (1H, d, J=10 Hz), 5.27 (2H, m), 5.56 (1H, dd, J=17.5 10 Hz), 7.2–7.75 (20H, m), 8.00 (1H, s).

Example I-28

Preparation of 2-oxa-3-oxo-6-tert-butyldiphenylsilyloxymethyl-7-tert-butyldiphenylsilyloxybicyclo[3.3.0]octane 22

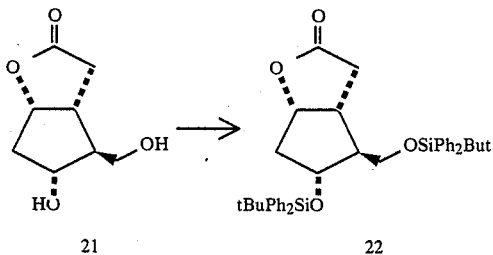

In an atmosphere of nitrogen, 11.40 g (66.21 mmol) of (1S,5R,6S,7R)-2-oxa-3-oxo-6-hydroxymethyl-7-hydroxybicyclo[3.3.0]octane 21 is dissolved in 140 ml of dry N,N-dimethylformamide and 28.32 g (231.7 mmol) of 4-dimethylaminopyridine and 45.59 g (165.5 mmol) of tert-butyldiphenyl silyl chloride are added to the above solution, and the mixture is allowed to stand at room temperature for 2 days. The reaction mixture is poured into iced water and extracted 3 times with ethyl acetate. The extract is washed with water, dried over anhydrous magnesium sulfate and evaporated. The residue is applied to column chromatography (100 g of silica gel; eluted with benzene-benzene:ethyl acetate=20:1) to give 50.48 g of the crude product as a pale yellow oil, (which may be applied to the following reaction without further purification). A portion (about 240 mg) of the crude product 22 is purified by thin layer chromatography (Merck; precoated plate, size 20×20 cm, thickness 0.5 mm, 10 sheets; developed with n-hexane:ethyl acetate=4:1) to give 179 mg of the compound 22 as a foamy material, of which portion is recrystallized from n-pentane to give crystals, mp. 79°–81° C.

MS: m/z 591 (M+ — $^t$Bu).
$[\alpha]_D^{22}$ −20.7±1.3° (c=0.483, CHCl$_3$).
IR: $\nu_{max}^{CHCl_3}$ 1769, 1592, 1114, 1087 cm$^{-1}$.
NMR: $\delta_{ppm}^{CDCl_3}$ 0.97 (9H, s), 1.02 (9H, s), 3.40 (2H, m), 4.10 (1H, m), 4.78 (1H, m), 7.15–7.75 (20H, m).

Example I-29

Preparation of N-(2,4-dimethoxybenzyl)-(1-tert-butyldiphenylsilyloxy-2-tert-butyldihenylsilyloxymethyl-4-hydroxycyclopent-3-yl)-acetoamide 23

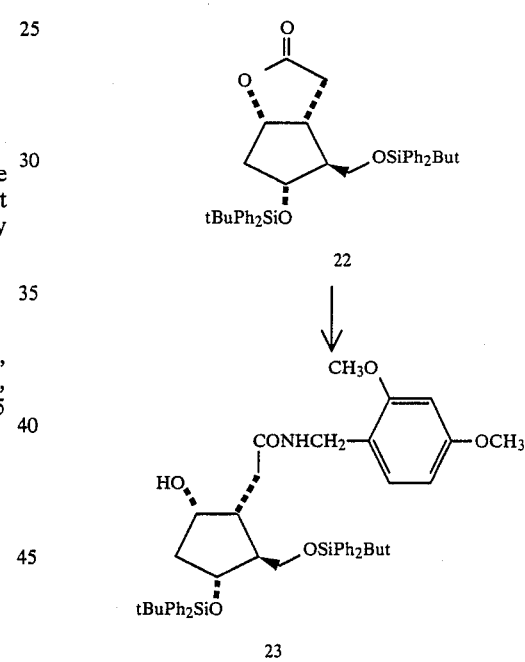

In an atmosphere of nitrogen, a mixture of 50.24 g (66.21 mmol) of the lactone 22 (Example I-28), 2.52 g (24.68 mmol) of 2-hydroxypyridine, and 44.2 g (264.2 mmol) of 2,4-dimethoxybenzylamine is stirred on an oil bath at 100° C. for 3 hours and 30 minutes, and further, allowed to stand at room temperature overnight. A saturated aqueous solution of sodium chloride and dichloromethane are added to the reaction mixture. After acidified with 1N hydrochloric acid, the mixture is extracted 3 times with dichloromethane. The extract is washed with a saturated aqueous solution of sodium chloride, dried over anhydrous magnesium sulfate, and evaporated to give 59.9 g of residue, which is purified by column chromatography (350 g of silica gel; eluted with benzene-benzene:ethyl acetate=4:1) to give 50.18 g of the crude product 23 as an oil (93% yield).

A portion of the crude product (about 230 mg) is further purified by thin layer chromatography (Merck;

precoated plate, size 20 cm×20 cm, thickness 0.5 mm, 8 1 sheets; eluted with benzene:ethyl acetate=4:1) to give 208 mg of the compound 23 as a foamy material.

MS:m/z 815 (M+), m/z 758 (M+−$^t$Bu).
$[\alpha]_D^{22}$+6.5±0.9° (c=0.520, CHCl$_3$).
IR:$\nu_{max}^{CHCl_3}$ 3504, 3452, 2656, 1617, 1592, 1509, 1114, 1037 cm$^{-1}$.
NMR:$\delta_{ppm}^{CDCl_3}$ 0.92 (9H, s), 1.01 (9H, s), 3.41 (2H, m), 3.76 (6H, s), 4.11 (2H, m), 4.32 (2H, m), 6.11 (1H, m), 6.40 (2H, m), 7.1–7.75 (21H, m).

Example I-30

Preparation of N-(2,4-dimethoxybenzyl)-(3-tert-butyldiphenylsilyloxymethyl-4-tert-butyldiphenylsilyloxycyclopentan-1-on-2-yl)-acetoamide 24 te=8:1) to give 172 mg of the compound 24 as a foamy material.

MS:m/z 813 (M+), m/z 756 (M+−$^t$Bu).
$[\alpha]_D^{22}$−27.9±1.4° (c=0.502, CHCl$_3$).
IR:$\nu_{max}^{CHCl_3}$ 3452, 1741, 1670, 1617, 1592, 1509, 1114, 1038 cm$^{-1}$.
NMR:$\delta_{ppm}^{CDCl_3}$ 0.97 (9H, s), 1.01 (9H, s), 3.6–3.95 (2H, m), 3.76 (6H, s), 4.15–4.45 (3H, m), 5.88 (1H, m), 6.40 (2H, m), 7.05–7.75 (21H, m).

Example I-31

Preparation of N-(2,4-dimethoxybenzyl)-1-trimethylsilyloxy-2-aza-3-oxo-6-tert-butyldiphenylsilyloxymethyl-7-tert-butyldiphenylsilyloxybicyclo[3.3.0]octane 25

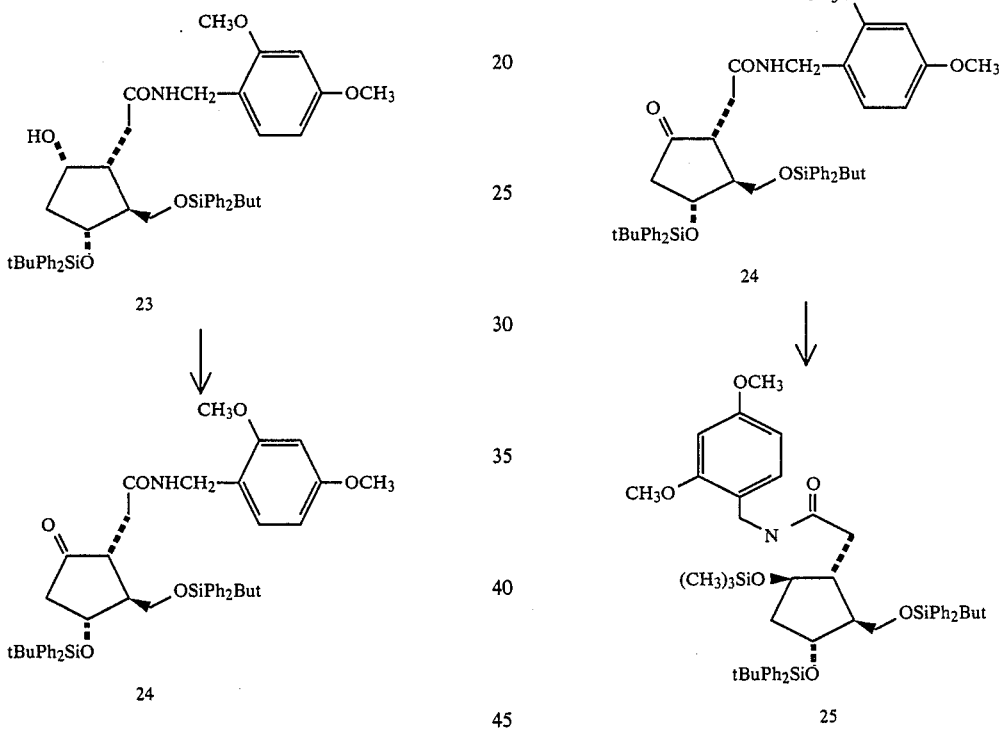

In an atmosphere of nitrogen, a solution of 19.4 g (152.8 mmol) of oxalyl chloride in 200 ml of dry dichloromethane is cooled to −60° C. and a solution of 23.92 g (306.7 mmol) of dimethylsulfoxide in 100 ml of dry dichloromethane is added dropwise thereto over 25 minute period under stirring. The mixture is stirred at the same temperature for 5 minutes. A solution of 49.95 g(61.2 mmol) of the alcohol 23 (Example I-29) and 30.88 g (305.8 mmol) of triethylamine in 300 ml of dry dichloromethane is added dropwise to the reaction mixture over a 1 hour and 10 minute period and the resulting mixture is further stirred at the same temperature for 50 minutes. After the temperature of the reaction mixture is brought to room temperature, iced water is added. The mixture is acidified with 1N hydrochloric acid and extracted 3 times with dichloromethane. The extract is washed with water, dried over anhydrous magnesium sulfate, and evaporated to give 48.7 g of the crude product 24 as a foamy material (97.5% yield). This may be applied to the following reaction without further purification. A portion of crude product 24 (about 200 mg) is purified by column chromatography (Lobar column, size A, 2 columns; eluted with benzene:ethyl aceta- In an atmosphere of nitrogen, 48.5 g (59.58 mmol) of the keto-amide 24 (Example I-30) is dissolved in 360 ml of dry dichloromethane and dry pyridine (1:1) mixture and 29.12 g (238.3 mmol) of 4-dimethylaminopyridine and 12.95 g (119.2 mmol) of trimethylsilyl chloride are added thereto. The mixture is stirred on an oil bath at 70° C. for 1 hour and 20 minutes. After cooling, the reaction mixture is poured into ice water and extracted 3 times with dichloromethane. The extract is washed with water, dried over anhydrous magnesium sulfate, and evaporated to give 75 g of a residue, which is purified by column chromatography (250 g of silica gel; eluted with benzene-benzene:ethyl acetate=15:1) to give 49.1 g of the product 25 (93% yield). A portion of the product 25 is recrystallized from ethyl ether-n-pentane to give crystals, mp. 113.5°–115.5° C.

MS:m/z 885 (M+), m/z 828 (M+−$^t$Bu).
$[\alpha]_D^{22}$+3.0±0.9° (c=0.500, CHCl$_3$).
IR:$\nu_{max}^{CDCl_3}$ 1683, 1617, 1592, 1509, 1114, 1086 844 cm$^{-1}$.
NMR:$\delta_{ppm}^{CDCl_3}$ −0.15 (9H, s), 0.91 (9H, s), 1.01 (9H, s), 3.45–3.85 (2H, m), 3.69 (3H, s), 3.75 (3H, s), 3.9–4.2

(1H, m), 4.26 (1H, d, J=15 Hz), 4.43 (1H, d, J=15 Hz), 6.40 (2H, m), 7.05–7.7 (21H, m).

Example I-32

Preparation of N-(2,4-dimethoxybenzyl)-1-phenylthio-2-aza-3-oxo-6-tert-butyldiphenylsilyloxymethyl-7-tert-butyldiphenylsilyloxybicyclo[3.3.0]octane 26a

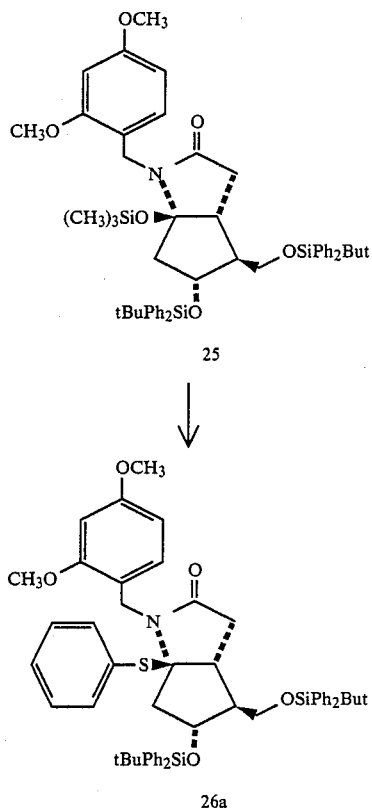

To a solution of 48.89 g (55.17 mmol) of the trimethylsilyloxy-lactam 25 (Example I-31) in 500 ml of dry ethyl ether are added 34.33 g (3.11 mmol) of the thiophenol and 5 ml of 3N ethyl ether solution of hydrogen chloride in an atmosphere of nitrogen and the mixture is stirred at room temperature for 1 hour and 35 minutes. The reaction mixture is neutralized with powdery sodium hydrogencarbonate and evaporated. The residue is applied to column chromatography (300 g of silica gel, eluted with benzene-ethyl acetate) to give 50 g of crystals, which are recrystallized from ethyl ether-n-pentane to give 40.57 g of the crystals 26a, mp. 133°–135° C. (81% yield). A portion of the crystals are further recrystallized from ethyl ether-n-pentane to give the crystals 26a, mp. 134.5°–136° C.

MS:m/z 848 (M+ −$^t$Bu), m/z 796 (M+ −PhS).

$[\alpha]_D^{22}$24.1±1.3° (c=0.507, CHCl$_3$).

IR:$\nu_{max}^{CHCl_3}$ 1682, 1617, 1592, 1509, 1114 cm$^{-1}$.

NMR:$\delta_{ppm}^{CDCl_3}$ 0.92 (9H, s), 1.01 (9H, s), 3.45–3.9 (2H, m), 3.70 (3H, s), 3.76 (3H, s), 4.1–4.45 (1H, m), 4.62 (1H, d, J=15 Hz), 4.77 (1H, d, J=15 Hz), 6.45 (2H, m), 7.05–7.6 (26H, m).

Example I-33

Preparation of N-(2,4-dimethoxybenzyl)-1-trimethylsilylethynyl-2-aza-3-oxo-6-tert-butyldiphenylsilyloxymethyl-7-tert-butyldiphenylsilyloxybicyclo[3.3.0]octane 26f

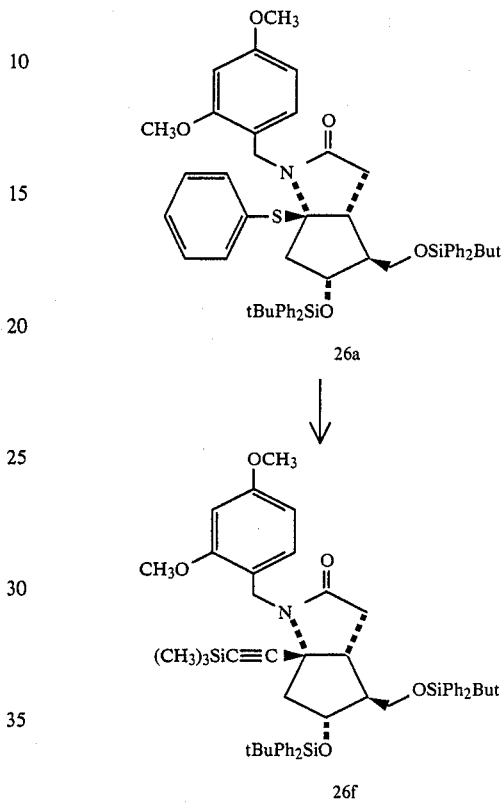

In an atmosphere of argon, a solution of 46.9 g (477 mmol) of the trimethylsilylacetylene in 420 ml of dry tetrahydrofuran is cooled with ice water and 281 ml (449 mmol) of 1.6N n-hexane solution of n-butyl lithium is dropwise added thereto over 1 hour period under stirring. The mixture is stirred at the same temperature for 30 minutes, then 0.68M tetrahydrofuran solution of zinc chloride (about 440 ml) is added to adjust it to around neutral, and the mixture is stirred in a tightly closed vessel on an oil bath at 60° C. for 1 hour. The solvent is evaporated, then a solution of 40.1 g (44.31 mmol) of the phenylthio-lactam 26a (Example I-32) in 1100 ml of dry xylene is added to the residue and the mixture is stirred in a tightly closed state on an oil bath at 140° C. for 30 minutes. After the reaction mixture is cooled, saturated aqueous solution of ammonium chloride is added and the mixture is extracted with ethyl acetate twice. The extract is washed with water, dried over anhydrous magnesium sulfate, and evaporated to give 45.2 g of residue, which is purified by column chromatography (1.5 kg of silica gel; eluted with cyclohexane:ethyl acetate=5:1) to give 28.06 g of the crude product 26f as an oil (71% yield). A portion of the crude product 26f (134 mg) is further purified by column chromatography (Lobar column, size A, 2 columns; eluted with cyclohexane:ether acetate=4:1) to give 128 mg of the foamy compound 26f.

MS:m/z 893 (M+), m/z 836 (M+ −$^t$Bu).

$[\alpha]_D^{22}$ −12.1±1.0° (c=0.513, CHCl$_3$).

IR:$\nu_{max}^{CHCl_3}$ 2164, 1673, 1617, 1592, 1510, 1114, 845 cm$^{-1}$.

NMR:$\delta_{ppm}^{CDCl_3}$ 0.0 (9H, s), 0.94 (9H, s), 0.98 (9H, s), 3.58 (2H, m), 3.67 (3H, s), 3.73 (3H, s), 4.08 (1H, m), 4.42 (1H, d, J=15 Hz), 4.53 (1H, d, J=15 Hz), 6.35 (2H, m), 7.15-7.65 (21H, m).

Example I-34

Preparation of N-(2,4-dimethoxybenzyl)-1-propynyl-2-aza-3-oxo-6-tert-butyldiphenylsilyloxymethyl-7-tert-butyldiphenyl-silyloxybicycl[3.3.0]octane 26h

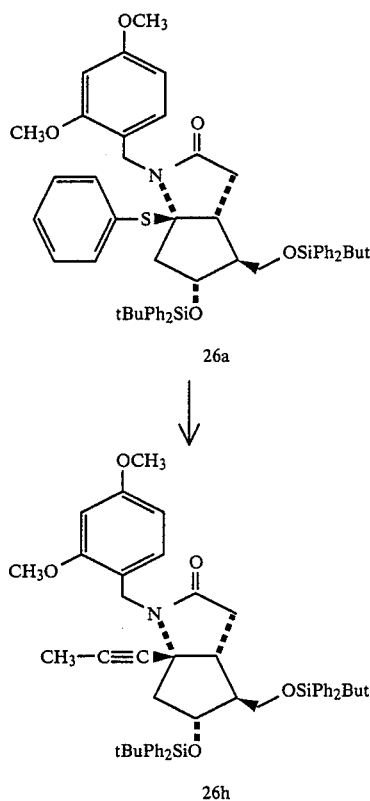

To a solution of 39.42 g (349 mmol) of 1-trimethyl-silylpropyne in 400 ml of dry tetrahydrofuran is added dropwise 178 ml (281 mmol) of 1.58M ethyl ether solution of methyl lithium-lithium bromide complex in small portions in an atmosphere of argon, and the mixture is stirred at room temperature for 3 hours to become a white suspension. This suspension is cooled with iced water, and 0.72M tetrahydrofuran solution of zinc chloride is added to adjust it to around neutral (added about 342 ml). It becomes a solution, which is stirred in a tightly closed state on an oil bath at 60° C. for 1 hour, and evaporated. To the residue is added a solution of 25.43 g (28.1 mmol) of the phenylthiolactam 26a (Example I-32) in 900 ml of dry xylene and the mixture is stirred in a tightly closed state on an oil bath at 140° C. for 1 hour. After the reaction mixture is cooled, saturated aqueous solution of ammonium chloride is added. The mixture is extracted with ethyl acetate twice and the extract is washed with water, dried over anhydrous magnesium sulfate, and evaporated to give 39.1 g of residue, which is purified by column chromatography (750 g of silica gel; eluted with toluene-toluene:ethyl acetate=12:1) to give 17.44 g of the crude product 26h as a foamy material 74% yield). A portion of the crude product (240 mg) is further purified by thin layer chromatography (Merck; precoated plate, size 20 cm×20 cm, thickness 0.5 mm, 9 sheets; eluted with n-hexane:ethyl acetate=3:1) to give 233 mg of the compound 26h as a foamy material.

MS:m/z b 835 (M$^+$), m/z 778 (M$^+$—$^t$Bu).

[α]$_D$ −7.1±0.9° (c=0.504, CHCl$_3$).

IR:$\nu_{max}^{CDCl_3}$ 1675, 1615, 1592, 1510, 1114 cm$^{-1}$.

NMR:$\delta_{ppm}^{CDCl_3}$ 0.92 (9H, s), 0.98 (9H, s), 1.56 (3H, s), 3.45-3.8 (2H, m), 3.70 (3H, s), 3.75 (3H, s), 3.95-4.25 (1H, m), 4.49 (2H, m), 6.38 (2H, m), b 7.1-7.7 (21H, m).

Example I-35

Preparation of N-(2,4-dimethoxybenzyl)-1-ethynyl-2-aza-3-oxo-6-hydroxymethyl-7-hydroxybicyclo[3.3.0]octane 27 g

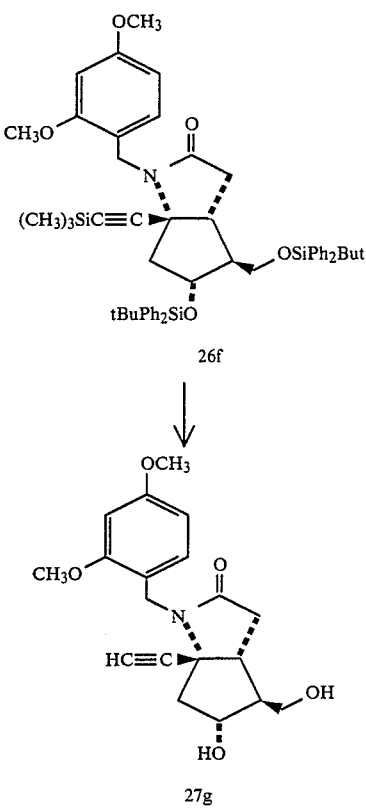

To a solution of 24.98 g (27.97 mmol) of the silyl ether 26f (Example I-33) in 300 ml of dry tetrahydrofuran is added 200 ml (200 mmol) of 1M tetrahydrofuran solution of tetra-n-butylammonium fluoride in an atmosphere of nitrogen and the mixture is stirred at room temperature for 1 hour and 30 minutes. Saturated aqueous solution of ammonium chloride is added to the reaction mixture, which is then extracted with ethyl acetate twice. The extract is washed with saturated aqueous solution of sodium chloride, dried over anhydrous magnesium sulfate, and evaporated to give 31.22 g of residue, which is dissolved in ethyl acetate. The solution is washed with dilute aqueous solution of sodium hydrogencarbonate and then with saturated aqueous solution of sodium chloride. The aqueous layer is extracted with ethyl acetate twice and the extract is washed with saturated aqueous solution of sodium chloride. The combined organic layer is dried over anhydrous magnesium sulfate and evaporated to give 26.9 g of residue, which is purified by column chromatography (270 g of alumina; eluted with benzene:ethyl acetate=1:1-ethyl acetate:methanol=20:1-ethyl acetate:methanol=1:1) to give 9.09 g of the product 27 g (94% yield). A portion of the product 27g is recrystallized from dichloromethane-ethyl ether to give the compound 27 g, mp. 159°-160° C.

MS:m/z 345 (M+).

$[\alpha]_D^{23} + 29.4 \pm 1.4°$ (c=0.487, CHCl$_3$).

IR:$\nu_{max}^{CHCl_3}$ 3624, 3440, 3312, 1678, 1617, 1592, 1510, 1159, 1131, 1038 cm$^{-1}$.

NMR:$\delta_{ppm}^{CDCl_3}$ 2.39 (1H, s), 3.65 (2H, m), 3.75 (3H, s), 3.77 (3H, s), 4.08 (1H, m), 4.43 (1H, d, J=15 Hz), 4.62 (1H, d, J=15 Hz), 6.42 (2H), 7.2 (1H).

Example I-36

Preparation of N-(2,4-dimethoxybenzyl)-1-propynyl-2-aza-3-oxo-6-hydroxymethyl-7-hydroxybicyclo[3.3.0]octane 27h

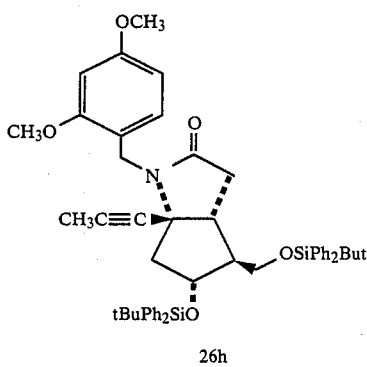

26h

↓

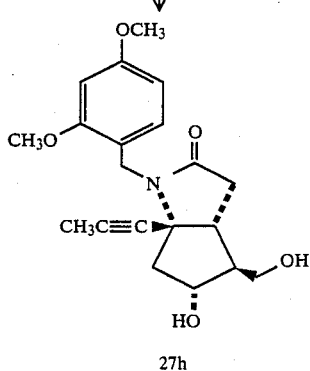

27h

Removal of silyl groups carried out in the same manner as in Example I-35 using 17.14 g of the silyl ether 26h (Example I-34) affords 6.70 g of the compound 27h, mp. 126°-127.5° C., (91% yield).

MS:m/z 359 (M+).

$[\alpha]_D^{24} - 2.7 \pm 0.8°$ (c=0.512, CHCl$_3$).

IR:$\nu_{max}^{CDCl_3}$ 3620, 3548, 3444, 1676, 1616, 1592, 1510, 1159, 1130, 1040 cm$^{-1}$.

NMR:$\delta_{ppm}^{CDCl_3}$ 1.68 (3H, s), 3.5-3.9 (2H, m), 3.77 (3H, s), 3.80 (3H, s), 4.1 (1H, m), 4.45 (1H, d, J=15 Hz), 4.57 (1H, d, J=15 Hz), 6.43 (2H), 7.22 (1H).

Example I-37

Preparation of N-(2,4-dimethoxybenzyl)-1-ethynyl-2-aza-3-oxo-6-tert-butyldimethylsilyloxymethyl-7-hydroxybicyclo[3.3.0]octane 28g

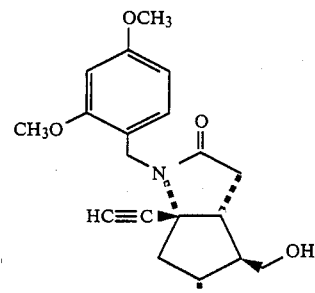

27g

↓

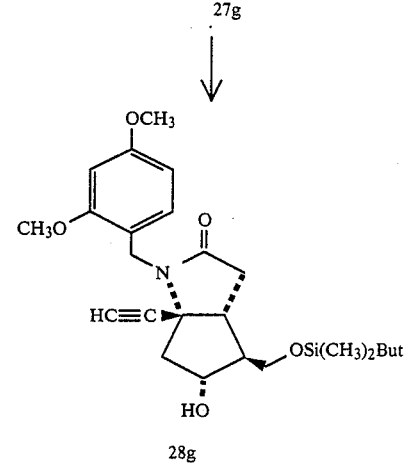

28g

To a solution 9.09 g (26.35 mmol) of the diol 27g (Example I-35) in 100 ml of dry dichloromethane are added a solution of 6.50 g (53.2 mmol) of 4-dimethylaminopyridine and 4.49 g (29.77 mmol) of tert-butyldimethysilyl chloride in 44 ml of dry dichloromethane in an atmosphere of nitrogen and the mixture is allowed to stand at room temperature overnight. Saturated aqueous solution of sodium chloride is added to the reaction mixture, which is extracted with dichloromethane 3 times. The extract is successively washed with 1N hydrochloric acid, water, dilute aqueous solution of sodium hydrogencarbonate, and water, dried over anhydrous magnesium sulfate, and evaporated to give 12.08 g of residue, which is purified by column chromatography (150 g of silica gel; eluted with benzene-benzene:ethyl acetate=20:1-benzene:ethyl acetate=2:1) to give 8.89 g of the compound 28g (73.5% yield), which is recrystallized from acetone-n-hexane to give the crystals, mp. 112°-113° C.

MS:m/z 459 (M+).

$[\alpha]_D^{21.5} + 32.0 \pm 1.4°$ (c=0.503, CHCl$_3$).

IR:$\nu_{max}^{CDCl_3}$ 3532, 3312, 1684, 1617, 1592, 1510, 1159, 1130, 1086, 1039, 839 cm$^{-1}$.

NMR:$\delta_{ppm}^{CDCl_3}$ 0.06 (6H, s), 0.88 (9H, s), 2.39 (1H, s), 3.7 (2H, m), 3.75 (3H, s), 3.79 (3H, s), 4.08 (1H, m), 4.41 (1H, d, J=15 Hz), 4.69 (1H, d, J=15 Hz), 6.40 (2H, m), 7.25 (1H).

Example I-38

Preparation of N-(2,4-dimethoxybenzyl)-1-propynyl-2-aza-3-oxo-6-tert-butyldimethylsilyloxymethyl-7-hydroxybicyclo[3.3.0]octane 28h

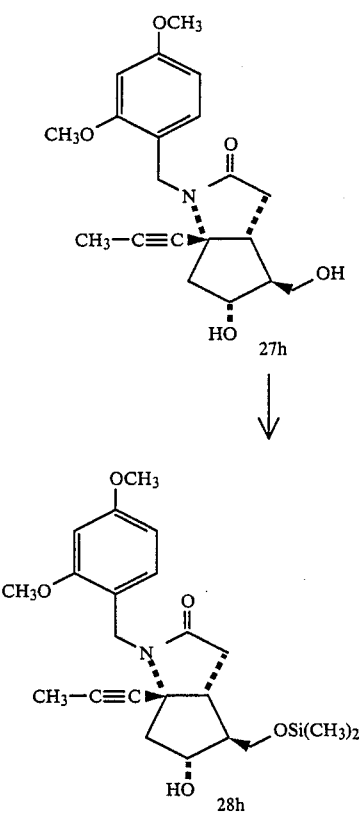

The silylation carried out in the same manner as in Example I-37 using 6.54 g of the diol 27h (Example I-36) affords 4.53 g of the compound 28h (52.5% yield), mp. 125°–128° C.

MS:m/z 473 (M+).

$[\alpha]_D^{24}$ +5.5±0.9° (c=0.507, CHCl$_3$).

IR:$\nu_{max}^{CHCl3}$ 3536, 1679, 1616, 1591, 1510, 1158, 1127, 1085, 1039, 837 cm$^{-1}$.

NMR:$\delta_{ppm}^{CDCl3}$ 0.06 (6H, s), 0.88 (9H, s), 1.70 (3H, s), 3.55–3.85 (2H, m), 3.74 (3H, s), 3.78 (3H, s), 4.03 (1H, m), 4.43 (1H, d, J=15 Hz), 4.61 (1H, d, J=15 Hz), 6.43 (2H), 7.24 (1H).

Example I-39

Preparation of N-(2,4-dimethoxybenzyl)-1-ethynyl-2-aza-3-oxo-6-tert-butyldimethylsilyloxymethyl-7-p-phenylbenzoyloxybicyclo[3.3.0]octane 29g

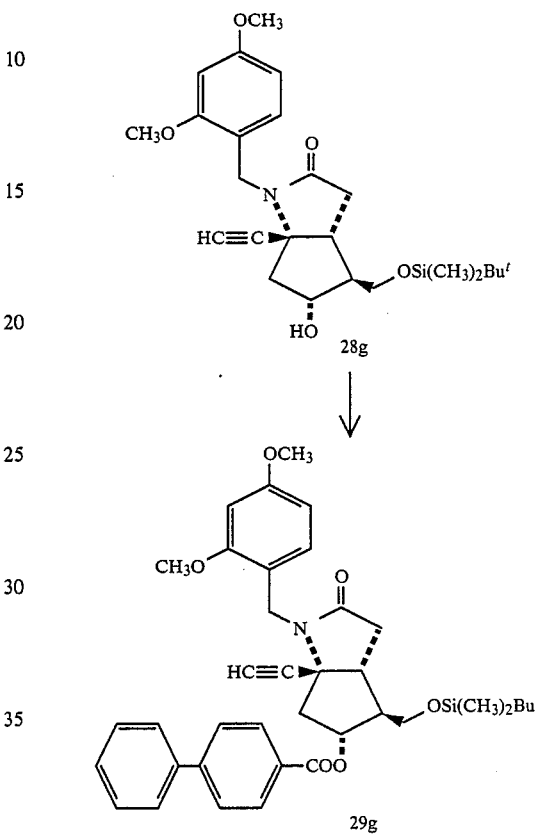

To a solution of 8.71 g (18.97 mmol) of the alcohol 28g (Example 37) in 200 ml of dry dichloromethane are added 6.95 g (56.89 mmol) of 4-dimethylaminopyridine and 8.48 g (37.96 mmol) of p-phenylbenzoyl chloride in an atmosphere of nitrogen and the mixture is stirred at room temperature for 1 hour and 30 minutes. Iced water is added to the reaction mixture, which is extracted three times with dichloromethane. The extract is successively washed with 1N hydrochloric acid, water, dilute aqueous solution of sodium hydrogencarbonate, and water, dried over anhydrous magnesium sulfate, and evaporated to give 12.74 g of residue, which is purified by column chromatography (150 g of silica gel; eluted with benzene:ethyl acetate=50:1-benzene:ethyl acetate=10:1) to give 12.03 g of the crude product 29g (99% yield). A portion (177 mg) of the crude product 29g is further purified by column chromatography (5.5 g of silica gel; benzene:ethyl acetate=50:1-benzene:ethyl acetate=20:1) to give 170 mg of the compound 29g as a foamy material.

MS: m/z 639 (M+), m/z 582 (M+−$^t$Bu).

$[\alpha]_D^{21}$ +16.1±1.1° (c=0.510, CHCl$_3$).

IR: $\nu_{max}^{CHCL3}$ 3312, 1712, 1682, 1613, 1592, 1510, 1278, 1269, 1127, 1117, 837 cm$^{-1}$.

NMR: $\delta_{ppm}^{CDCl3}$ 0.06 (6H, s), 0.88 (9H, s), 2.32 (1H, s), 3.6–3.8 (2H), 3.63 (3H, s), 3.73 (3H, s), 4.50 (1H, d, J=15 Hz), 4.59 (1H, d, J=15 Hz), 5.32 (1H, m), 6.25

(2H, m), 7.3–7.65 (6H, m), 7.63 (2H, d, J=8 Hz), 7.94 (2H, d, J=8 Hz).

Example I-40

Preparation of N-(2,4-dimethoxybenzyl)-1-propynyl-2-aza-3-oxo-6-tert-butyldimethylsilyloxymethyl-7-p-phenylbenzoyl oxybicyclo[3.3.0]octane 29h

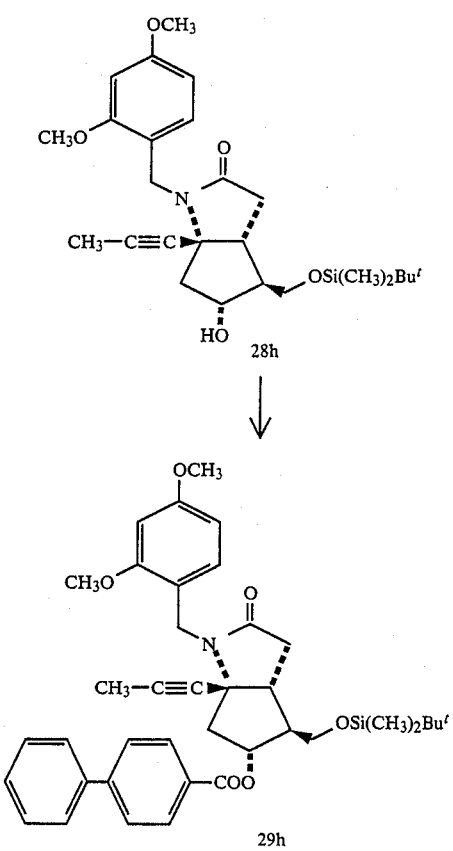

The esterification carried out in the same manner as in Example I-39 using 4.53 g of the alcohol 28h (Example I-38) affords 5.73 g of the compound 29h as a foamy material (93% yield).

MS: m/z 653 (M+), m/z 596 (M+ − $^t$Bu). $[\alpha]_D^{23}30$ 12.2±1.0° (c=0.510, CHCL$_3$).

IR: $\nu_{max}^{CHCl_3}$ 1714, 1679, 1613, 1592, 1509, 1279, 1269, 1125, 1116, 1104, 838 cm$^{-1}$.

NMR: $\delta_{ppm}^{CDCl_3}$ 0.06 (6H, s), 0.90 (9H, s), 1.69 (3H, s), 3.6–3.8 (2H), 3.64 (3H, s), 3.76 (3H, s), 4.47 (1H, d, J=15 Hz), 4.62 (1H, d, J=15 Hz), 5.32 (1H, m), 6.27 (2H, m), 7.25–7.6 (6H, m), 7.64 (2H, d, J=8 Hz), 7.95 (2H, d, J=8 Hz).

Example I-41

Preparation of 1-ethynyl-2-aza-3-oxo-6-hydroxymethyl-7-p-phenyl-benzoyloxybicyclo[3.3.0] octane 30g

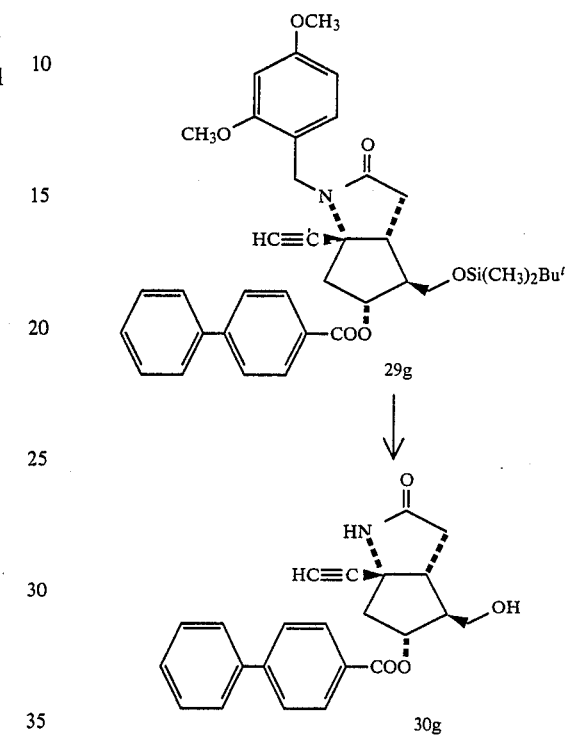

To a solution of 11.86 g (18.56 mmol) of the benzyl-lactam 29g (Example I-39) in 250 ml of acetonitrile-water mixture (9:1) is added 21 g (38.32 mmol) of ammonium cerium (IV) nitrate at room temperature under stirring. Every 20 minutes, additional amounts of ammonium cerium (IV) nitrate, that is, 4 g (7.3 mmol), 2 g (3.65 mmol), and 2 g (3.65 mmol) added respectively. The mixture is stirred for 1 hour and 25 minutes. Iced water is added to the reaction mixture, which is then neutralized with dilute aqueous solution of sodium hydrogencarbonate. The mixture is extracted with ethyl acetate twice and the extract is washed with saturated aqueous solution of sodium chloride, dried over anhydrous magnesium sulfate, and evaporated to give 11.20 g of residue, which is purified by column chromatography (120 g of silica gel; eluted with benzene:ethyl acetate=2:1-benzene:ethyl acetate=1:1) to give 5.40 g of the product 30g (77.5% yield), which is recrystallized from acetone to give the crystals, mp. 201°–203° C.

MS: m/z 375 (M+).

$[\alpha]_D^{21.5}$ −19.3±1.2° (c=0.512, CHCl$_3$:CH$_3$OH=1:1).

IR: $\nu_{max}^{KBr}$ 3424, 3276, 3192, 1722, 1681, 1611, 1268, 1112 cm$^{-1}$.

NMR: $\delta_{ppm}^{CDCl_3+CD_3OD}$ 2.65 (1H, s), 3.68 (2H, m), 5.45 (1H, m), 7.35–7.7 (5H, m), 7.66 (2H, d, J=8 Hz), 8.04 (2H, d, J=8 Hz).

Example I-42

Preparation of 1-propynyl-2-aza-3-oxo-6-hydroxymethyl-7-p-phenyl-benzoyloxybicyclo[3.3.0]octane 30h

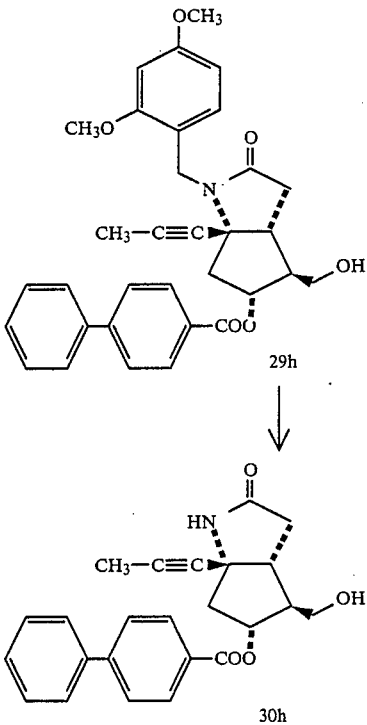

In the same manner as in Example I-41, 150 mg of the benzyl-lactam 29h (Example I-40) is allowed to react to give 50 mg of the compound 30h, mp. 159°–160° C. (63% yield).

MS: m/z 389 (M+)

$[\alpha]_D^{23}$ +27.8±1.3° (c=0.511, CHCl$_3$).

IR: $\nu_{max}^{CHCl_3}$ 3628, 3432, 1703, 1612, 1280, 1115 cm$^{-1}$.

NMR: $\delta_{ppm}^{CDCl_3}$ 1.79 (3H, s), 3.70 (2H, m), 5.47 (1H, m), 6.70 (1H, s), 7.35–7.7 (5H, m), 7.65 (2H, d, J=8 Hz), 8.03 (2H, d, J=8 Hz).

Example I-43

Preparation of 1-ethenyl-2-aza-3-oxo-6-hydroxymethyl-7-p-phenyl-benzoyloxybicyclo[3.3.0] octane 30l

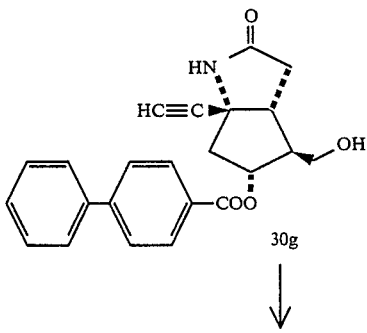

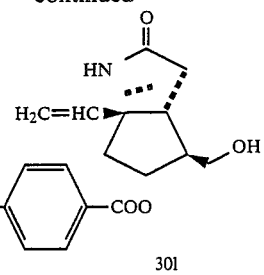

To a solution of 609 mg of the ethynyl-lactam 30g (Example I-41) in 60 ml of methanol are added 0.6 ml of quinoline and 36 mg of 5% palladium-barium sulfate. The mixture is stirred at ordinary temperature and atmosphric pressure in an atmosphere of hydrogen for 49 minutes. The reaction mixture is filtrated to remove the insoluble matteer and the filtrate is evaporated. The residue is dissolved in ethyl acetate, which is successively washed with 1N hydrochloric acid, water, dilute aqueous solution of sodium hydrogencarbonate, and saturated aqueous solution of sodium chloride, dried over anhydrous maagnesium sulfate, and evaporated. The residue is purified by column chromatography (25 g of silica gel; ethyl acetate) to give 441 mg of the compound 30l (72.5% yield). The product is recrystallized from dichloromethane-ethyl ether to give the crystals, mp. 121°–122° C.

MS: m/z 377 (M+).

$[\alpha]_D^{23}$ −43.1±1.7° (c=0.50, CHCl$_3$).

IR: $\nu_{max}^{CHCl_3}$ 3432, 1700, 1612, 1279, 1115 cm$^{-1}$.

NMR: $\delta_{ppm}^{CDCl_3}$ 3.50–3.92 (2H, m), 5.11 (1H, d, j=10 Hz), 5.23 (1H, d, j=18 Hz), 5.45 (1H, m), 5.96 (1H, dd, J=10, 18 Hz), 6.59 (1H, s), 7.35–7.75 (7H, m), 8.06 (2H, d, J>8 Hz).

Example I-44

Preparation of 1-ethynyl-2-aza-3-oxo-6-(3-oxo-oct-1-enyl-)-7-p-phenyl-benzoyloxybicyclo[3.3.0]octane 31g

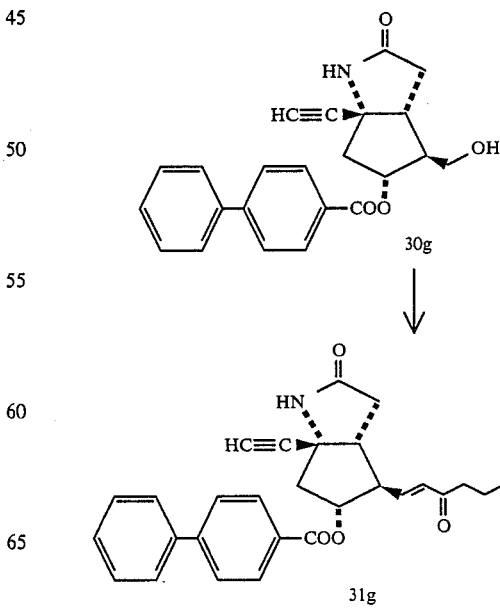

A solution of 349 mg (2.75 mmol) of oxalyl chloride in 8 ml of dichloromethane is cooled to −60° C. in an atmosphere of nitrogen, 1.63 ml of dichloromethane solution of dimethylsulfoxide (275 mg/ml; 448 mg of dimethylsulfoxide, 5.74 mmol) is added in small portions under stirring, and the mixture is stirred at the same temperature for 10 minutes. To the reaction mixture is added dropwise a solution of 500 mg (1.333 mmol) of the alcohol 30g (Example I-41) in 50 ml of dry tetrahydrofuran-dry dichloromethane mixture (1:1) over 18 minute period. The mixture is stirred at the same temperature for additional 30 minutes and 573 mg (5.67 mmol) of triethylamine is added. The reaction mixture is warmed up to room temperature and acidified with 1N hydrochloric acid, then water is added, and the mixture is extracted 3 times with dichloromethane. The extract is washed with water, dried over anhydrous magnesium sulfate, and evaporated to give 530 mg of residue.

To a solution of 385 mg (1.735 mmol) of dimethyl(2-oxoheptyl)-phosphonate in 15 ml of dry tetrahydrofuran is added 58 mg (1.47 mmol) of 61% sodium hydride in an atmosphere of nitrogen and the mixture is stirred at room temperature for 20 minutes. A solution of 530 mg of the above residue in 30 ml of tetrahydrofuran is dropwise added to the above mixture over 10 minute period and the mixture is stirred at room temperature for 25 minutes. Iced water is added to the reaction mixture, which is extracted with ethyl acetate twice. The extract is washed with saturated aqueous solution of sodium chloride, dried over anhydrous magnesium sulfate, and evaporated to give 820 mg of residue, which is applied to column chromatography (10 g of silica gel; toluene-ethyl acetate=6:1) to give 57: mg of an oil. Further, this oil is purified by column chromatography (Lobar column, size B; eluted with toluene:ethyl acetate=3:1) to give 449 mg of the product 31g (72% yield), which is recrystallized from acetone-n-hexane to give crystals, mp. 115°–117° C.

Ms: m/z 469 (M+).

$[\alpha]_D^{23}$ −88.3±2.5° (c=0.509, CHCl$_3$).

IR: $\nu_{max}^{CHCl_3}$ 3438, 3312, 1712, 1633, 1612, 1276, 1269, 1103 cm$^{-1}$.

NMR: $\delta_{ppm}^{CDCl_3}$ 0.86 (3H), 2.57 (1H, s), 5.43 (1H, m), 6.25 (1H, d, J=16 Hz), 6.76 (1H,dd, J=16, 7 Hz), 7.06 (1H, s), 7.3–7.65 (5H, m), 7.63 (2H, d, J=8 Hz), 8.01 (2H, d, J=8 Hz).

Example I-45–54

The conversion of the alcohol into the enone is carried out in the same manner as in Example I-44 and the results are shown in Table 2.

TABLE 2

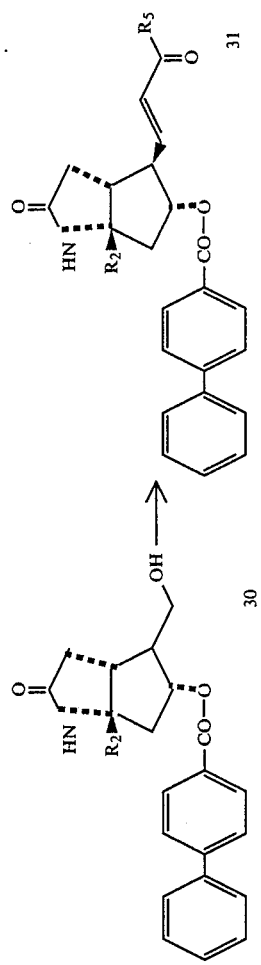

| Ex. Number | Compd. Number | R₂ | R₅ | Yd. (%) Mp. (°C.) | MS [m/z] | Specific Rotation [α]$_D$ | IR νmax [cm$^{-1}$] | NMR δppm |
|---|---|---|---|---|---|---|---|---|
| I-45 | 31g-b | CH≡C— | (isohexyl, CH(CH₃)- with CH₃) | 73.5 | 483 (M⁺) | | (CHCl₃) 3428, 3312, 1708, 1630, 1612, 1276, 1269, 1103 | (CDCl₃) 0.82 (3H), 1.05 (3H,d,J=7Hz), 2.56 (1H,s), 5.43 (1H,m), 6.33 (1H, d,J=16Hz), 6.81 (1H,d-d,J=7.5, 16Hz), 7.0 (1H,s), 7.25~7.65 (5H,m), 7.62 (2H,d,J=8Hz), 8.01 (2H,d,J=8Hz) |
| I-46 | 31g-c | CH≡C— | (H₃C-C(CH₃)-CH₃ branched) | 69.5 136~8 | 497 (M⁺) | −73.1~77.0° (23° C., c = 0.513, CHCl₃) | (CHCl₃) 3428, 3312, 1710, 1629, 1612, 1269, 1104 | (CDCl₃) 0.78 (3H), 1.08 (6H,s), 2.56 (1H,s), 5.40 (1H,m), 6.65 (1H,d, J=16Hz), 6.84 (1H,d-d,J=6, 16Hz), 7.01 (1H,s), 7.3~7.65 (5H,m), 7.61 (2H,d,J=8Hz), 8.00 (2H,d,J=8Hz) |
| I-47 | 31g-d | CH≡C— | (CH₃-C≡C-CH₂-CH(CH₃)-) | 72 | 479 (M⁺) | | (CDCl₃) 3428, 3312, 1711, 1630, 1612, 1276, 1269, 1103 | (CDCl₃) 1.14 (3H,d,J=7Hz), 1.70 (3H, t,J=2.5Hz), 2.57(1H,s), 5.44 (1H,m), 6.35 (1H,d,J=16Hz), 6.83 (1H, d-d, J=7.5, 16Hz), 7.03 (1H,s), 7.3~7.65 (5H,m), 7.64 (2H,d,J=8Hz), 8.02 (2H, d,J=8Hz) |
| I-48 | 31g-e | CH≡C— | (cyclohexyl, H) | 69 196~8 | 481 (M⁺) | −85.6 + 2.5° (22° C., c = 0.507, CHCl₃) | (CHCl₃) 3428, 3312, 1712, 1630, 1613, 1277, 1270, 1103 | (CDCl₃) 2.56 (1H,s), 5.42 (1H,m), 6.33 (1H,d,J=16Hz), 6.78 (1H,d-d, J=7.5, 16Hz), 6.95 (1H,s), 7.3~7.7 (5H,m), 7.63 (2H,d,J=8Hz), 8.01 (2H, d,J=8Hz) |
| I-49 | 31g-f | CH≡C— | (cyclopentyl) | 74 160~2 | 467 (M⁺) | −87.7 + 2.5° (21° C., c = 0.516, CHCl₃) | (CHCl₃) 3428, 3312, 1712, 1631, 1612, 1276, 1269, 1104 | (CDCl₃) 2.57 (1H,s), 5.43 (1H,m), 6.30 (1H,d,J=16Hz), 6.78 (1H,d-d, J=7.5, 16Hz), 7.17 (1H,s), 7.3~7.7 (5H,m), 7.63 (2H,d,J=8Hz), 8.01 (2H, d,J=8Hz) |

TABLE 2-continued

| Ex. Number | Compd. Number | R₂ | R₅ | Yd. (%) Mp. (°C.) | MS [m/z] | Specific Rotation [α]$_D$ | IR νmax [cm$^{-1}$] | NMR δppm |
|---|---|---|---|---|---|---|---|---|
| I-50 | 31g-g | CH≡C— | (furan with propyl) | 70 114~6 | 493 (M⁺) | −92.3 ± 2.7° (23° C., c = 0.500, CHCl₃) | (CHCl₃) 3428, 3312, 1711, 1633, 1612, 1276, 1102 | (CDCl₃) 2.57 (1H,s), 5.40 (1H,m), 5.95 (1H), 6.21 (1H), 6.23 (1H,d, J=16Hz), 6.76 (1H,d-d,J=7, 16Hz), 6.93 (1H,s), 7.24 (1H), 7.3~7.65 (5H,m), 7.62 (2H,d,J=8Hz), 8.01 (2H, d,J=8Hz) |
| I-51 | 31b | CH₃—C≡C— | —(CH₂)₄CH₃ | 71 149~150 | 483 (M⁺) | −71.8 ± 2.2° (23° C., c = 0.500, CHCl₃) | (CHCl₃) 3428, 1706, 1631, 1612, 1276, 1269, 1111, 1104 | (CDCl₃) 0.86 (3H), 1.83 (3H,s), 5.42 (1H,m), 6.23 (1H,d,J=17Hz), 6.63~6.93 (2H,m), 7.35~7.73 (7H,m), 8.03 (2H,d,J=8Hz) |
| I-52 | 31h-b | CH₃—C≡C— | —CH(CH₃)(CH₂)₃CH₃ | 68 142~4 | 497 (M⁺) |  | (CHCl₃) 3428, 1703, 1630, 1612, 1269, 1104 | (CDCl₃) 0.83 (3H), 1.05 (3H, d,J=7Hz), 1.83 (3H,s), 5.45 (1H,m), 6.33 (1H, d,J=16Hz), 6.83 (1H,d-d,J=7, 16Hz), 7.09 (1H,s), 7.36~7.75 (5H,m), 7.65 (2H,d,J=8Hz), 8.05 (2H,d,J=8Hz) |
| I-53 | 31h-e | CH₃—C≡C— | cyclohexyl | 71 221~3 | 495 (M⁺) | −71.4 ± 2.2° (23° C., c = 0.517 CHCl₃) | (CHCl₃) 3432, 1704, 1629, 1612, 1276, 1269, 1112, 1103 | (CDCl₃) 1.83 (3H,s), 5.42 (1H,m), 6.33 (1H,d,J=16Hz), 6.47 (1H,s), 6.79 (1H,d-d,J=7, 16Hz), 7.3~7.65 (5H,m), 7.64 (2H,d,J=8Hz), 8.02 (2H, d,J=8Hz) |
| I-54 | 31l-d | CH₂=CH— | —CH(CH₃)CH₂C≡CH | 81.5 | 481 (M⁺) |  | (CHCl₃) 3428, 1705, 1630, 1612, 1276, 1102 | (CDCl₃) 1.13 (3H,d,J=7Hz), 1.69 (3H), 5.06~5.49 (3H,m), 5.81~6.40 (2H,m), 6.67-7.17 (2H,m), 7.33~7.7 (7H,m), 8.03 (2H,d,J=8Hz) |

Example I-55

Preparation of
1-ethynyl-2-aza-3-oxo-6-[(3S)-3-hydroxyoct-1-enyl]-7-p-phenylbenzoyloxybicyclo[3.3.0]octane 32g and
1-ethynyl-2-aza-3-oxo-6-[(3R)-3-hydroxyoct-1-enyl]-7-p-phenylbenzoyloxybicyclo[3.3.0]octane 33g

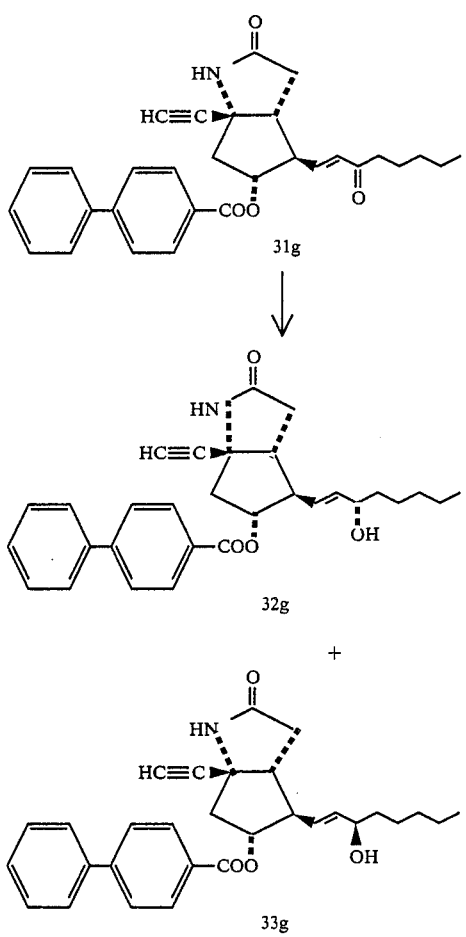

To a solution of 1.98 g (9.0 mmol) of 2,6-di-tert-butyl-4-methylphenol in 15 ml of dry toluene cooled in an ice water bath is added 6 ml (6.0 mmol) of 1.0M toluene solution of aluminium diisobutyl hydride in small portions under stirring in an atmosphere of nitrogen and the mixture is stirred at the same temperature for 30 minutes and then cooled to −25° C. To the resulting mixture is added dropwise a solution of 378 mg (0.806 mmol) of enone 31g (Example I-44) in 20 ml of dry dichloromethane over 7 minute period and the mixture is stirred at the same temperature for 23 minutes. a saturated aqueous solution of ammonium chloride is added to the reaction mixture and the mixture is stirred at room temperature for 30 minutes. After the resulting precipitate is removed by filtration, the filtrate is extracted with ethyl acetate twice. The extract is washed with water, dried over anhydrous magnesium sulfate, and evaporated to give 3.20 g of residue, which is applied to column chromatography (20 g of silica gel; eluted with toluene-ethyl acetate) to give 376 mg of foamy material. This is further purified by column chromatography (Lober column, size B; eluted with toluene:ethyl acetate=1:1) to give 212 mg of foamy material 32g (56% yield) and 148 mg of foamy material 33g (30% yield). The product 33g is crystallized from ethyl ether to give a sample of mp. 139°–141° C.

32g
MS: m/z 471 (M+).
$[\alpha]_D^{22}$ −45.8±1.7° (c=0.500, CHCl$_3$).
IR: $\nu_{max}^{CHCl_3}$ 3608, 3432, 3312, 1711, 1612, 1278, 1111, 1102 cm$^{-1}$.
NMR: $\delta_{ppm}^{CDCl_3}$ 0.83 (3H), 2.53 (1H, s), 4.10 (1H, m), 5.36 (1H, m), 5.66 (2H, m), 7.04 (1H, s), 7.3–7.6 (5H, m), 7.63 (2H, d, J=8 Hz), 8.01 (2H, d, J=8 Hz).

33g
MS: m/z 471 (M+).
$[\alpha]_D^{22}$ −59.3±2.0° (c=500, CHCl$_3$).
IR: $\nu_{max}^{CHCl_3}$ 3608, 3432, 3312, 1710, 1612, 1277, 1111, 1102 cm$^{-1}$.
NMR: $\delta_{ppm}^{CDCl_3}$ 0.80 (3H9, 2.53 (1H, s), 4.07 (1H, m), 5.35 (1H, m), 5.65 (2H, m), 7.03 (1H, s), 7.3–7.6 (5H, m), 7.63 (2H, d, J=8 Hz), 8.01 (2H, d, J=8 Hz).

Example I-56–65

The reduction is carried out in the same manner as in Example I-55 and the results are shown in Table 3.

TABLE 3

| Ex. Number | Compd. Number | R₂ | R₆ | Yd. (%) Mp. (°C.) | MS [m/z] | Specific Rotation [α]$_D$ | IR νmax [cm⁻¹] | NMR δppm |
|---|---|---|---|---|---|---|---|---|
| I-56 | 32g-b | CH≡C— | CH₃ branched (isohexyl) | 56.5 | 485 (M⁺) | | (CHCl₃) 3612, 3428, 3312, 1710, 1612, 1277, 1111, 1104 | (CCDCl₃) 0.83 (6H,m), 2.53 (1H,s), 3.97 (1H,m), 5.35 (1H,s), 5.65 (2H, m), 6.86 (1H,s), 7.2~7.65 (5H,m), 7.63 (2H,d,J=8Hz), 8.02 (2H,d,J=8Hz) |
| | 33g-b | | | 34 | 485 (M⁺) | | (CHCl₃) 3612, 3428, 3312, 1708, 1612, 1277, 1111, 1103 | (CDCl₃) 0.80 (6H,m), 2.53 (1H,s), 3.95 (1H,m), 5.35 (1H,s), 5.65 (2H, m), 6.70 (1H,s), 7.2~7.65 (5H,m), 7.63 (2H,d,J=8Hz), 8.03 (2H,d,J=8Hz) |
| I-57 | 32g-c | CH≡C— | H₃C—C(CH₃)₂— alkyl | 62.5 | 499 (M⁺) | −36.6 ± 1.5° 22° C = 0.506, CHCl₃ | (CHCl₃) 3612, 3432, 3312, 1710, 1612, 1277, 1111, 1104 | (CDCl₃) 0.78 (3H,s), 0.82 (3H,s), 0.84 (3H), 2.53 (1H,s), 3.82 (1H,d, J=5Hz), 5.36 (1H,m), 5.72 (2H,m), 7.02 (1H,s), 7.3~7.6 (5H,m), 7.62 (2H,d,J=8Hz), 8.01 (2H,d,J=8Hz) |
| | 33g-c | | | 33.5 | 499 (M⁺) | −70.9 ± 2.2° 22° C = 0.502, CHCl₃ | (CHCl₃) 3616, 3432, 3312, 1708, 1612, 1277, 1112, 1104 | (CDCl₃) 0.77 (3H,s), 0.81 (3H,s), 0.83 (3H), 2.54 (1H,s), 3.78 (1H,d, J=5Hz), 5.35 (1H,m), 5.69 (2H,m), 6.97 (1H,s), 7.3~7.6 (5H,m), 7.63 (2H,d,J=8Hz), 8.02 (2H,d,J=8Hz) |
| I-58 | 32g-d | CH≡C— | CH₃ alkyne branched | 50.5 | 481 (M⁺) | | (CHCl₃) 3612, 3432, 3312, 1710, 1612, 1277, 1111, 1104 | (CDCl₃) 0.89 (3H,d,J=7Hz), 1.73 (3H, t,J=2.5Hz), 2.53 (1H,s), 4.13 (1H, m), 5.35 (1H,m), 5.69 (2H,m), 6.94 (1H,s), 7.2~7.65 (5H,m), 7.62 (2H,d, J=8Hz), 8.01 (2H,d,J=8Hz) |
| | 33g-d | | | 38.5 | 481 (M⁺) | | (CHCl₃) 3616, 3432, 3312, 1711, 1612, 1277, 1104 | (CDCl₃) 0.88 (3H,m), 1.73 (3H), 2.54 (1H,s), 4.10 (1H,m), 5.35 (1H,s), 5.68 (2H,m), 6.94 (1H,s), 7.2~7.65 (5H,m), 7.64 (2H,d,J=8Hz), 8.03 (2H, d,J=8Hz) |
| I-59 | 32g-e | CH≡C— | cyclohexyl | 60.5 174~5 | 483 (M⁺) | −41.1 ± 1.6° (24° C., c = 0.507, CHCl₃) | (CHCl₃) 3612, 3428, 3312, 1711, 1612, 1277, 1111, 1104 | (CDCl₃) 2.53 (1H,s), 3.84 (1H,m), 5.35 (1H,m), 5.64 (2H,m), 6.96 (1H, s), 7.3~7.65 (5H,m), 7.62 (2H,d, J=8Hz), 8.02 (2H,d,J=8Hz) |
| | 33g-e | | | 35.5 91~4 | 483 (M⁺) | −60.9 ± 2.0° (24° C., | (CHCl₃) 3612, 3428, 3312, 1709, 1612, 1277, 1111, | (CDCl₃) 2.54 (1H,s), 3.8 (1H,m), 5.35 (1H,s), 5.62 (2H,m), 7.02 (1H, |

TABLE 3-continued

Scheme: Compound 31 → Compound 32 + Compound 33

| Ex. Number | Compd. Number | R2 | R6 | Yd. (%) Mp. (°C.) | MS [m/z] | Specific Rotation [α]D | IR νmax [cm⁻¹] | NMR δppm |
|---|---|---|---|---|---|---|---|---|
| | | | | | | | | s), 7.3∼7.65 (5H,m), 7.62 (2H,d, J=8Hz), 8.02 (2H,d,J=8Hz) |
| I-60 | 32g-f | CH≡C— | cyclopentylmethyl | 58.5 | 469 (M⁺) | −48.5 ± 1.8° (24° C., c = 0.499, CHCl₃) | (CHCl₃) 3608, 3432, 3312, 1710, 1612, 1277, 1111, 1104 | (CDCl₃) 2.54 (1H,s), 3.90 (1H,m), 5.35 (1H,m), 5.67 (2H,m), 7.01 (1H, s), 7.3∼7.65 (5H,m), 7.63 (2H,d, J=8Hz), 8.02 (2H,d,J=8Hz) |
| | 33g-f | | | 32 | 469 (M⁺) | −59.1 ± 1.9° (24° C., c = 0.518, CHCl₃) | (CHCl₃) 3608, 3432, 3312, 1709, 1612, 1277, 1111, 1104 | (CDCl₃) 2.55 (1H,s), 3.88 (1H,m), 5.36 (1H,m), 5.66 (2H,m), 7.02 (1H, s), 7.3∼7.65 (5H,m), 7.63 (2H,d, J=8Hz), 8.02 (2H,d,J=8Hz) |
| I-61 | 32g-g | CH≡C— | furanyl-propyl | 48 | 495 (M⁺) | −46.4 ± 1.7° (22° C., c = 0.511, CHCl₃) | (CHCl₃) 3608, 3428, 3312, 1710, 1612, 1278, 1111, 1104 | (CDCl₃) 2.53 (1H,s), 4.13 (1H,m), 5.34 (1H,m), 5.67 (2H,m), 5.91 (1H), 6.22 (1H), 6.97 (1H,s), 7.23 (1H), 7.3∼7.6 (5H,m), 7.62 (2H,d,J=8Hz), 8.01 (2H,d,J=8Hz) |
| | 33g-g | | | 40.5 | 495 (M⁺) | −64.1 ± 2.0° (22° C., c = 0.510, CHCl₃) | (CHCl₃) 3612, 3428, 3312, 1711, 1612, 1277, 1109, 1104 | (CDCl₃) 2.53 (1H,s), 4.12 (1H,m), 5.35 (1H,m), 5.66 (2H,m), 5.90 (1H), 6.20 (1H), 7.01 (1H,s), 7.23 (1H), 7.3∼7.6 (5H,m), 7.62 (2H,d,J=8Hz), 8.01 (2H,d,J=8Hz) |
| I-62 | 32h | CH₃—C≡C— | —(CH₂)₄CH₃ | 52 | 485 (M⁺) | −30.5 ± 1.4° (23° C., c = 0.513, CHCl₃) | (CHCl₃) 3608, 3432, 1705, 1612, 1278, 1115, 1105 | (CDCl₃) 0.83 (3H), 1.81 (3H,s), 4.09 (1H,m), 5.33 (1H,m), 5.63 (2H,m), 6.66 (1H,d), 7.34∼7.67 (5H,m), 7.61 (2H,d,J=8Hz), 8.02 (2H,d,J=8Hz) |
| | 33h | | | 30 | 485 (M⁺) | −43.2 ± 1.6° (23° C., c = 0.516, CHCl₃) | (CHCl₃) 3608, 3432, 1706, 1612, 1278, 1114, 1102 | (CDCl₃) 0.78 (3H), 1.82 (3H,s), 4.08 (1H,m), 5.31 (1H,m), 5.63 (2H,m), 6.73 (1H,s), 7.35∼7.67 (5H,m), 7.61 (2H,d,J=8Hz), 8.02 (2H,d,J=8Hz) |
| I-63 | 32h-b | CH₃—C≡C— | —CH₂CH(CH₃)CH₂CH₃ | 62.5 | 499 (M⁺) | | (CHCl₃) 3612, 3428, 1704, 1612, 1277, 1114 | (CDCl₃) 0.85 (6H,m), 1.82 (3H,s), 3.96 (1H,m), 5.34 (1H,m), 5.66 (2H, m), 7.02 (1H,s), 7.32∼7.65 (5H,m), 7.60 (2H,d,J=8Hz), 8.03 (2H,d,J=8Hz) |

TABLE 3-continued

| Ex. Number | Compd. Number | R2 | R6 | Yd. (%) Mp. (°C.) | MS [m/z] | Specific Rotation [α]D | IR νmax [cm⁻¹] | NMR δppm |
|---|---|---|---|---|---|---|---|---|
| | 33h-b | | | 33 | 499 (M⁺) | | (CHCl₃) 3612, 3428, 1706, 1612, 1278, 115 | (CDCl₃) 0.80 (6H,m), 1.81 (3H,s), 3.93 (1H,m), 5.33 (1H,m), 5.63 (2H,m), 6.89 (1H,s), 7.33~7.7 (5H,m), 7.60 (2H,d,J=8Hz), 8.02 (2H,d,J=8Hz) |
| I-64 | 32h-e | CH₃—C≡C— | cyclohexyl | 61 | 497 (M⁺) | −25.5 ± 1.3° (24° C., c = 0.517, CHCl₃) | (CHCl₃) 3612, 3432, 1705, 1612, 1277, 1114, 1104 | (CDCl₃) 1.81 (3H,s), 3.86 (1H,m), 5.36 (1H,m), 5.66 (2H,m), 6.92 (1H, s), 7.3~7.65 (5H,m), 7.65 (2H,d, J=8Hz), 8.04 (2H,d,J=8Hz) |
| | 33h-e | | | 32.5 | 497 (M⁺) | −45.7 ± 1.7° (24° C., c = 0.501, CHCl₃) | (CHCl₃) 3612, 3432, 1705, 1612, 1278, 1115, 1104 | (CDCl₃) 1.81 (3H,s), 3.83 (1H,m), 5.35 (1H,m), 5.63 (2H,m), 6.85 (1H, s), 7.3~7.65 (5H,m), 7.66 (2H,d, J=8Hz), 8.04 (2H,d,J=8Hz) |
| I-65 | 32l-d | CH₂=CH— | CH₃-CH(CH₃)-CH₂-C≡C- | 54 | 483 (M⁺) | | (CHCl₃) 3612, 3432, 1701, 1612, 1277, 1116 | (CDCl₃) 0.87 (3H,d,J=7Hz), 1.73 (3H), 4.17 (1H,m), 5.02~6.15 (6H,m), 7.04 (1H,s), 7.36~7.70 (5H,m), 7.64 (2H,d,J=8Hz), 8.06 (2H,d,J=8Hz) |
| | 33l-d | | | 29 | 483 (M⁺) | | (CHCl₃) 3612, 3432, 1701, 1612, 1278, 1115 | (CDCl₃) 0.86 (3H,m), 1.71 (3H), 4.16 (1H,m), 5.03~6.14 (6H,m), 6.84 (1H, s), 7.35~7.70 (5H,m), 7.66 (2H,d, J=8Hz), 8.07 (2H,d,J=8Hz) |

Example I-66

Preparation of 1-ethynyl-2-aza-3-oxo-6-[(3S)-3-hydroxyoct-1-enyl]-7-hydroxybicyclo[3.3.0]octane 34g

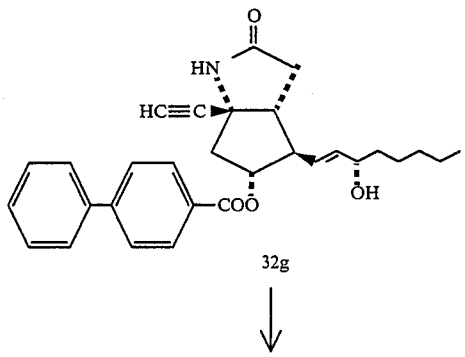

32g

↓

-continued

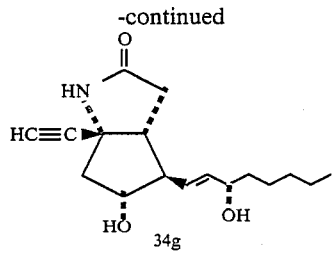

34g

To a solution of 18 mg of the ester 32g (Example I-55) in 4 ml of dry methanol is added ;b 0.2 ml of 1N methanol solution of sodium methoxide in an atmosphere of nitrogen and the mixture is stirred at room temperature for 2 hours and 10 minutes. Saturated aqueous solution of ammonium chloride is added to the reaction mixture, which is extracted with ethyl acetate twice. The extract is washed with saturated aqueous solution of sodium chloride, dried over anhydrous magnesium sulfate, and evaporated to give 208 mg of a residue, which is crystallized from ethyl ether to give 102 mg of the compound 34 g (88.5% yield). Recrystallization from ethyl ether gives a sample of mp. 187°–188° C.

MS: m/z 292 (MH+).
$[\alpha]_D$ +10.9±1.0° (c=0.503, CHCl$_3$:CH$_3$OH=1:1).
IR: $\nu_{max}^{KBr}$ 3328, 3216, 1683, 1082, 962 cm$^{-1}$.
NMR: $\delta_{ppm}^{CDCl_3+CD_3OD}$ 0.89 (3H), 2.71 (1H, s), 4.0 (2H, m), 5.55 (2H, m).

Example I-67–87

The reaction is carried out in the same manner as in Example I-66 and the results are shown in Tables 4 and 5.

TABLE 4

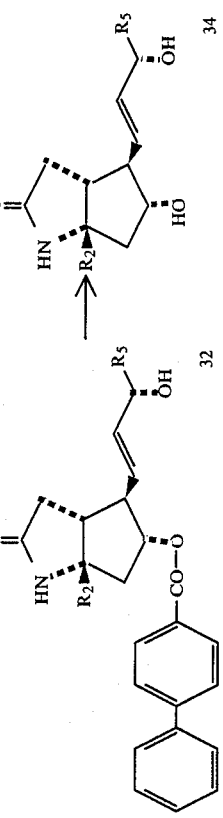

| Ex. Number | Compd. Number | R₂ | R₅ | Yd. (%) Mp. (°C.) | MS [m/z] | Specific Rotation [α]_D | IR νmax [cm⁻¹] | NMR δppm |
|---|---|---|---|---|---|---|---|---|
| I-68 | 34g-b | CH≡C— | (branched alkyl with CH₃) | 94 165~7 | 305 (M⁺) | | (KBr) 3356, 3220, 1683, 1077, 963 | (CDCl₃) 0.88 (6H,m), 2.50 (1H,s), 3.95 (2H,m), 5.52 (2H,m), 7.42 (1H,s) |
| I-70 | 34g-c | CH≡C— | (H₃C, CH₃ branched) | 97.5 | 320 (MH⁺) | +27.0 ± 1.3° (23° C., c = 0.514, CHCl₃) | (CHCl₃) 3612, 3432, 3312, 1699, 1105, 1081, 974 | (CDCl₃) 0.81 (3H,s), 0.87 (3H,s), 0.89 (3H), 2.51 (1H,s), 3.75 (1H,d, J=7Hz), 4.05 (1H,m), 5.57 (2H,m), 7.39 (1H,s) |
| I-72 | 34g-d | CH≡C— | (CH₃ branched alkyne) | 94 | 302 (MH⁺) | | (CHCl₃) 3608, 3428, 3312, 1699, 1084, 973 | (CDCl₃) 0.97 (3H,m), 1.79 (3H), 2.54 (1H,s), 4.03 (2H,m), 5.57 (2H,m), 7.44 (1H,s) |
| I-74 | 34g-e | CH≡C— | (cyclohexyl) | 94.5 188~190 | 303 (M⁺) | +13.9 ± 1.1° (24° C., c = 0.515, CHCl₃:CH₃OH = 1:1) | (KBr) 3368, 3308, 3216, 1683, 1114, 1077, 965 | (CDCl₃ + CD₃OD) 2.67 (1H,s),3.73 (1H,m), 4.03 (1H,m), 5.53 (2H,m) |
| I-76 | 34g-f | CH≡C— | (cyclopentyl) | 94.5 175~7 | 290 (MH⁺) | +14.3 ± 1.1° (24° C., c = 0.512, CHCl₃:CH₃OH = 1:1) | (KBr) 3332, 3208, 1681, 1110, 1078, 969 | (CDCl₃ + CD₃OD) 2.71 (1H,s), 3.7~4.2 (2H,m), 5.57 (2H,m) |
| I-78 | 34g-g | CH≡C— | (furyl-alkyl) | 97.5 | 315 (M⁺) | +8.6 ± 1.0° (24°, C = 0.514, CHCl₃:MeOH = 1:1) | (KBr) 3400, 3288, 1683, 1077, 1006, 974 | (CDCl₃ + CD₃OD) 2.70 (1H,s), 4.05 (2H,m), 5.58 (2H,m), 6.00 (1H), 6.26 (1H), 7.30 (1H) |
| I-80 | 34h | CH₃—C≡C— | (n-alkyl CH₃) | 96.5 | 305 (M⁺) | +4.7 ± 0.9° (23°, C = 0.506, CHCl₃) | (CHCl₃) 3608, 3432, 1698, 1075, 971 | (CDCl₃) 0.87 (3H), 1.79 (3H,s), 3.97 (2H,m), 5.49 (2H,m), 7.26 (1H,s) |

TABLE 4-continued
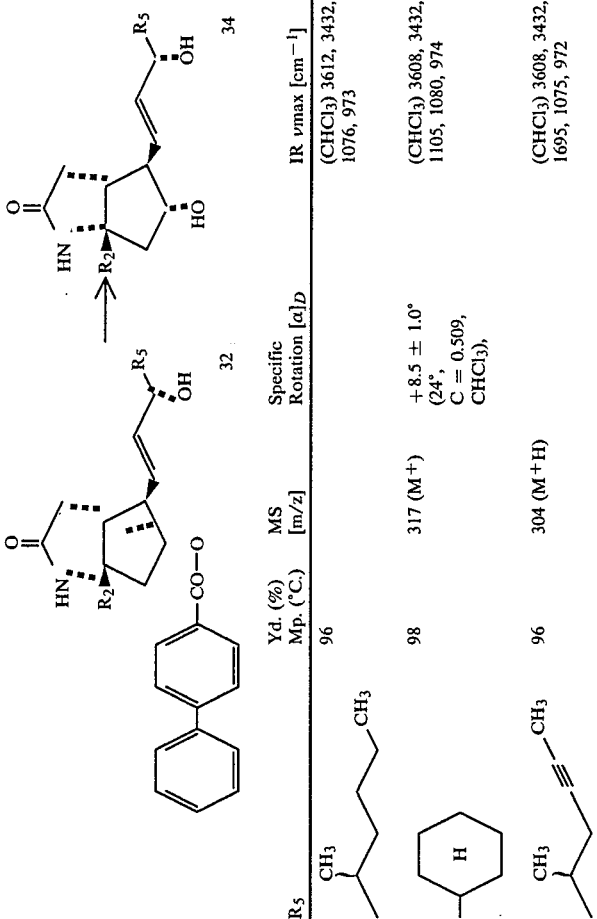
| Ex. Number | Compd. Number | R₂ | R₅ | Yd. (%) Mp. (°C.) | MS [m/z] | Specific Rotation [α]$_D$ | IR νmax [cm$^{-1}$] | NMR δppm |
|---|---|---|---|---|---|---|---|---|
| I-82 | 34-b | CH₃—C≡C— | CH₃ (branched chain with CH₃) | 96 | | | (CHCl₃) 3612, 3432, 1694, 1076, 973 | (CDCl₃) 0.87 (6H,m), 1.79 (3H,s), 3.90 (2H,m), 5.51 (2H,m), 7.01 (1H,s) |
| I-84 | 34h-e | CH₃—C≡C— | (cyclohexyl-H) | 98 | 317 (M⁺) | +8.5 ± 1.0° (24°, C = 0.509, CHCl₃) | (CHCl₃) 3608, 3432, 1695, 1105, 1080, 974 | (CDCl₃) 1.79 (3H,s), 3.5~4.2 (2H,m), 5.50 (2H,m), 7.20 (1H,s) |
| I-86 | 34l-d | CH₂=CH— | CH₃ (branched alkyne chain) | 96 | 304 (M⁺H) | | (CHCl₃) 3608, 3432, 3350, 1695, 1075, 972 | (CDCl₃) 0.95 (3H,m), 1.76 (3H), 3.89 (2H,m), 5.04 (1H,d,J=10Hz), 5.14 (1H,d,J=18Hz), 5.54 (2H,m), 5.85 (1H,d-d,J=10, 18Hz), 7.37 (1H,s) |

TABLE 5

Structure scheme:

[Biphenyl-CO-O-cyclopentane-fused-pyrrolidinone with R₂ substituent and R₅-CH(OH)-CH=CH- group at position 33] → [HO-cyclopentane-fused-pyrrolidinone with R₂ and R₅-CH(OH)-CH=CH- group at position 35]

| Ex. Number | Compd. Number | R₂ | R₅ | Yd. (%) Mp. (°C.) | MS [m/z] | Specific Rotation [α]$_D$ | IR νmax [cm⁻¹] | NMR δppm |
|---|---|---|---|---|---|---|---|---|
| I-67 | 35g | CH≡C— | —CH₂CH₂CH₂CH₃ (n-butyl) | 92 | 292 (M⁺) | −4.6 ± 0.9° (23° C., c = 0.519, CHCl₃:CH₃OH = 1:1) | (KBr) 3420, 3220, 1684, 1088, 961 | (CDCl₃ + CD₃OD) 0.89 (3H), 2.72 (1H,s), 4.03 (2H,m), 5.60 (2H,m) |
| I-69 | 35g-b | CH≡C— | —CH₂CH(CH₃)₂ isobutyl-like with two CH₃ | 84.5 | 305 (M⁺) | | (CHCl₃) 3612, 3428, 3312, 1699, 1079, 976 | (CDCl₃) 0.86 (6H,m), 2.51 (1H,s), 4.02 (2H,m), 5.62 (2H,m), 7.37 (1H,s) |
| I-71 | 35g-c | CH≡C— | —CH₂C(CH₃)₂— with H₃C, CH₃ | 93.5 | 320 (MH⁺) | −16.4 ± 1.1° (23° C., c = 0.500, CHCl₃) | (CHCl₃) 3612, 3432, 3312, 1701, 1110, 1084, 975 | (CDCl₃) 0.82 (3H,s), 0.85 (3H,s), 0.88 (3H), 2.52 (1H,s), 3.7∼4.3 (2H,m), 5.67 (2H,m), 7.40 (1H,s) |
| I-73 | 35g-d | CH≡C— | —CH(CH₃)C≡C-CH₃ | 88 | 302 (MH⁺) | | (CHCl₃) 3612, 3428, 3312, 1700, 1083, 975 | (CDCl₃) 0.96 (3H,d,J=7Hz), 1.78 (3H), 2.54 (1H,s), 4.1 (2H,m), 5.62 (2H,m), 7.42 (1H,s) |
| I-75 | 35g-e | CH≡C— | cyclohexyl | 97.5 | 303 (M⁺) | −13.2 ± 1.1° (24° C., c = 0.500, CHCl₃) | (CHCl₃) 3612, 3428, 3312, 1699, 1085, 975 | (CDCl₃) 2.54 (1H,s), 3.86 (1H,m), 4.1 (1H,m), 5.62 (2H,m), 7.03 (1H,m) |
| I-77 | 35g-f | CH≡C— | cyclopentyl | 95 | 290 (MH⁺) | −6.1 ± 0.9° (24° C., c = 0.512, CHCl₃:CH₃OH = 1:1) | (KBr) 3384, 3304, 1688, 1116, 1086, 973 | (CDCl₃ + CD₃OD) 2.69 (1H,s), 3.7∼4.2 (2H,m), 5.65 (2H,m) |
| I-79 | 35g-g | CH≡C— | furyl-CH₂CH₂CH₂— (propyl-furan) | 95.5 | 315 (M⁺) | −5.4 ± 1.8° (24° C., c = 0.258, CHCl₃:CH₃OH = 1:1) | (KBr) 3388, 3292, 1685, 1080, 1007, 974 | (CDCl₃ + CD₃OD) 2.71 (1H,s), 4.07 (2H, m), 5.63 (2H,m), 6.00 (1H), 6.26 (1H), 7.30 (1H) |

TABLE 5-continued

[Structures: left side shows bicyclic lactam with biphenyl-carboxylate ester (33), arrow to right side showing same bicyclic lactam with free hydroxyl (35), both bearing R₂ and R₅ substituents with OH on allylic carbon]

| Ex. Number | Compd. Number | R₂ | R₅ | Yd. (%) Mp. (°C.) | MS [m/z] | Specific Rotation [α]_D | IR νmax [cm⁻¹] | NMR δppm |
|---|---|---|---|---|---|---|---|---|
| I-81 | 35h | $CH_3-C\equiv C-$ | $-(CH_2)_4-CH_3$ | 95.5 | 305 (M⁺) | −5.1 ± 0.9° (23° C., c = 0.511, CHCl₃) | (CHCl₃) 3612, 3433, 1695, 1073, 974 | (CDCl₃) 0.87 (3H), 1.79 (3H,s), 4.01 (2H,m), 5.60 (2H,m), 7.04 (1H,s) |
| I-83 | 35h-b | $CH_3-C\equiv C-$ | $-CH_2-CH_2-CH(CH_3)-CH_3$ | 98 | | | (CHCl₃) 3612, 3432, 1695, 1075, 975 | (CDCl₃) 0.86 (6H,m), 1.80 (3H,s), 4.00 (2H,s), 5.60 (2H,s), 6.95 (1H,s) |
| I-85 | 35h-e | $CH_3-C\equiv C-$ | cyclohexyl-H | 97 | 317 (M⁺) | −13.1 ± 1.1° (24° C., c = 0.500, CHCl₃) | (CHCl₃) 3612, 3432, 1696, 1102, 1074, 974 | (CDCl₃) 1.80 (3H,s), 3.75~4.2 (2H,m), 5.60 (2H,m), 7.19 (1H,s) |
| I-87 | 35l-d | $CH_2=CH-$ | $-CH_2-CH(CH_3)-CH_3$ | 90.5 | 304 (M⁺) | | (CHCl₃) 3612, 3432, 1696, 1096, 1072, 974 | (CDCl₃) 0.95 (3H,d,J=7Hz), 1.76 (3H), 4.00 (2H,m), 5.04 (1H,d,J=10Hz), 5.15 (1H,d,J=18Hz), 5.63 (2H,m), 5.87 (1H,d-d,J=10, 18Hz), 7.26 (1H,s) |

Example I-88

Preparation of 1-ethynyl-2-aza-3-oxo-6-[(3S)-3-tert-butyldiphenyl-silyloxyoct-1-enyl]-7-tert-butyldiphenylsilyloxybicyclo[3.3.0.]octane 10(S) g

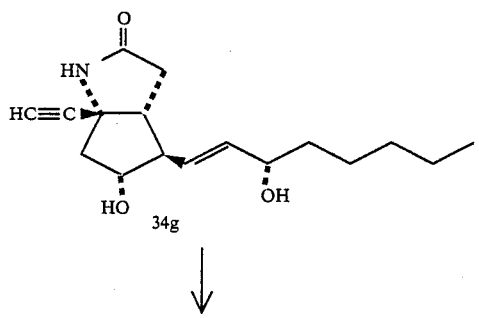
34g

↓

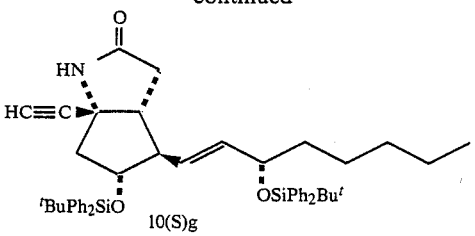
10(S)g

To a solution of 76 mg (0.261 mmol) of the alcohol 34g in 3 ml of dry N,N-dimethylformamide are added 290 mg (2.38 mmol) of 4-dimethylaminopyridine and 507 mg (1.85 mmol) of tert-buthyldiphenylsilyl chloride in an atmosphere of nitrogen and the mixture is allowed to stand at room temperature for 3 days. Ice water is poured into the reaction mixture, which is then extracted with ethyl acetate twice. The extract is washed with water, dried over anhydrous magnesium sulfate, and evaporated to give 632 mg of a residue, which is purified by column chromatography (Lobar column, size B; eluted with toluene:ethylene acetate=6:1) to give 183 mg of the compound 10(S)g as a foamy material (91.5% yield).

The compound 10(S)g prepared in this example is comfirmed to be identical with the compound prepared in Example I-24 by MS, [α]$_D$, IR and proton NMR.

Example I-89–109

The silylation is carried out in the same manner as in Example I-88 and the results are shown in Tables 6 and 7.

TABLE 6

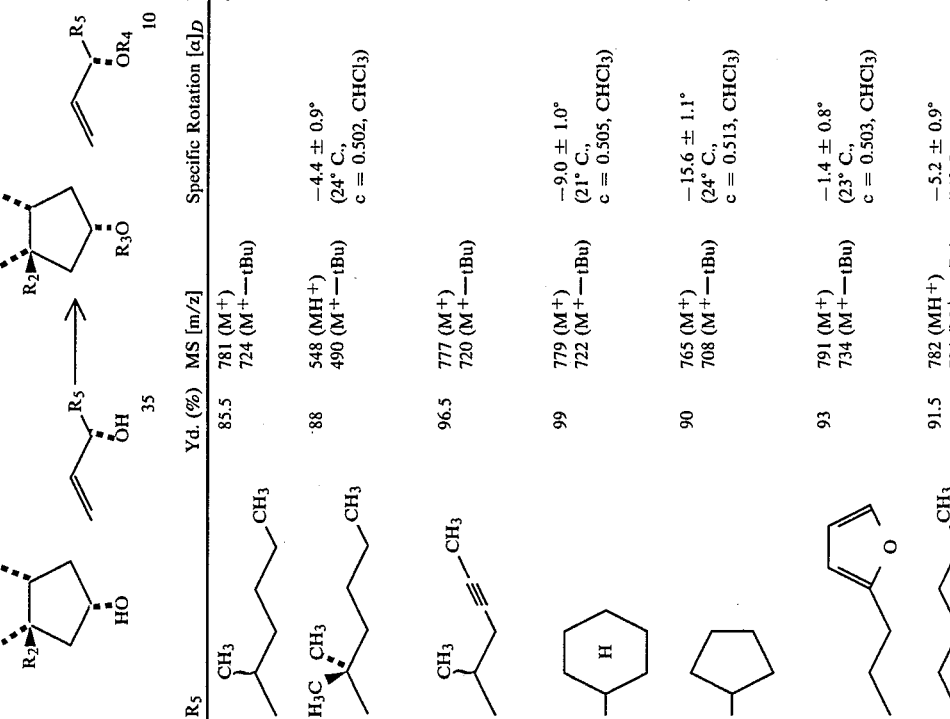

| Ex. No. | Compd. No. | $R_2$ | $R_3, R_4$ | $R_5$ | Yd. (%) | MS [m/z] | Specific Rotation $[\alpha]_D$ | IR $\nu$max [cm$^{-1}$] | NMR $\delta$ppm |
|---|---|---|---|---|---|---|---|---|---|
| I-90 | 10(S)g-b | CH≡C— | tBuPh$_2$Si— | (CH(CH$_3$)CH$_2$CH$_2$CH$_3$) | 85.5 | 781 (M$^+$) 724 (M$^+$—tBu) | | (CHCl$_3$) 3432, 3312, 1699, 1592, 1113 | (CDCl$_3$) 0.8 (6H,m), 1.02 (18H,s), 2.31 (1H,s), 3.98 (2H,m), 5.22 (2H,m), 6.44 (1H,s), 7.15~7.7 (20H,m) |
| I-92 | 10(R)g-c | CH≡C— | tBuMe$_2$Si— | (H$_3$C—C(CH$_3$)CH$_2$CH$_2$CH$_3$) | 88 | 548 (MH$^+$) 490 (M$^+$—tBu) | −4.4 ± 0.9° (24° C., c = 0.502, CHCl$_3$) | (CHCl$_3$) 3432, 3312, 1699, 1256, 1118, 1090, 1069, 859, 837 | (CDCl$_3$) −0.02 (3H,s), 0.03 (3H, s), 0.05 (6H,s), 0.77 (3H,s), 0.81 (3H, s), 0.86 (9H,s), 0.89 (9H,s), 2.46 (1H,s), 3.74 (1H,d,J=5.5Hz), 4.10 (1H,m), 5.51 (2H,m), 7.08 (1H,s) |
| I-94 | 10(S)g-d | CH≡C— | tBuPh$_2$Si— | (CH(CH$_3$)CH$_2$C≡CCH$_3$) | 96.5 | 777 (M$^+$) 720 (M$^+$—tBu) | | (CHCl$_3$) 3432, 3312, 1700, 1592, 1113 | (CDCl$_3$) 0.85 (3H,m), 0.99 (9H,s), 1.01 (9H,s), 1.73 (3H), 2.32 (1H,s), 3.9 (1H,m), 4.07 (1H,m), 5.15 (2H,s), 6.45 (1H,s), 7.15~7.75 (20H,m) |
| I-96 | 10(S)g-e | CH≡C— | tBuPh$_2$Si— | cyclohexyl | 99 | 779 (M$^+$) 722 (M$^+$—tBu) | −9.0 ± 1.0° (21° C., c = 0.505, CHCl$_3$) | (CHCl$_3$) 3432, 3312, 1700, 1591, 1113 | (CDCl$_3$) 1.02 (18H,s), 2.31 (1H,s), 3.90 (2H,m), 5.06 (1H,d-d,J=5, 15.5Hz), 5.29 (1H,d-d,J=6, 15.5Hz), 6.49 (1H,s), 7.15~7.7 (20H,m) |
| I-98 | 10(S)g-f | CH≡C— | tBuPh$_2$Si— | cyclopentyl | 90 | 765 (M$^+$) 708 (M$^+$—tBu) | −15.6 ± 1.1° (24° C., c = 0.513, CHCl$_3$) | (CHCl$_3$) 3432, 3312, 1698, 1592, 1113 | (CDCl$_3$) 1.01 (18H,s), 2.32 (1H,s), 3.92 (2H,m), 5.04 (1H,d-d,J=5.5, 15.5Hz), 5.29 (1H,d-d,J=6, 15.5Hz), 6.54 (1H,s), 7.2~7.7 (20H,m) |
| I-100 | 10(S)g-g | CH≡C— | tBuPh$_2$Si— | (furyl-propyl) | 93 | 791 (M$^+$) 734 (M$^+$—tBu) | −1.4 ± 0.8° (23° C., c = 0.503, CHCl$_3$) | (CHCl$_3$) 3432, 3312, 1700, 1592, 1113 | (CDCl$_3$) 1.00 (9H,s), 1.03 (9H,s), 2.32 (1H,s), 4.05 (2H,m), 5.25 (2H, m), 5.78 (1H), 6.20 (1H), 6.66 (1H, s), 7.2~7.7 (21H,m) |
| I-102 | 10(S)h | CH$_3$—C≡C— | tBuPh$_3$Si— | (CH$_2$CH$_2$CH$_2$CH$_2$CH$_3$) | 91.5 | 782 (MH$^+$) 724 (M$^+$—tBu) | −5.2 ± 0.9° (21° C., c = 0.500, CHCl$_3$) | (CHCl$_3$) 3432, 1693, 1590, 1111 | (CDCl$_3$) 0.80 (3H), 1.01 (9H,s), 1.03 (9H,s), 1.71 (3H,s), 4.05 (2H,m), 5.31 (2H,m), 6.06 (1H,m), 7.25~7.75 (20H,m) |

TABLE 6-continued

[Reaction scheme: structure with HN-R₂, OH, R₅ → structure with HN-R₂, OR₄, R₅ (with C=O, R₃O groups)]

| Ex. No. | Compd. No. | R₂ | R₃, R₄ | R₅ | Yd. (%) | MS [m/z] | Specific Rotation [α]_D | IR νmax [cm⁻¹] | NMR δppm |
|---|---|---|---|---|---|---|---|---|---|
| I-104 | 10(S)h-b | CH₃—C≡C— | tBuPh₂Si— | CH₃ / CH₃ (isohexyl chain) | 96 | | | (CHCl₃) 3432, 1696, 1592, 1113 | (CDCl₃) 0.78 (6H,m), 1.03 (9H,s), 1.06 (9H,s), 1.69 (3H,s), 3.98 (2H,m), 4.95~5.51 (2H,m), 6.58 (1H,s), 7.2~7.75 (20H,m) |
| I-106 | 10(S)h-c | CH₃—C≡C— | tBuPh₂Si— | (cyclohexyl with H) | 86 | 793 (MH⁺) 736 (M⁺—tBu) | −3.8 ± 0.9° (24° C., c = 0.500, CHCl₃) | (CHCl₃) 3432, 1696, 1591, 1112 | (CDCl₃) 1.00 (9H,s), 1.02 (9H,s), 1.71 (3H,s), 3.92 (2H,m), 5.20 (2H,m), 6.27 (1H,s), 7.2~7.7 (20H,m) |
| I-108 | 10(S)l-d | CH₂=CH— | tBuPh₂Si— | CH₃ (with pentynyl chain, C≡C-CH₃) | 94.5 | 779 (MH⁺) 722 (M⁺—tBu) | | (CHCl₃) 3432, 1695, 1591, 1113 | (CDCl₃) 0.87 (3H,m), 1.02 (18H,m), 1.72 (3H), 3.85 (1H,m), 4.11 (1H,m), 4.79~5.72 (5H,m), 6.76 (1H,s), 7.18~7.75 (20H,m) |

TABLE 7

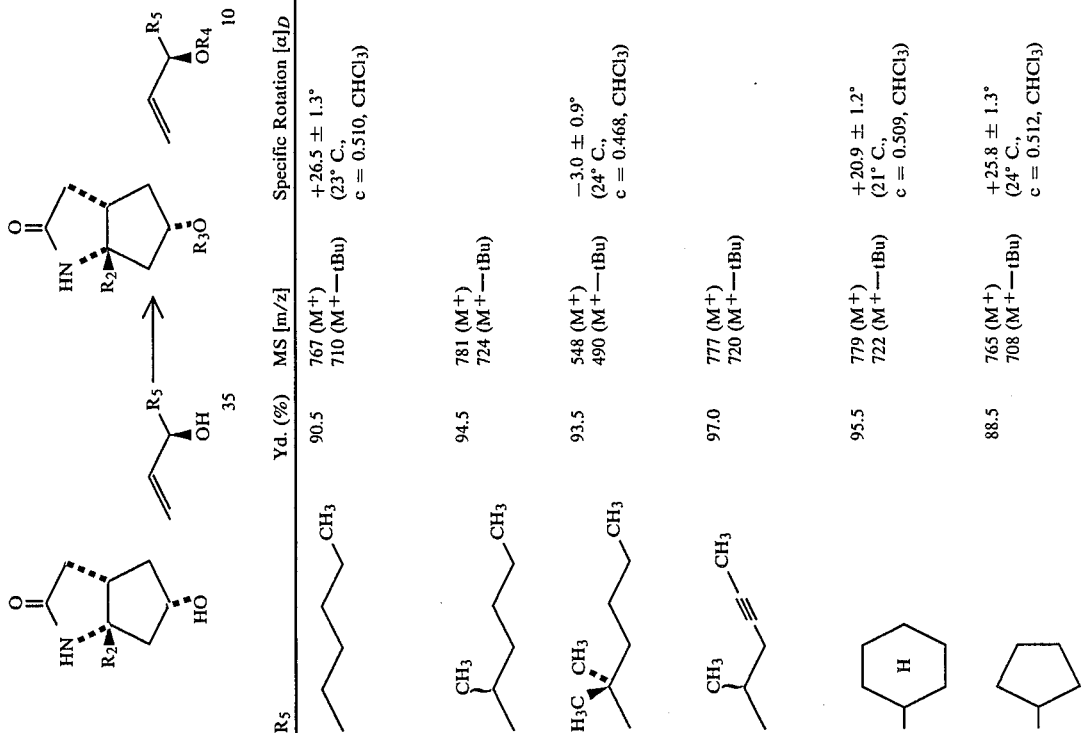

| Ex. No. | Compd. No. | R₂ | R₃, R₄ | R₅ | Yd. (%) | MS [m/z] | Specific Rotation [α]$_D$ | IR ν$_{max}$ [cm$^{-1}$] | NMR δppm |
|---|---|---|---|---|---|---|---|---|---|
| I-89 | 10(R)g | CH≡C— | tBuPh₂Si— | (n-pentyl) | 90.5 | 767 (M⁺) 710 (M⁺—tBu) | +26.5 ± 1.3° (23° C., c = 0.510, CHCl₃) | (CHCl₃) 3432, 3312, 1701, 1592, 1113 | (CDCl₃) 0.82 (3H), 0.99 (9H,s), 1.01 (9H,s), 2.31 (1H,s), 3.97 (2H,m), 4.86 (1H,d-d,J=7, 15Hz), 5.37 (1H,d-d,J=7.5, 15Hz), 6.72 (1H,s), 7.2~7.75 (20H,m) |
| I-91 | 10(R)g-b | CH≡C— | tBuPh₂Si— | (isohexyl with CH₃) | 94.5 | 781 (M⁺) 724 (M⁺—tBu) | | (CHCl₃) 3432, 3312, 1700, 1592, 1113 | (CDCl₃) 0.8 (6H,m), 0.99 (9H,s), 1.01 (9H,s), 2.32 (1H,s), 3.92 (2H,m), 4.87 (1H,m), 5.35 (1H,m), 6.48 (1H,s), 7.15~7.75 (20H,m) |
| I-93 | 10(S)g-c | CH≡C— | tBuMe₂Si— | (H₃C CH₃ branched) | 93.5 | 548 (M⁺) 490 (M⁺—tBu) | −3.0 ± 0.9° (24° C., c = 0.468, CHCl₃) | (CHCl₃) 3432, 3312, 1699, 1256, 1120, 1069, 868, 837 | (CDCl₃) −0.02 (3H,s), 0.02 (3H,s), 0.04 (6H,m), 0.77 (3H,s), 0.80 (3H,s), 0.86 (9H,s), 0.88 (9H,s), 2.46 (1H,s), 3.72 (1H,d,J=6.5Hz), 4.07 (1H,m), 5.48 (2H,m), 7.10 (1H,s) |
| I-95 | 10(R)g-d | CH≡C— | tBuPh₂Si— | (CH₃ branched alkyne) | 97.0 | 777 (M⁺) 720 (M⁺—tBu) | | (CHCl₃) 3432, 3312, 1700, 1592, 1113 | (CDCl₃) 0.87 (3H,m), 0.97 (9H,s), 0.99 (9H,s), 1.75 (3H), 2.32 (1H,s), 3.83 (1H,m), 4.1 (1H,m), 4.8 (1H,m), 5.3 (1H,m), 6.36 (1H,s), 7.15~7.75 (20H,m) |
| I-97 | 10(R)g-e | CH≡C— | tBuPh₂Si— | (cyclohexyl) | 95.5 | 779 (M⁺) 722 (M⁺—tBu) | +20.9 ± 1.2° (21° C., c = 0.509, CHCl₃) | (CHCl₃) 3432, 3312, 1591, 1113 | (CDCl₃) 0.99 (9H,s), 1.01 (9H,s), 2.31 (1H,s), 3.85 (2H,m), 4.77 (1H, d-d, J=7.5, 15.5Hz), 5.34 (1H,d-d,J=8, 15.5Hz), 6.51 (1H,s), 7.15~7.7 (20H,m) |
| I-99 | 10(R)g-f | CH≡C— | tBuPh₂Si— | (cyclopentyl) | 88.5 | 765 (M⁺) 708 (M⁺—tBu) | +25.8 ± 1.3° (24° C., c = 0.512, CHCl₃) | (CHCl₃) 3432, 3312, 1700, 1592, 1113 | (CDCl₃) 0.97 (9H,s), 1.00 (9H,s), 2.31 (1H,s), 3.88 (2H,m), 4.74 (1H,d-d,J=7.5, 15.5Hz), 5.32 (1H,d-d,J=8.5, 15.5Hz), 6.46 (1H,s), 7.2~7.7 (20H,m) |

TABLE 7-continued

[Reaction scheme: starting material with HN-R₂, cyclopentane-fused lactam with OH and R₅ group with OH → product with R₃O and OR₄ groups]

| Ex. No. | Compd. No. | R₂ | R₃, R₄ | R₅ | Yd. (%) | MS [m/z] | Specific Rotation [α]_D | IR νmax [cm⁻¹] | NMR δppm |
|---|---|---|---|---|---|---|---|---|---|
| I-101 | 10(R)g-g | CH≡C— | tBuPh₂Si— | (furyl-propyl) | 93 | 791 (M⁺), 734 (M⁺—tBu) | +20.6 ± 1.2° (23° C., c = 0.509, CHCl₃) | (CHCl₃) 3432, 3312, 1700, 1592, 1113 | (CDCl₃) 0.98 (9H,s), 1.01 (9H,s), 2.32 (1H,s), 3.90 (1H,m), 4.10 (1H,m), 4.86 (1H,d-d,J=7, 16Hz), 5.36 (1H,d-J=7.5, 16Hz), 5.81 (1H), 6.23 (1H), 6.71 (1H,s), 7.15~7.7 (21H,m) |
| I-103 | 10(R)h | CH₃—C≡C— | tBuPh₂Si— | (n-hexyl) | 96 | 781 (M⁺), 724 (M⁺—tBu) | +31.2 ± 1.4° (23° C., c = 0.513, CHCl₃) | (CHCl₃) 3432, 1697, 1591, 1113 | (CDCl₃) 0.82 (3H), 0.99 (9H,s), 1.02 (9H,s), 1.72 (3H,s), 3.96 (2H,m), 4.90 (1H,d-d,J=8, 16Hz), 5.37 (1H, d-d,J=7, 16Hz), 6.56 (1H,s), 7.14~7.8 (20H,m) |
| I-105 | 10(R)h-b | CH₃—C≡C— | tBuPh₂Si— | (isohexyl) | 97 |  |  | (CHCl₃) 3432, 1695, 1592, 1113 | (CDCl₃) 0.8 (6H,m), 1.02 (9H,s), 1.05 (9H,s), 1.73 (3H,s), 3.91 (2H,m), 4.69~5.13 (1H,m), 5.22-5.58 (1H,m), 6.49 (1H,s), 7.2~7.75 (20H,m) |
| I-107 | 10(R)h-c | CH₃—C≡C— | tBuPh₂Si— | (cyclohexyl) | 82.5 | 793 (M⁺), 736 (M⁺—tBu) | +25.7 ± 1.3° (24° C., c = 0.505, CHCl₃) | (CHCl₃) 3432, 1695, 1591, 1113 | (CDCl₃) 0.98 (9H,s), 1.01 (9H,s), 1.72 (3H,s), 3.85 (2H,m), 4.80 (1H, d-J=7.5, 16Hz), 5.35 (1H,d-d,J=8, 16Hz), 6.23 (1H,s), 7.2~7.7 (20H,m) |
| I-109 | 10(R)l-d | CH₂=CH— | tBuPh₂Si— | (isopentynyl) | 96.5 | 779 (M⁺), 722 (M⁺—tBu) |  | (CHCl₃) 3432, 1696, 1591, 1113 | (CDCl₃) 0.95 (3H,m), 1.00 (18H,s), 1.70 (3H), 3.75 (1H,m), 4.15 (1H,m), 4.62~5.04 (3H,m), 5.16~5.72 (2H,m), 6.39 (1H,s), 7.15~7.76 (20H,m) |

Example I-110

Preparation of
1-ethenyl-2-aza-3-oxo-6-[(3S)-3-tert-butyldiphenyl-silyloxy-4-methyl-oct-1-enyl]-7-tert-butyldiphenyl-silyloxybicyclo[3.3.0.]octane 10(S)l-b

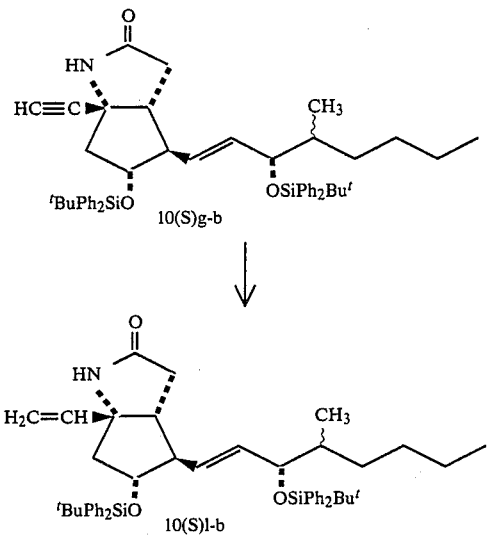

To a solution of 466 mg of the ethynyl-lactam 10(S)g-b (Example I-90) in 47 ml of benzene are added 0.47 ml of quinoline and 23 mg of 5% palladium-barium sulfate and the mixture is stirred in an atmosphere of hydrogen at atmospheric pressure and ordinary temperature for 1 hour. The insoluble material is filtrated off and the filtrate is evaporated. The residue is dissolved in ethyl acetate and the solution is washed with 1N hydrochloric acid, water, dilute aqueous solution of sodium hydrogencarbonate, and saturated aqueous solution of sodium chloride, successively, dried over anhydrous magnesium sulfate, and evaporated to give 480 mg of residue, which is purified by column chromatography (Lober column, size B; eluted with toluene:ethyl acetate=6:1) to give 409 mg of the compound 10(S)l-b as a foamy material (87.5% yield).

MS: m/z 783 (M+), m/z 726 (M+ − $^t$Bu).
$[\alpha]_D^{23}$ −23.7±1.3° (c=0.510, CHCl$_3$).
IR: $\nu_{max}^{CHCl_3}$ 3432, 1694, 1591, 1113 cm$^{-1}$.
NMR: $\delta_{ppm}^{CDCl_3}$ 0.76 (6H, m), 1.02 (18H, s), 3.98 (2H, m), 4.76–5.73 (5H, m), 6.23 (1H, s), 7.2–7.7 (20H, m).

Example I-111–113, 137 and 138

The catalytic hydrogenation is carried out in the same manner as in Example I-110 and the results are shown in Tables 8 and 9.

TABLE 8

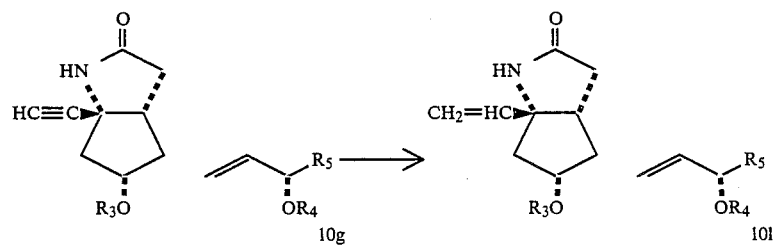

| Ex. Number | Compd. Number | R$_3$, R$_4$ | R$_5$ | Yd. (%) | MS [m/z] | Specific Rotation [α]$_D$ | IR νmax [cm$^-$] | NMR δppm |
|---|---|---|---|---|---|---|---|---|
| I-112 | 10(S) l-f | tBuPh$_2$Si— | cyclopentyl | 92.5 | 767 (M+) 710 (M+ −tBu) | −33.7 ± 1.5° (23° C., c = 0.50, CHCl$_3$) | (CHCl$_3$) 3432, 1693, 1591, 1113 | (CDCl$_3$) 1.02 (18H,s), 3.90 (2H,m), 4.80~5.74 (5H,m), 6.60 (1H,s), 7.18~7.79 (20H,m) |
| I-137 | 10(S) l-e | tBuPh$_2$Si— | cyclohexyl | 86.5 | | −25.3 ± 1.3° (23° C., c = 0.507, CHCl$_3$) | (CHCl$_3$) 3432, 1695, 1591, 1113 | (CDCl$_3$) 1.02 (18H,s), 3.90 (2H,m), 4.76~5.7 (5H,m), 6.30 (1H,s), 7.2~7.75 (20H,m) |

TABLE 9

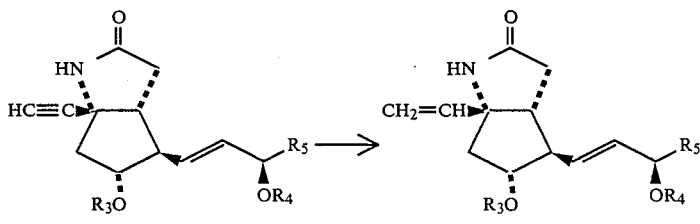

| Ex. Number | Compd. Number | R$_3$, R$_4$ | R$_5$ | Yd. (%) | MS [m/z] | Specific Rotation [α]$_D$ |
|---|---|---|---|---|---|---|

TABLE 9-continued

| | | | 10g | | 101 |
|---|---|---|---|---|---|
| I-111 | 10(R) 1-b | tBuPh₂Si— | CH₃-CH(CH₃)-CH₂-CH₂- | 87.5 | 784 (MH⁺) 726 (M⁺—tBu) |
| I-113 | 10(R) 1-f | tBuPh₂Si— | cyclopentyl | 92 | 767 (M⁺) 710 (M⁺—tBu)  +9.8 ± 1.0° (23° C., c = 0.50, CHCl₃) |
| I-138 | 10(R) 1-e | tBuPh₂Si— | cyclohexyl-H | 89.5 | |

| Ex. Number | IR νmax [cm⁻¹] | NMR δppm |
|---|---|---|
| I-111 | (CHCl₃) 3432, 1696, 1591, 1113 | (CDCl₃) 0.82 (6H,m), 1.01 (18H,s), 3.90 (2H,m), 4.67~5.10 (3H,m), 5.22~5.76 (2H,m), 6.45 (1H,s), 7.2~7.73 (20H,m) |
| I-113 | (CHCl₃) 3432, 1695, 1591, 1112 | (CDCl₃) 1.00 (18H,s), 3.86 (2H,m), 4.6~5.06 (3H,m), 5.2~5.7 (2H,m), 6.55 (1H,s), 7.2~7.8 (20H,m) |
| I-138 | | (CDCl₃) 1.00 (18H,s), 3.80 (2H,m), 4.6~5.0 (3H,m), 5.2~5.7 (2H,m), 6.18 (1H,s), 7.15~7.75 (20H,m) |

Example I-114

Preparation of 1-ethynyl-2-aza-3-thioxo-6-[(3S)-3-tert-butyldiphenyl-silyloxyoct-1-enyl]-7-tert-butyldiphenylsilyloxybicy-clo[3.3.0.]octane 13(S)g

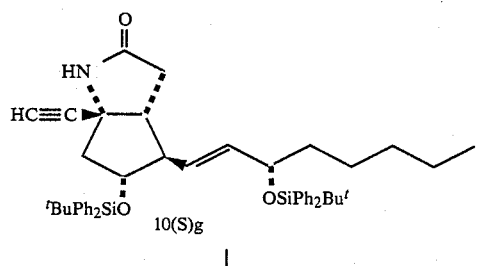

10(S)g

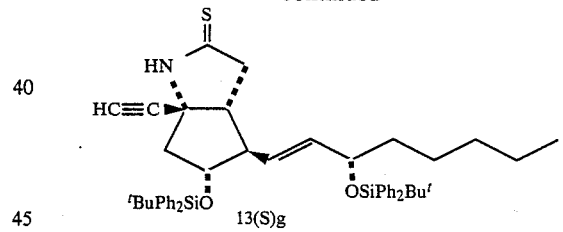

13(S)g

To a solution of 140 mg (0.182 mmol) of the lactam 10(S)g in 7 ml of dry benzene are added 587 mg (7.42 mmol) of pyridine and 370 mg (0.916 mmol) of Lawesson's Reagent in an atmosphere of nitrogen and the mixture is stirred on an oil bath at 70° C. for 1 hour and 15 minutes. After cooling, the reaction mixture is directly purified by column chromatography (15 g of silica gel; eluted with benzene) to give 141 mg of the compound 13(S)g as a foamy material (98.5% yield).

MS: m/z 784 (MH⁺), m/z 726 (M⁺ − ᵗBu).
$[\alpha]_D^{23}$ −10.1±1.0° (c=0.514, CHCl₃).
IR: $\nu_{max}^{CHCl_3}$ 3404, 3308, 1590, 1472, 1112 cm⁻¹.
NMR: $\delta_{ppm}^{CDCl_3}$ 0.80 (3H), 1.01 (18H, s), 2.42 (1H, s), 4.05 (2H, m), 5.27 (2H, m), 7.2–7.75 (20H, m), 7.85 (1H, s).

Example I-115~136 and 139–141

The conversion of the lactam into the thio-lactam is carried out in the same manner as in Example I-114 and the results are shown in Tables 10 and 11.

TABLE 10

$$10 \longrightarrow 13$$

| Ex. No. | Compound Number | R₂ | R₃, R₄ | R₅ | Yd. (%) | MS [m/z] | Specific Rotation [α]_D | IR νmax [cm⁻¹] | NMR δppm |
|---|---|---|---|---|---|---|---|---|---|
| I-116 | 13(S)g-b | CH≡C— | tBuPh₂Si— | CH₃ (isobutyl) | 98.5 | 797 (M⁺) 740 (M⁺—tBu) | | (CHCl₃) 3404, 3312, 1591, 1487, 1474, 1112 | (CDCl₃) 0.8 (6H,m), 1.03 (18H,s), 2.42 (1H,s), 3.97 (2H,m), 5.18 (2H,m), 7.15~7.7 (20H,m), 7.99 (1H,s) |
| I-118 | 13(R)g-c | CH≡C— | tBuMe₂Si— | H₃C CH₃ | 96 | 563 (M⁺) 506 (M⁺—tBu) | +11.2 ± 1.2° (24° C., c = 0.429, CHCl₃) | (CHCl₃) 3404, 3312, 1473, 1256, 1146, 1116, 1079, 837 | (CDCl₃) −0.02 (3H,s), 0.02 (3H,s), 0.05 (6H,s), 0.77 (3H,s), 0.81 (3H,s), 0.87 (9H,s), 0.90 (9H,s), 2.56 (1H,s), 3.72 (1H,d,J=5.5Hz), 4.08 (1H,m), 5.49 (2H,m), 8.54 (1H,s) |
| I-120 | 13(S)g-d | CH≡C— | tBuPh₂Si— | CH₃ (propargyl) | 98.5 | 793 (M⁺) 736 (M⁺—tBu) | | (CHCl₃) 3404, 3312, 1591, 1486, 1473, 1112 | (CDCl₃) 0.85 (3H,m), 1.02 (18H,s), 1.72 (3H), 2.43 (1H,s), 3.9 (1H,m), 4.07 (1H,m), 5.12 (2H,m), 7.2~7.7 (20H,m), 8.10 (1H,s) |
| I-122 | 13(S)g-e | CH≡C— | tBuPh₂Si— | cyclohexyl | 99.5 | 795 (M⁺) 738 (M⁺—tBu) | −13.7 ± 1.1° (21° C. c = 0.507, CHCl₃) | (CHCl₃) 3404, 3312, 1591, 1487, 1474, 1113 | (CDCl₃) 1.02 (18H,s), 2.42 (1H,s), 3.90 (2H,m), 5.02 (1H,d-d,J=6, 15.5Hz), 5.28 (1H,d-d,J=6, 15.5Hz), 7.15~7.7 (20H,m), 8.14 (1H,s) |
| I-124 | 13(S)g-g | CH≡C— | tBuPh₂Si— | furyl | 98.5 | 807 (M⁺) 750 (M⁺—tBu) | 0° (23° C., c = 0.500, CHCl₃) | (CHCl₃) 3404, 3312, 1591, 1485, 1474, 1113 | (CDCl₃) 1.03 (18H,s), 2.42 (1H,s), 3.95 (1H,m), 4.13 (1H,m), 5.20 (2H,m), 5.77 (1H), 6.20 (1H), 7.2~7.7 (21H,m), 8.17 (1H,s) |
| I-126 | 13(S)h-b | CH₃—C≡C— | tBuPh₂Si— | CH₃ (isobutyl) | 93 | | | (CHCl₃) 3404, 1592, 1489, 1474, 1113 | (CDCl₃) 0.78 (6H,m), 1.03 (18H,s), 1.72 (3H,s), 3.96 (2H,m), 4.90~5.46 (2H,m), 7.2~7.7 (20H,m), 8.37 (1H,s) |
| I-128 | 13(S)h-e | CH₃—C≡C— | tBuPh₂Si— | cyclohexyl | 95 | 809 (M⁺) 752 (M⁺—tBu) | −12.4 ± 1.1° (24° C., c = 0.500, CHCl₃) | (CHCl₃) 3404, 1591, 1488, 1474, 1113 | (CDCl₃) 1.02 (18H,s), 1.72 (3H), 3.90 (2H,m), 5.04 (1H,d-d,J=5.5, 16Hz), 5.29 (1H,d-d,J=6, 16Hz), 7.2~7.7 (20H,m), 7.98 (1H,s) |

TABLE 10-continued

[Reaction scheme: compound 10 (ketone, C=O on bicyclic system with HN-R₂, R₃O, and side chain with OR₄ and R₅) → compound 13 (thioketone, C=S analog)]

| Ex. No. | Compound Number | R₂ | R₃, R₄ | R₅ | Yd. (%) | MS [m/z] | Specific Rotation [α]$_D$ | IR νmax [cm$^{-1}$] | NMR δppm |
|---|---|---|---|---|---|---|---|---|---|
| I-130 | 13(S)1-b | CH₂=CH— | tBuPh₂Si— | —CH(CH₃)—CH₂CH₂CH₂—CH₃ | 95 | 799 (M⁺) 742 (M⁺—tBu) | | (CHCl₃) 3404, 1591, 1487, 1474, 1113 | (CDCl₃) 0.76 (6H,m), 1.02 (18H,s), 3.91 (2H,m), 4.80~5.73 (5H,m), 7.2~7.76 (20H,m), 8.34 (1H,s) |
| I-132 | 13(S)1-d | CH₂=CH— | tBuPh₂Si— | —CH(CH₃)—CH₂—C≡C—CH₃ | 96.5 | 795 (M⁺) 738 (M⁺—tBu) | | (CHCl₃) 3404, 1591, 1486, 1473, 1113 | (CDCl₃) 0.84 (3H,m), 1.00 (18H,s), 1.72 (3H), 3.82 (1H,m), 4.11 (1H,m), 4.81~5.71 (5H,m), 7.22~7.77 (20H,m), 8.47 (1H,s) |
| I-134 | 13(S)1-f | CH₂=CH— | tBuPh₂Si— | cyclopentyl | 100 | 783 (M⁺) 726 (M⁺—tBu) | −25.0 ± 1.3° (24° C., c = 0.50, CHCl₃) | (CHCl₃) 3404, 1591, 1488, 1473, 1113 | (CDCl₃) 1.02 (18H,s), 3.88 (2H,m), 4.79~5.70 (5H,m), 7.2~7.72 (20H,m), 8.43 (1H,s) |
| I-136 | 13(S)g-f | CH≡C— | tBuPh₂Si— | cyclopentyl | 98.5 | | −19.8 ± 1.2° (22° C., c = 0.506, CHCl₃) | (CHCl₃) 3404, 3312, 1591, 1488, 1474, 1112 | (CDCl₃) 1.01 (18H,s), 2.43 (1H,m), 3.90 (2H,m), 4.98 (1H,d,J=6, 16 Hz), 5.26 (1H,d-d,J=7, 16Hz), 7.2~7.75 (20H,m), 8.10 (1H,s) |
| I-140 | 13(S)1-e | CH₂=CH— | tBuPh₂Si— | cyclohexyl | 100 | | −17.3 ± 1.1° (23° C., c = 0.503, CHCl₃) | (CHCl₃) 3404, 1591, 1487, 1113 | (CDCl₃) 1.02 (18H,s), 3.88 (2H,m), 4.8~5.73 (5H,m), 7.15~7.75 (20H,m), 8.26 (1H,s) |

TABLE 11

| Ex. No. | Compound Number | R₂ | R₃, R₄ | R₅ | Yd. (%) | MS [m/z] | Specific Rotation [α]_D | IR νmax [cm⁻¹] | NMR δppm |
|---|---|---|---|---|---|---|---|---|---|
| I-115 | 13(R)g | CH≡C— | tBuPh₂Si— | (n-pentyl chain) | 95 | 783 (M⁺) 726 (M⁺—tBu) | +29.0 ± 1.3° (23° C., c = 0.517, CHCl₃) | (CDCl₃) 3404, 3312, 1592, 1487, 1474, 1113, 1106 | (CDCl₃) 0.82 (3H), 1.02 (18H,s), 2.42 (1H,s), 3.77~4.15 (2H,m), 4.82 (1H,d-d,J=8, 16Hz), 5.32 (1H,d-d, J=7, 16Hz), 7.23~7.7 (20H,m), 8.41 (1H,s) |
| I-117 | 13(R)g-b | CH≡C— | tBuPh₂Si— | (isohexyl) | 99.5 | 797 (M⁺) 740 (M⁺—tBu) | | (CHCl₃) 3404, 3312, 1591, 1487, 1474, 1113 | (CDCl₃) 0.81 (6H,m), 1.01 (18H,s), 2.43 (1H,s), 3.88 (2H,m), 4.8 (1H, m), 5.3 (1H,m), 7.2~7.7 (20H,m), 8.04 (1H,s) |
| I-119 | 13(S)g-c | CH≡C— | tBuMe₂Si— | (chiral methyl branched) | 96.5 | 563 (M⁺) 506 (M⁺—tBu) | +17.7 ± 1.4° (24° C., c = 0.423, CHCl₃) | (CHCl₃) 3404, 3312, 1473, 1257, 1147, 1120, 1077, 868, 837 | (CDCl₃) −0.02 (3H,s), 0.02 (3H,s), 0.05 (6H,s), 0.78 (3H,s), 0.80 (3H, s), 0.87 (9H,s), 0.89 (9H,s), 2.56 (1H,s), 3.69 (1H,d,J=6.5Hz), 4.05 (1H,m), 5.47 (2H,m), 8.63 (1H,s) |
| I-121 | 13(R)g-d | CH≡C— | tBuPh₂Si— | (methyl propargyl branched) | 99 | 793 (M⁺) 736 (M⁺—tBu) | | (CHCl₃) 3404, 3312, 1591, 1486, 1474, 1113 | (CDCl₃) 0.88 (3H,m), 0.99 (18H,s), 1.76 (3H), 2.42 (1H,s), 3.8 (1H,m), 4.07 (1H,m), 4.75 (1H,m), 5.25 (1H, m), 7.2~7.75 (20H,m), 8.11 (1H,s) |
| I-123 | 13(R)g-e | CH≡C— | tBuPh₂Si— | (cyclohexyl) | 99.5 | 795 (M⁺) 738 (M⁺—tBu) | +23.3 ± 1.3° (21° C., c = 0.506, CHCl₃) | (CHCl₃) 3404, 3312, 1591, 1485, 1474, 1112 | (CDCl₃) 1.01 (18H,s), 2.42 (1H,s), 3.81 (2H,m), 4.72 (1H,d-d,J=7.5, 15.5Hz), 5.29 (1H,d-d,J=8, 15.5Hz), 7.15~7.7 (20H,m), 8.15 (1H,s) |
| I-125 | 13(R)g-g | CH≡C— | tBuPh₂Si— | (furyl propyl) | 98.5 | 807 (M⁺) 750 (M⁺—tBu) | +23.8 ± 1.2° (23° C., c = 0.516, CHCl₃) | (CHCl₃) 3404, 3312, 1592, 1485, 1474, 1113 | (CDCl₃) 1.00 (9H,s), 1.03 (9H,s), 2.43 (1H,s), 3.86 (1H,m), 4.08 (1H, m), 4.80 (1H,d-d,J=7, 16Hz), 5.30 (1H,d-d,J=7.5, 16Hz), 5.80 (1H), 6.23 (1H), 7.2~7.7 (21H,m), 8.17 (1H,s) |

Scheme: Compound 10 → Compound 13 (conversion of cyclopentane-fused pyrrolidinone C=O to C=S)

TABLE 11-continued

[Structure: starting material 10 (ketone, O) converting to product 13 (thione, S), both bearing HN-R2, R3O, OR4, R5 substituents on bicyclic framework]

| Ex. No. | Compound Number | R2 | R3, R4 | R5 | Yd. (%) | MS [m/z] | Specific Rotation [α]D | IR νmax [cm⁻¹] | NMR δppm |
|---|---|---|---|---|---|---|---|---|---|
| I-127 | 13(R)h-b | CH₃—C≡C— | tBuPh₂Si— | CH₃ (isohexyl, branched) | 95.5 | 812 (M⁺H) 754 (M⁺—tBu) | | (CHCl₃) 3404, 1592, 1488, 1473, 1113 | (CDCl₃) 0.8 (6H,m), 1.00 (18H,s), 1.73 (3H,s), 3.90 (2H,m), 4.65~5.1 (1H,m), 5.2~5.65 (1H,m), 7.15~7.8 (20H,m), 8.00 (1H,s) |
| I-129 | 13(R)h-e | CH₃—C≡C— | tBuPh₂Si— | cyclohexyl | 95 | 809 (M⁺) 752 (M⁺—tBu) | +25.4 ± 1.3° (24° C., c = 0.511, CHCl₃) | (CHCl₃) 3404, 1591, 1489, 1474, 1113 | (CDCl₃) 1.01 (18H,s), 1.71 (3H,s), 3.82 (2H,m), 4.75 (1H,d-d,J=7, 16Hz), 5.31 (1H,d-d,J=8, 16Hz), 7.2~7.7 (20H,m), 8.00 (1H,s) |
| I-131 | 13(R)l-b | CH₂=CH— | tBuPh₂Si— | CH₃ (isohexyl, branched) | 98 | 799 (M⁺) 742 (M⁺—tBu) | | (CHCl₃) 3404, 1591, 1486, 1474, 1113 | (CDCl₃) 0.80 (6H,m), 1.01 (18H,s), 3.80 (2H,m), 4.57~5.05 (3H,m), 5.16~5.75 (2H,m), 7.2~7.75 (20H,m), 8.33 (1H,s) |
| I-133 | 13(R)l-d | CH₂=CH— | tBuPh₂Si— | CH₃—(pentynyl) | 97.5 | 795 (M⁺) 738 (M⁺—tBu) | | (CHCl₃) 3404, 1591, 1486, 1474, 1113 | (CDCl₃) 0.91 (3H,m), 1.00 (18H,s), 1.77 (3H), 3.71 (1H,m), 4.12 (1H,m), 4.57~5.71 (5H,m), 7.25~7.75 (20H,m), 8.32 (1H,s) |
| I-135 | 13(R)l-f | CH₂=CH— | tBuPh₂Si— | cyclopentyl | 100 | 783 (M⁺) 726 (M⁺—tBu) | +22.0 ± 1.2° (24° C., c = 0.51, CHCl₃) | (CHCl₃) 3404, 1591, 1487, 1473, 1113 | (CDCl₃) 0.99 (18H,s), 3.80 (2H,m), 4.51~5.00 (3H,m), 5.16~5.68 (2H,m), 7.2~7.7 (20H,m), 8.24 (1H,s) |
| I-139 | 13(R)g-f | CH≡C— | tBuPh₂Si— | cyclopentyl | 95 | | +32.2 ± 1.4° (22° C., c = 0.512, CHCl₃) | (CHCl₃) 3404, 3312, 1591, 1488, 1474, 1112 | (CDCl₃) 1.00 (18H,s), 2.42 (1H,s), 3.85 (2H,m), 4.68 (1H,d-d,J=7.5, 15.5Hz), 5.26 (1H,d-d,J=8, 15.5Hz), 7.15–7.7 (20H,m), 7.99 (1H,s) |
| I-141 | 13(R)l-e | CH₂=CH— | tBuPh₂Si— | cyclohexyl | 100 | | | | (CDCl₃) 1.00 (18H,m), 3.80 (2H,m), 4.53–5.05 (3H,m), 5.16–5.7 (2H,m), 7.15–7.75 (20H,m), 8.21 (1H,s) |

EXAMPLE FOR THE PREPARATION OF THE COMPOUNDS OF THE PRESENT INVENTION

Example F-1

(1) Preparation of 1-phenylthio-2-aza-3-thioxo-6-[(3S)-3-tert-butyldiphenylsilyloxyoct-1-enyl]-7-tert-butyldiphenylsilyloxybicyclo[3.3.0]octane 13(S)a

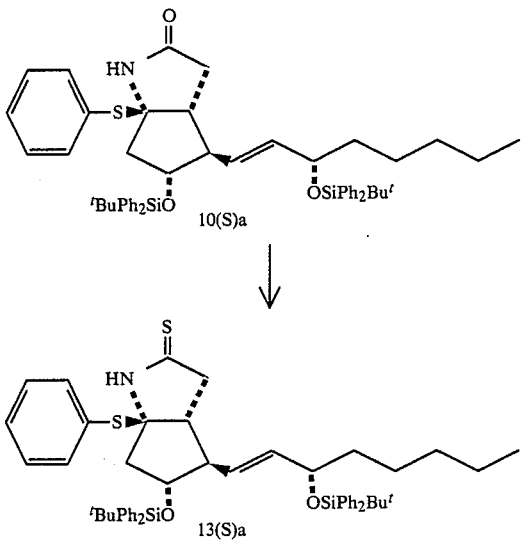

To a solution of 300 mg (0.352 mmol) of the phenylthio-lactam 10(S)a (Example I-7) in 20 ml of dry benzene is added 430 mg (1.065 mmol) of 2,4-bis(4-methoxyphenyl)-1,3-dithia-2,4-diphosphetane-2,4-disulfide (Lawesson's Reagent) and the mixture is stirred on an oil bath at 50° C. for 3 hours. After cooling, the reaction mixture is applied to column chromatography on silica gel (9 g; benzene) to give 305 mg of a residue, which further is purified by column chromatography (Lober column, size B; eluted with cyclohexane:ethyl acetate=30:1) to give 270 mg of the compound 13(S)a as a foamy material (88% yield).

MS: m/z 758 (M+ −PhS).

$[\alpha]_D$ −27.3±0.7° (23° C., c=1.005, CHCl$_3$).

IR: $\nu$max (CHCl$_3$) 3400, 3075, 3005, 1589, 1470, 1112 cm$^{-1}$.

NMR: δ ppm (CDCl$_3$) 0.80 (3H), 1.01 (9H, s), 1.05 (9H, s), 4.07 (2H, m), 5.34 (2H, m), 7.1–7.8 (25H, m), 8.28 (1H, s).

(2) Preparation of ethyl 4-[7-tert-butyldiphenylsilyloxy-6-[(3S)-3-tert-butyldiphenylsilyloxy-1-octenyl]-1-phenylthio-2-azabicyclo[3.3.0]oct-2-en-3-yl]thiobutanoate 15(S)a

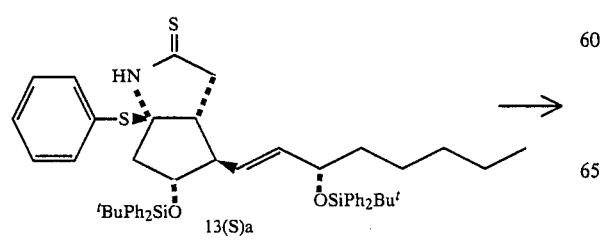

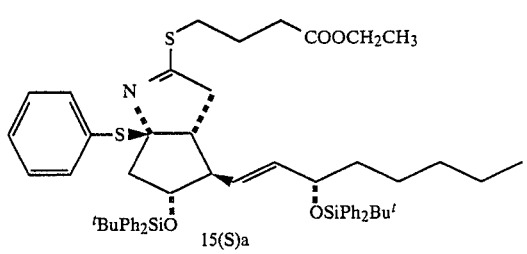

A solution of 270 mg (0.311 mmol) of the phenylthio-lactam 13(S)a (Example F-1-(1)) in 8 ml dry N,N-dimethylformamide is cooled in an ice water bath and 14 mg (0.344 mmol) of 59% sodium hydride is added thereto and the mixture is stirred for 1 hour in an atmosphere of nitrogen. Subsequently, 79 mg (0.405 mmol) of ethyl 4-bromobutyrate is added to the reaction mixture and the mixture is stirred at the same temperature for 40 minutes. The reaction mixture is poured into ice water and extracted 3 times with ethyl acetate. The extract is washed with water, dried over anhydrous magnesium sulfate, and evaporated to give 333 mg of a residue, which is purified by column chromatography (Lober column, size B; eluted with cyclohexane:ethyl acetate=25:1) to give 264 mg of the compound 15(S)a as an oil (86% yield).

MS: m/z 936 (M+ −OC$_2$H$_5$), m/z 924 (M+ −tBu), m/z 872 (M+ −PhS).

$[\alpha]_D$ −18.1∓1.6° (23° C., c=0.375, CHCl$_3$).

IR: $\nu$max (CHCl$_3$) 3075, 3005, 1730, 1590, 1572, 1112 cm$^{-1}$.

NMR: δ ppm (CDCl$_3$) 0.81 (3H), 1.00 (9H, s), 1.05 (9H, s), 1.25 (3H, t, J=7 Hz), 3.13 (2H, m), 4.03 (2H, m), 4.13 (2H, q, J=7 Hz), 5.33 (2H, m), 7.1–7.8 (25H, m).

Example F-2

(1) Preparation of 1-methoxy-2-aza-3-thioxo-6-[(3S)-3-tert-butyldiphenylsilyloxyoct-1-enyl]-7-tert-butyldiphenylsilyloxybicyclo[3.3.0]octane 13(S)b

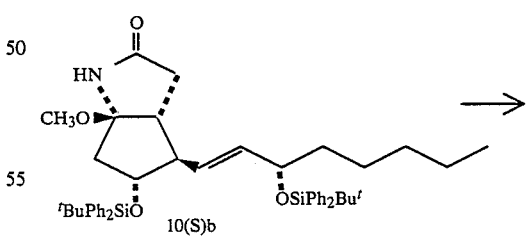

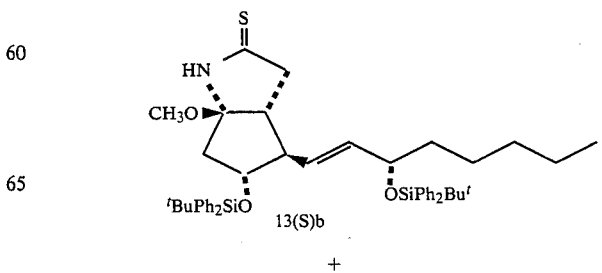

+

-continued

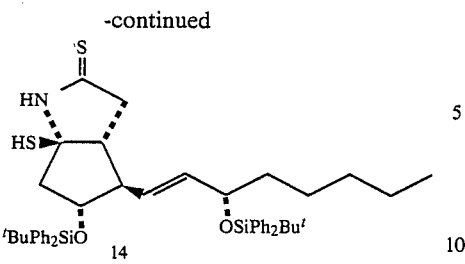

To a solution of 303 mg (0.392 mmol) of the methoxy-lactam 10(S)b (Example I-8) in 15 ml of dry benzene are added 1.27 g (16.07 mmol) of pyridine and 792 mg (1.96 mmol) of Lawesson's Reagent in an atmosphere of nitrogen and the mixture is stirred on an oil bath at 55° C. for five and half hours. After cooling, the reaction mixture is directly purified by column chromatography (30 g of silica gel; eluted with benzene~benzene:ethyl acetate=30:1~dichloromethane) to give 213 mg of the compound 13(S)b as a foamy material (69% yield) and 36 mg of 1-mercapto-2aza-3-thioxo-6-[(3S)-3-tert-butyl-diphenylsilyloxyoct-1-enyl]-7-tert-butyldiphenyl-silyloxybicyclo[3.3.0]octane 14 as a foamy material (12% yield).

Compound 13(S)b

MS: m/z 789 (M+), m/z 758 (M+ −OCH₃), m/z 732 (M+ −tBu).

[α]_D 0.0° (23° C., c=0.664, CHCl₃).

IR: νmax (CHCl₃) 3400, 3075, 3005, 1591, 1472, 1111 cm⁻¹.

NMR: δ ppm (CDCl₃) 0.81 (3H), 1.01 (9H, s), 1.03 (9H, s), 3.03 (3H, s), 4.01 (2H, m), 5.28 (2H, m), 7.1–7.8 (20H, m), 8.22 (1H, s).

Compound 14

MS: m/z 757 (M+ −H₂S), m/z 734 (M+ −tBu).

IR: νmax (CHCl₃) 3400, 3080, 3005, 1590, 1471, 1111 cm⁻¹.

NMR: δ ppm (CDCl₃) 0.81 (3H), 1.02 (9H, s), 1.04 (9H, s), 4.04 (2H, m), 5.27 (2H, m), 7.1–7.7 (20H, m), 8.32 (1H, s). [α]_D −21.8±0.8° (22.5° C., c=0.748, CHCl₃).

(2) Preparative of ethyl 4-[7-tert-butyldiphenylsilyloxy-6-[(3S)-3-tert-butyldi-phenylsilyloxy-1-octenyl]-1-methoxy-2-azabicyclo[3.3.-0]oct-2-en-3-yl]thiobutanoate 15(S)b

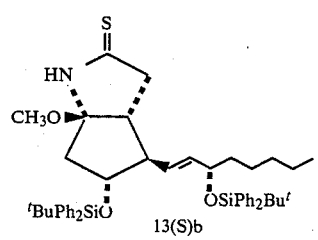

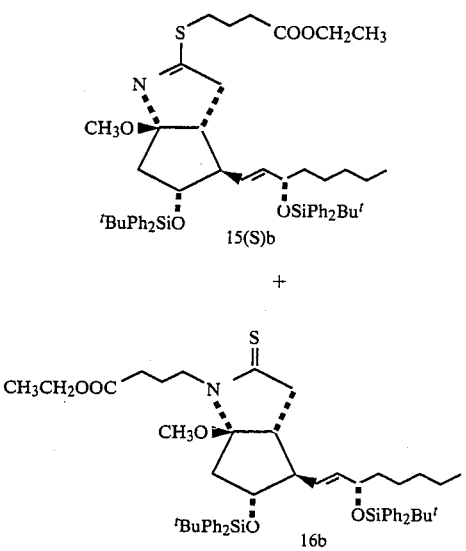

In the same manner as in Example F-1-(2), 254 mg of the methoxy-thiolactam 13(S)b (Example F-2-(1)) is alkylated to give 262 mg of the compound 15(S)b as an oil (90% yield) and 19 mg of ethyl 4-[7-tert-butyldi-phenylsilyloxy-6-[(3S)-3-tert-butyldiphenylsilyloxy-1-octenyl]-1-methoxy-3-thioxo-2-azabicyclo[3.3.0]oct-2-yl]butanoate 16(S)b as an oil (6.5% yield).

Compound 15(S)b

MS: m/z 904(MH+), m/z 872(M+ −OCH₃), m/z 858(M+ −OC₂H₅), m/z 846(M+ −tBu).

[α]_D +21.6±1.1° (23° C., c=0.541, CHCl₃).

IR: νmax (CHCl₃) 3075, 3005, 1729, 1590, 1582, 1111 cm⁻¹.

NMR: δ ppm (CDCl₃) 0.81 (3H), 1.00 (9H, s), 1.03 (9H, s), 1.23 (3H, t, J=7 Hz), 2.99 (3H, s), 3.07 (2H, m), 3.95 (2H, m), 4.11 (2H, q, J=7 Hz), 5.28 (2H, m), 7.1–7.8 (20H, m).

Compound 16b

MS: m/z 904(MH+), m/z 872(M+ −OCH₃), m/z 858(M+ −OC₂H₅), m/z 846(M+ −tBu).

[α]_D −6.1±2.3° (23° C., c=0.147, CHCl₃).

IR: νmax (CHCl₃) 3080, 1730, 1592, 1472, 1112 cm⁻¹.

NMR: δ ppm (CDCl₃) 0.79 (3H), 1.00 (9H, s), 1.03 (9H, s), 1.24 (3H, t, J=7 Hz), 2.84 (3H, m), 3.45 (2H, m), 3.98 (2H, m), 4.15(2H, q, J=7 Hz), 5.27 (2H, m), 7.1–7.7 (20H, m).

Examples F-3–7

The conversion of the lactam into the thiolactam and S-alkylation are carried out according to Example F-2(1) and Example F-1-(2), respectively. The results are shown in Tables 12 and 13. The compound of which R₂ is trimethylsilylethynyl may sometimes be produced in Example F-5-(2).

TABLE 12

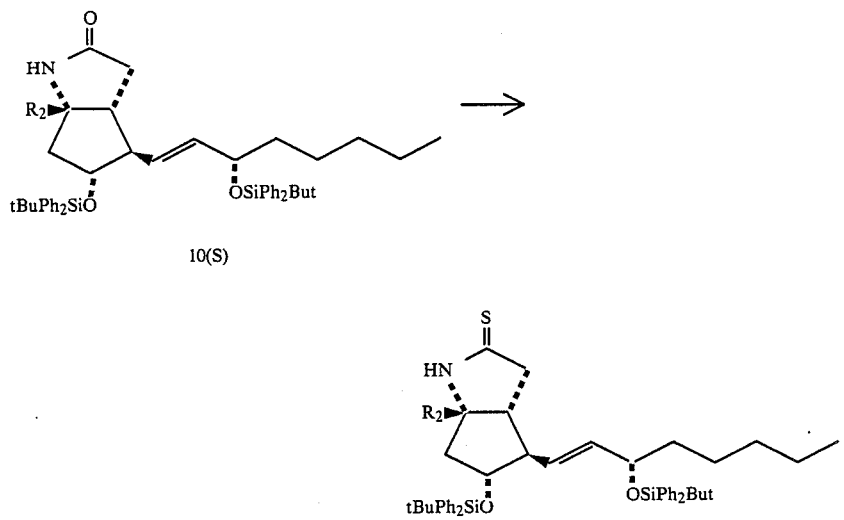

10(S)

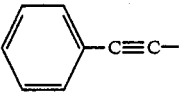

13(S)

| Ex. Number | Compd. Number | R₂ | Yd. | MS [m/z] | Specific Rotation [α]$_D$ |
|---|---|---|---|---|---|
| F-3-(1) | 13(S)d | CH₃CH₂— | 97% | 787 (M⁺)<br>730 (M⁺—tBu) | −10.7 ± 1.0°<br>(25° C., C = 0.513, CHCl₃) |
| F-4-(1) | 13(S)e | CH₃— | 96% | 773 (M⁺)<br>716 (M⁺—tBu) | −6.6 ± 0.9°<br>(22° C., C = 0.530, CHCl₃) |
| F-5-(1) | 13(S)f | (CH₃)₃Si—C≡C— | 98% | 798 (M⁺—tBu) | −7.5 ± 0.9°<br>(20° C., C = 0.505, CHCl₃) |
| F-6-(1) | 13(S)h | CH₃—C≡C— | 97% | 798 (MH⁺)<br>740 (M⁺—tBu) | −9.5 ± 1.0°<br>(23° C., C = 0.510, CHCl₃) |
| F-7-(1) | 13(S)i | Ph—C≡C— | 91% | 860 (MH⁺)<br>802 (M⁺—tBu) | −18.5 ± 1.2°<br>(24° C., C = 0.509, CHCl₃) |

| Ex. Number | IR νmax [cm⁻¹] | NMR δppm |
|---|---|---|
| F-3-(1) | (CHCl₃) 3405, 3080, 1592, 1493, 1113 | (CDCl₃) 0.70 (3H,t,J=7Hz), 0.80 (3H), 1.01 (9H,s), 1.04 (9H,s), 3.78 (1H,m), 4.11 (1H,m), 5.29 (2H,m), 7.1~7.75 (20H,m), 8.45 (1H,s) |
| F-4-(1) | (CHCl₃) 3400, 3072, 1590, 1494, 1112 | (CDCl₃) 0.80 (3H), 1.00 (9H,s), 1.03 (9H,s), 1.11 (3H,s), 3.7~4.2 (2H,m), 5.25 (2H,m), 7.2~7.75 (20H,m), 8.32 (1H,s) |
| F-5-(1) | (CHCl₃) 3404, 3072, 2164, 1590, 1474, 1111, 844 | (CDCl₃) 0.12 (9H,s), 0.80 (3H), 1.03 (18H,s), 4.04 (2H,m), 5.30 (2H,m), 7.2~7.75 (20H,m), 7.78 (1H,s) |
| F-6-(1) | (CHCl₃) 3404, 3072, 1590, 1482, 1473, 1112 | (CDCl₃) 0.80 (3H), 1.01 (9H,s), 1.03 (9H,s), 1.71 (3H,s), 4.02 (2H,m), 5.25 (2H,m), 7.2~7.7 (20H,m), 7.86 (1H,s) |
| F-7-(1) | (CHCl₃) 3404, 3072, 1591, 1488, 1474, 1113 | (CDCl₃) 0.79 (3H), 1.03 (18H,s), 3.9~4.2 (2H,m), 5.30 (2H,m), 7.15~7.75 (25H,m), 8.04 (1H,s) |

TABLE 13

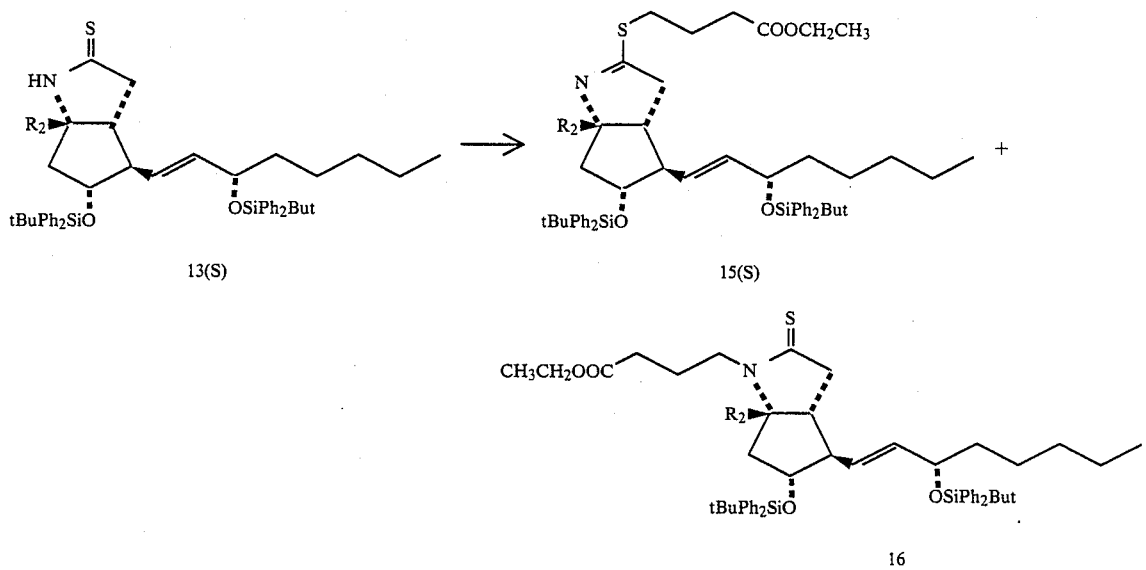

| Ex. Number | Compd. Number | R₂ | Yd. (%) | MS [m/z] | Specific Rotation $[\alpha]_D$ | IR $\nu$max [cm$^{-1}$] | NMR $\delta$ppm |
|---|---|---|---|---|---|---|---|
| F-3-(2) | 15(S)d | CH₃CH₂— | 94 | 901 (M⁺) 844 (M⁺—tBu) | +15.1 ± 1.0° (25° C., c = 0.571, CHCl₃) | (CHCl₃) 3080, 3005, 1730, 1590, 1112 | (CDCl₃) 0.56 (3H,t,J=7Hz), 0.81 (3H), 1.00 (9H,s), 1.03 (9H,s), 1.23 (3H,t,J=7Hz), 3.06 (2H,m), 3.67 (1H,m), 3.95~4.2 (1H,m), 4.11 (2H,q,J=7Hz), 5.30 (2H,m), 7.15~7.75 (20H,m) |
| | 16d | | 2 | 901 (M⁺) 844 (M⁺—tBu) | | (CHCl₃) 1725, 1590, 1485, 1110 | (CDCl₃) 0.56 (3H,t,J=7Hz), 0.80 (3H), 1.00 (9H,s), 1.04 (9H,s), 1.24 (3H,t,J=7Hz), 3.75 (1H,m), 3.95~4.25 (1H,m), 4.11 (2H,q,J=7Hz), 5.32 (2H,m), 7.15~7.8 (20H,m) |
| F-4-(2) | 15(S)e | CH₃— | 91 | 888 (MH⁺) 842 (M⁺—OCH₂CH₃) 830 (M⁺—tBu) | +18.3 ± 1.1° (20° C., c = 0.540, CHCl₃) | (CHCl₃) 3072, 1729, 1589, 1111 | (CDCl₃) 0.80 (3H), 1.00 (9H,s), 1.03 (9H,s), 1.23 (3H,t,J=7Hz), 3.08 (2H,m), 3.77 (1H,m), 3.95~4.2 (1H,m), 4.13 (2H,q,J=7Hz), 5.32 (2H,m), 7.2~7.8 (20H,m) |
| | 16e | | 2 | 888 (MH⁺) 842 (M⁺—OCH₂CH₃) 830 (M⁺—tBu) | | (CHCl₃) 1725, 1585, 1480, 1110 | (CDCl₃) 0.80 (3H), 1.00 (9H,s), 1.03 (9H,s), 1.12 (3H,s), 1.25 (3H,t,J=7Hz), 3.7~4.2 (2H,m), 4.15 (2H,q,J=7Hz), 5.31 (2H,m), 7.2~7.7 (20H,m) |
| F-5-(2) | 15(S)g | HC≡C— | 87.5 | 898 (MH⁺) 852 (M⁺—OCH₂CH₃) 840 (M⁺—tBu) | +6.1 ± 0.8° (20° C., c = 0.589, CHCl₃) | (CHCl₃) 3312, 3072, 1730, 1589, 1580, 1112 | (CDCl₃) 0.81 (3H), 1.00 (9H,s), 1.03 (9H,s), 1.23 (3H,t,J=7Hz), 2.29 (1H,s), 3.11 (2H,t,J=7Hz), 3.97 (2H,m), 4.11 (2H,q,J=7Hz), 5.28 (2H,m), 7.15~7.75 (20H,m) |
| | 16g | | 4.5 | 898 (MH⁺) 840 (M⁺—tBu) | | (CHCl₃) 3308, 3072, 1729, 1590, 1472, 1112 | (CDCl₃) 0.80 (3H), 1.00 (9H,s), 1.02 (9H,s), 1.24 (3H,t,J=7Hz), 2.44 (1H,s), 4.05 (2H,m), 4.14 (2H,q,J=7Hz), 5.27 (2H,m), 7.2~7.75 (20H,m) |
| | 15(S)f | (CH₃)₃Si—C≡C— | | | | (CHCl₃) 3070, 2160, 1725, 1590, 1580, 1110, 855, 842 | (CDCl₃) 0.08 (9H,s), 0.80 (3H), 1.00 (9H,s), 1.03 (9H,s), 1.23 (3H, t,J=7Hz), 3.13 (2H,m), 3.75~4.2 (2H,m), 4.13 (2H,q,J=7Hz), 5.32 (2H,m), 7.15~7.8 (20H,m) |
| F-6-(2) | 15(S)h | CH₃—C≡C— | 93 | 912 (MH⁺) 866 (M⁺—OCH₂CH₃) 854 (M⁺—tBu) | +2.7 ± 0.9° (23° C., c = 0.490, CHCl₃) | (CHCl₃) 3072, 1729, 1590, 1582, 1112 | (CDCl₃) 0.80 (3H), 0.98 (9H,s), 1.02 (9H,s), 1.23 (3H,t,J=7Hz), 1.70 (3H,s), 3.13 (2H,t,J=7Hz), 3.95 (2H,m), 4.13 (2H,q,J=7Hz), 5.32 (2H,m), 7.2~7.8 (20H,m) |
| | 16h | | 5.5 | 912 (MH⁺) 866 (M⁺—OCH₂CH₃) 854 (M⁺—tBu) | | (CHCl₃) 3072, 1729, 1590, 1472, 1112 | (CDCl₃) 0.80 (3H), 1.00 (9H,s), 1.03 (9H,s), 1.24 (3H,t,J=7Hz), 1.72 (3H,s), 3.8~4.2 (2H,m), 4.14 (2H,q,J=7Hz), 5.27 (2H,m), 7.2~7.8 (20H,m) |

TABLE 13-continued

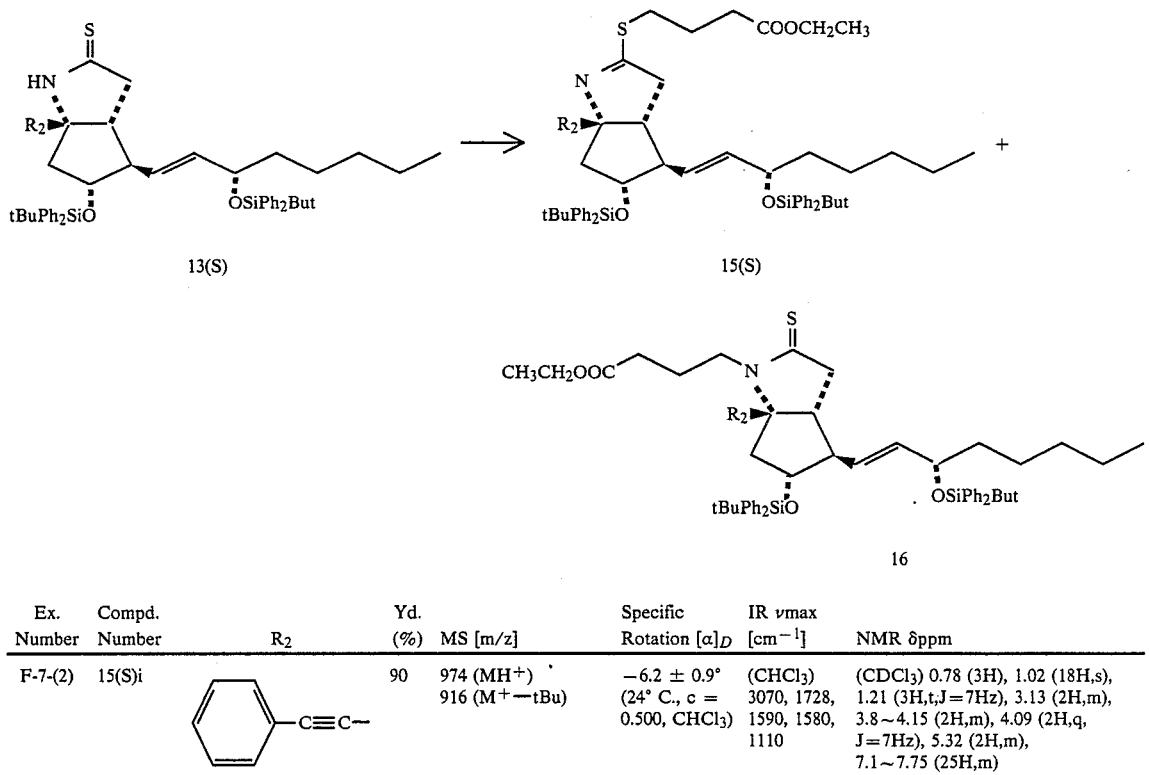

| Ex. Number | Compd. Number | R₂ | Yd. (%) | MS [m/z] | Specific Rotation [α]$_D$ | IR νmax [cm$^{-1}$] | NMR δppm |
|---|---|---|---|---|---|---|---|
| F-7-(2) | 15(S)i | —C≡C—C₆H₅ | 90 | 974 (MH⁺) 916 (M⁺—tBu) | −6.2 ± 0.9° (24° C., c = 0.500, CHCl₃) | (CHCl₃) 3070, 1728, 1590, 1580, 1110 | (CDCl₃) 0.78 (3H), 1.02 (18H,s), 1.21 (3H,t,J=7Hz), 3.13 (2H,m), 3.8∼4.15 (2H,m), 4.09 (2H,q, J=7Hz), 5.32 (2H,m), 7.1∼7.75 (25H,m) |

Example F-8

Preparation of ethyl 4-[7-hydroxy-6-[(3S)-3-hydroxy-1-octenyl]-1-phenylthio-2-azabicyclo[3.3.0]oct-2-en-3-yl]thiobutanoate 17(S)a

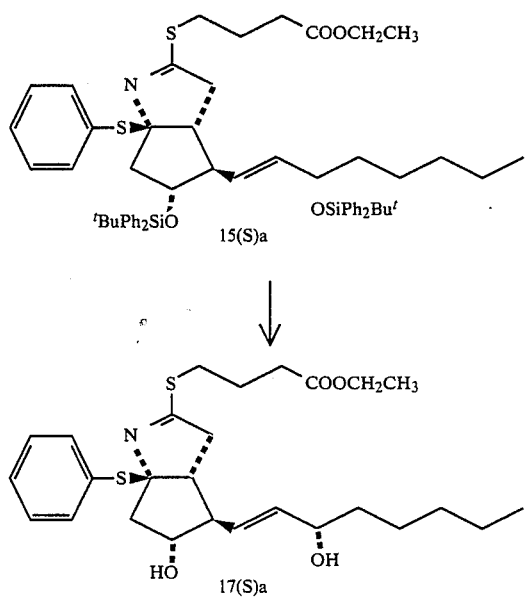

In an atmosphere of nitrogen, 1.1 ml (1.1 mmol) of 1M tetrahydrofuran solution of tetra-n-butylammonium fluoride is added to a solution of 264 mg (0.269 mmol) of the silyl ether 15(S)a (Example F-1-(2)) in 8 mol of dry tetrahydrofuran and the mixture is stirred at room temperature for 21 hours. The reaction mixture is poured into a saturated aqueous solution of sodium chloride and extracted 3 times with ethyl acetate, and the extract is washed with a saturated aqueous solution of sodium chloride, dried over anhydrous magnesium sulfate, and evaporated to give 270 mg of a residue, which is purified by thin layer chromatography (Merck; precoated plate; size 20×20, thickness 0.5 mm; 13 plates; developed with benzene:ethyl acetate=1:4) to give 118 mg of the compound 17(S) a as an oil (87% yield).

MS: m/z 506 (MH⁺), m/z 460 (M⁺—OC₂H₅), m/z 396 (M⁺—SPh).

[α]$_D$ −24.7±0.6° (24° C., c=1.016, CHCl₃).

IR: νmax (CHCl₃) 3605, 3405, 1728, 1570, 1074, 971 cm⁻¹.

NMR: δ ppm (CDCl₃) 0.85 (3H), 1.25 (H, t, J=7 Hz), 3.13 (2H, t, J=7 Hz), 3.98 (2H, m), 4.13 (2H, q, J=7 Hz), 5.45 (2H, m), 7.1-7.6 (5H, m).

Examples F-9–14

Removal of silyl groups, of which results are shown in Table 14, is carried out in the same manner as in Example F-8.

In addition, the compound 15(S)f may be converted into the compound 17(S)g in the same manner as in the desilylation reaction as mentioned above.

TABLE 14

| Ex. Number | Compd. Number | R₂ | Yd. (%) | MS [m/z] | Specific Rotation $[\alpha]_D$ | IR ν max [cm⁻¹] | NMR δ ppm |
|---|---|---|---|---|---|---|---|
| F-9 | 17(S)b | CH₃O— | 95 | 427 (M⁺)<br>396 (M⁺—OCH₃)<br>382 (M⁺—OCH₂CH₃) | +99.0 ± 7.4°<br>(23.5° C., c = 0.188, CHCl₃) | (CHCl₃) 3610, 3415, 1730, 1592, 1070, 971 | (CDCl₃) 0.87(3H), 1.24(3H, t, J=7Hz), 3.12(3H, s), 3.12(2H, t, J=7Hz), 3.97(2H, m), 4.11(2H, q, J=7Hz), 5.51(2H, m) |
| F-10 | 17(S)d | CH₃CH₂— | 88 | 425 (M⁺)<br>380 (M⁺—OCH₂CH₃) | +73.6 ± 2.0°<br>(24.5° C., c = 0.564, CHCl₃) | (CHCl₃) 3605, 3405, 1727, 1585, 1076, 970 | (CDCl₃) 0.77 (3H, t, J=7Hz), 0.87(3H), 1.24(3H, t, J=7Hz), 3.08(2H, t, J=7Hz), 3.70(1H, m), 3.92~4.2 (1H, m), 4.12(2H, q, J=7Hz), 5.48(2H, m) |
| F-11 | 17(S)e | CH₃— | 77 | 411 (M⁺)<br>366 (M⁺—OCH₂CH₃) | +78.8 ± 2.2°<br>(23.5° C., c = 0.546, CHCl₃ | (CHCl₃) 3604, 3416, 1729, 1587, 1078, 972 | (CDCl₃) 0.88(3H), 1.21(3H, s), 1.25(3H, t, J=7Hz), 3.10(2H, m), 3.6~4.2(2H, m), 4.14(2H, q, J=7Hz), 5.50(2H, m) |
| F-12 | 17(S)g | HC≡C— | 83 | 421 (M⁺)<br>376 (M⁺—OCH₂CH₃) | +45.4 ± 1.2°<br>(22° C., c = 0.715, CHCl₃) | (CHCl₃) 3604, 3408, 3312, 1729, 1579, 1084, 1049, 971 | (CDCl₃) 0.88(3H), 1.25(3H, t, J=7Hz), 2.45(1H, s), 3.13(2H, m), 3.8~4.25(2H, m), 4.14(2H, q, J=7Hz), 5.53(2H, m) |
| F-13 | 17(S)h | CH₃—C≡C— | 81 | 435 (M⁺)<br>390 (M⁺—OCH₂CH₃) | +23.8 ± 1.3°<br>(23° C., c = 0.508, CHCl₃) | (CHCl₃) 3604, 3404, 1728, 1580, 1083, 971 | (CDCl₃) 0.87(3H), 1.25(3H, t, J=7Hz), 1.79(3H, s), 3.10(2H, m), 3.75~4.2(2H, m), 4.14(2H, q, J=7Hz), 5.52(2H, m) |
| F-14 | 17(S)i | Ph—C≡C— | 72.5 | 497 (M⁺)<br>452 (M⁺—OCH₂CH₃) | −17.5 ± 1.1°<br>(23.5° C., c = 0.505, CHCl₃) | (CHCl₃) 3600, 3410, 1726, 1587, 1081, 1044, 971 | (CDCl₃) 0.87(3H), 1.23(3H, t, J=7Hz), 3.13(2H, m), 3.8~4.2 (2H, m), 4.10(2H, q, J=7Hz), 5.55(2H, m), 7.15~7.5(5H, m) |

Example F-15

Preparation of methyl 4-[1-ethynyl-7-hydroxy-6-[(3S)-3-hydroxy-1-octenyl]-2-azabicyclo[3.3.0]oct-2-en-3-yl]thiobutanoate 18(S)g

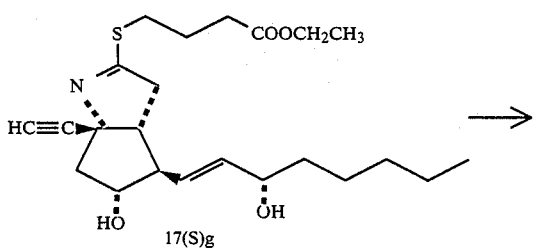

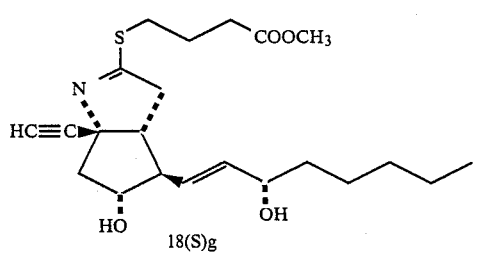

In an atmosphere of nitrogen, 0.3 ml (0.3 mmol) of 1N methanol solution of sodium methoxide is added to a solution of 150 mg (0.356 mmol) of the ethyl ester 17(S)g (Example F-12) in 3 ml of dry methanol and the mixture is stirred at room temperature for 1 hour and 40 minutes. The reaction mixture is poured into a saturated aqueous solution of ammonium chloride and then methanol is evaporated. The residue is poured into water and extracted 3 times with ethyl acetate. The extract is washed with water, dried over anhydrous magnesium sulfate and evaporated to give 150 mg of a residue. The residue is purified by column chromatography (Lobar column, size A (2 columns); eluted with benzene:acetone=4:1) to give 137 mg of the compound 18(S)g as an oil (94.5% yield).

MS: m/z 407 (M+), m/z 376 (M+ —OCH$_3$).

[α]$_D$+47.8±1.7° (23.5° C., c=0.513, CHCl$_3$).

IR: ν max (CHCl$_3$) 3604, 3424, 3312, 1733, 1579, 1083, 1052, 971 cm$^{-1}$.

NMR: δppm (CDCl$_3$) 0.87 (3H), 2.46 (1H, s), 3.13 (2H, m), 3.67 (3H, s), 3.75–4.2 (2H, m), 5.52 (2H, m).

Example F-16

(1) Preparation of Sodium 4-[1-ethynyl-7-hydroxy-6-[(3S)-3-hydroxy-1-octenyl]-2-azabicyclo[3.3.0]oct-2-en-3-yl]thiobutanoate 19(S)g

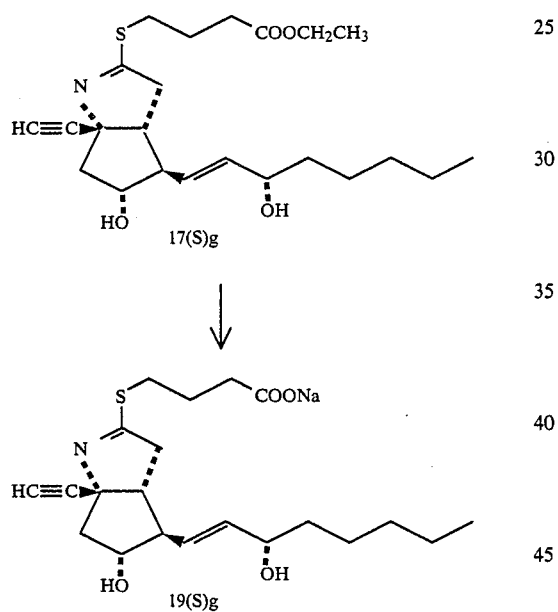

In an atmosphere of nitrogen, 0.70 ml (0.070 mmol) of 0.1N aqueous solution of sodium hydroxide and 0.3 ml of water are added to a solution of 30.0 mg (0.0719 mmol) of the ethyl ester 17(S)g (Example F-12) and the mixture is allowed to stand at room temperature for 2 days. The reaction mixture is evaporated under reduced pressure and the residue is washed well with diethyl ether. Insoluble material is dissolved in methanol and evaporated again, and the residue is washed well with diethyl ether. This operation is repeated again, and the residue is dried to give 25 mg of the compound 19(S)g as a hygroscopic foamy material.

IR: ν max (KBr) 3380, 3290, 1575, 1408, 1086 cm$^{-1}$.

NMR: δ ppm (D$_2$O-TMS external standard) 1.35 (3H), 4.53 (2H, m), 6.03 (2H, m).

(2) Preparation of 4-[1-ethynyl-7-hydroxy-6-[(3S)-3-hydroxy-1-octenyl]-2-azabicyclo[3.3.0]oct-2-en-3-yl]thiobutanoic acid 20(S)g

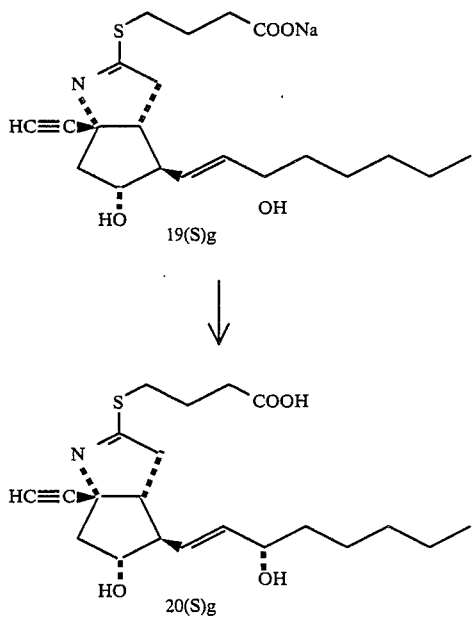

In ethyl acetate is suspended the sodium salt of carboxylic acid 19(S)g (Example F-16-(1)) prepared from 29.3 mg (0.0695 mmol) of the ethyl ester 17(S)g (Example F-12) and then a buffer of about pH 4.5 [which is prepared by mixing an aqueous solution of disodium citrate (prepared from 21 g of citric acid (C$_6$H$_8$O$_7$.H$_2$O) and 200 ml of aqueous solution of sodium hydroxide) and 1/10N hydrochloric acid in the ratio 5.65:4.35] and an aqueous solution of sodium chloride are added to the suspension. After the mixture is shaken, the ethyl acetate layer is separated. The aqueous layer is extracted with ethyl acetate again. The combined organic layer is washed with a saturated aqueous solution of sodium chloride, dried over anhydrous magnesium sulfate, and evaporated to give 24 mg of the compound 20(S)g as an oil.

IR: ν max (CHCl$_3$) 3400 (br.), 3300, 1708, 1578, 1080 cm$^{-1}$.

NMR: δ ppm (CDCl$_3$+D$_2$O) 0.87 (3H), 2.50 (1H, s), 4.01 (2H, m), 5.52 (2H, m).

Example F-17

(1) Preparation of 1-(4-trimethylsilyl-1,3-butadiynyl)-2-aza-3-thioxo-6-[(3S)-3-tert-butyldiphenylsilyloxyoct-1-enyl]-7-tert-butyldiphenylsilyloxybicyclo[3.3.0]octane 13(S)j

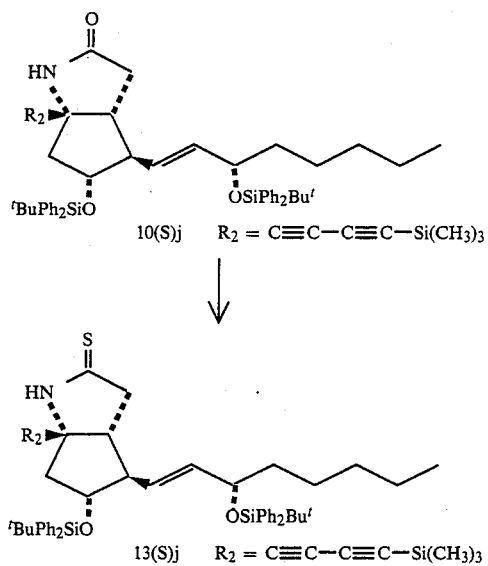

The 4-trimethylsilyl-1,3-butadiynyl-lactam 10(S)j (454 mg; Example I-22) is allowed to react in the same manner as in Example F-2-(1) to give 445 mg of the compound 13(S)j as a foamy material (96% yield).

MS: m/z 822(M+ −tBu).

[α]$_D$ −34.9±1.5° (23.5° C., c=0.504, CHCl$_3$).

IR: ν max (CHCl$_3$) 3400, 3072, 2200, 2104, 1590, 1472, 1112, 843 cm$^{-1}$.

NMR: δ ppm (CDCl$_3$) 0.16 (9H, s), 0.81 (3H), 1.00 (9H, s), 1.02 (9H, s), 4.03 (2H, m), 5.25 (2H, m), 7.2–7.75 (20H, m), 7.96 (1H, s).

(2) Preparation of ethyl 4-[1-(1,3-butadiynyl)-7-tert-butyldiphenylsilyloxy-6-[(3S)-3-tert-butyldiphenylsilyloxy-1-octenyl]-2-azabicyclo[3.3.0]oct-2-en-3-yl]thiobutanoate 15(S)k

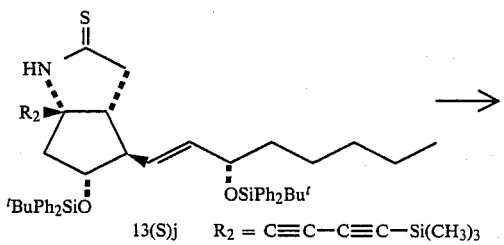

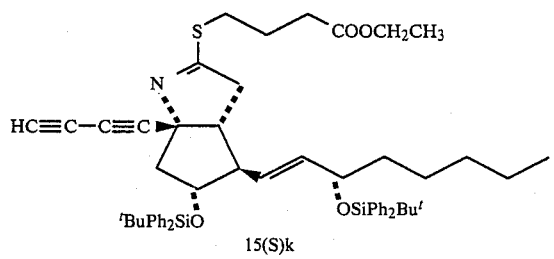

The alkylation of 402 mg of the 4-trimethylsilyl-1,3-butadiynyl-thiolactam 13(S)j (Example F-17-(1)) is carried out in the same manner as in Example F-1-(2) to afford 403 mg of the compound 15(S)k as an oil (95.5% yield).

MS: m/z 864 (M+ −tBu).

[α]$_D$ −14.1±1.1° (23° C., c=0.514, CHCl$_3$). IR: ν max (CHCl$_3$) 3312, 3072, 2228, 1730, 1590, 1577, 1112 cm$^{-1}$.

NMR: δ ppm (CDCl$_3$) 0.82 (3H), 1.00 (9H, s), 1.03 (9H, s), 1.25 (3H, t, J=7 Hz), 2.13 (1H, s), 3.13 (2H, t, J=7 Hz), 3.75–4.15 (2H, m), 4.14 (2H, q, J=7 Hz), 5.37 (2H, m), 7.15–7.75 (20H, m).

Example F-18

Preparation of ethyl 4-[1-(1,3-butadiynyl)-7-hydroxy-6-[(3S)-3-hydroxy-1-octenyl]-2-azabicycl[3.3.0]oct-2-en-3-yl]thiobutanoate 17(S)k

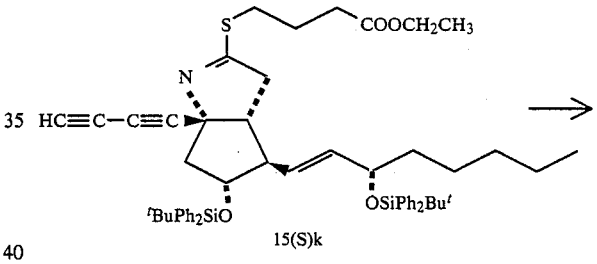

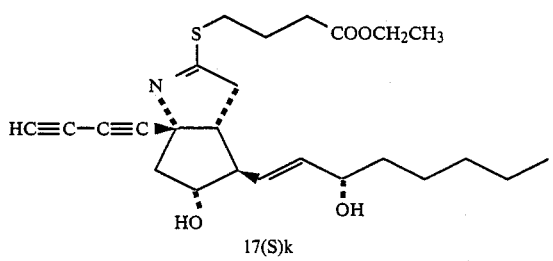

Removal of silyl groups carried out in the same manner as in Example F-8 using 346 mg the silyl ether 15(S)k (Example F-17-(2)) affords 136 mg of the compound 17(S)k as an oil (81.5% yield).

MS: m/z 445 (M+), m/z 400 (M+ −OC$_2$H$_5$).

[α]$_D$ −19.6±1.2° (23° C., c=0.509, CHCl$_3$).

IR: ν max (CHCl$_3$) 3604, 3412, 3312, 2228, 1727, 1578, 1085, 971 cm$^{-1}$.

NMR: δ ppm (CDCl$_3$) 0.87 (3H), 1.24 (3H, t, J=7 Hz), 2.18 (1H, s), 3.10 (2H, m), 3.75–4.15 (2H, m), 4.11 (2H, q, J=7 Hz), 5.49 (2H, m).

Example F-19

Preparation of ethyl 4-[1-cyano-7-tert-butyldiphenylsilyloxy-6-[(3S)-3-tert-butyldiphenylsilyloxy-1-octenyl]-2-azabicyclo[3.3.-0]oct-2-en-3-yl]thiobutanoate 15(S)k

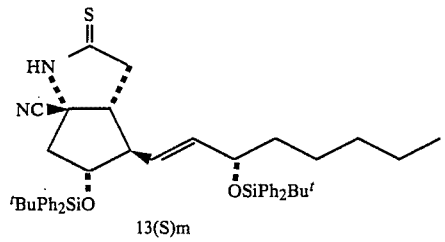

13(S)m

↓

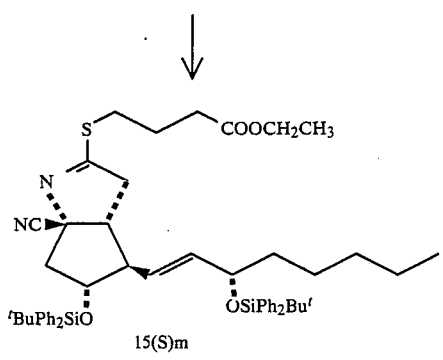

15(S)m

In an atmosphere of nitrogen, a solution of 590 mg (0.752 mmol) of the cyano-thiolactam 13(S)m (Example I-26) in 15 ml of dry N,N-dimethylformamide is cooled in an ice water bath, then 37 mg (0.91 mmol) of 59% sodium hydride is added thereto, and the mixture is stirred for 2 hours and 50 minutes. Subsequently, 191 mg (0.978 mmol) of 4-bromobutyric acid ethyl ester is added and the mixture is stirred at the same temperature for 40 minutes. The reaction mixture is poured into ice water and extracted with ethyl acetate twice. The extract is washed with water, dried over anhydrous magnesium sulfate, and evaporated to give 737 mg of residue, which is purified by column chromatography (Lobar column, size B, 2 columns; eluted with benzene:ethyl acetate=100:1) to give 640 mg of the compound 15(S)m as an oil (94.5% yield).

MS: m/z 899 (MH+), m/z 853 (M+ —OCH$_2$CH$_3$), m/z 841 (M+ —$^t$Bu).

$[\alpha]_D^{21}$ +10.2±1.0° (c=0.506, CHCl$_3$).

IR: $\nu_{max}^{CHCl_3}$ 2236, 1730, 1591, 1575, 1113 cm$^{-1}$.

NMR: $\delta_{ppm}^{CDCl_3}$ 0.81 (3H), 1.00 (9H, s), 1.02 (9H, s), 1.24 (3H, t, J=7 Hz), 3.10 (2H, m), 3.75–4.15 (2H, m), 4.12 (2H, q, J=7 Hz), 5.20 (2H, m), 7.15–7.75 (20H, m).

Example F-20

Preparation of ethyl 4-[1-ethenyl-7-tert-butyldiphenylsilyloxy-6-[(3S)-3-tert-butyldiphenylsilyloxy-1-octenyl]-2-azabicyclo[3.3.-0]oct-2-en-3-yl]thiobutanoate 15(S)l

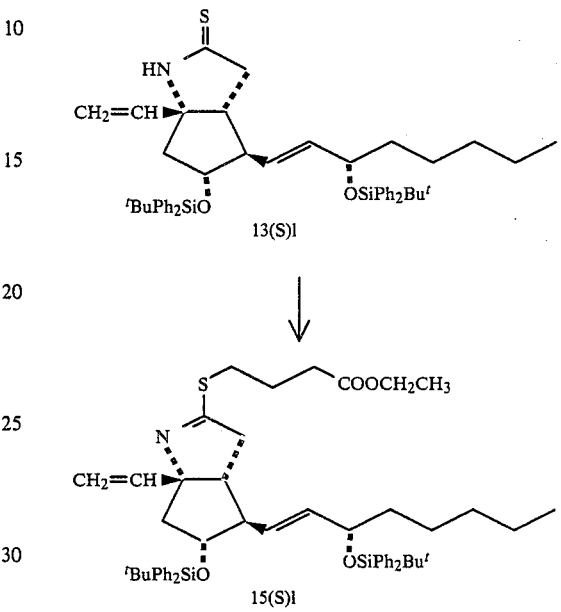

In the same manner as in Example F-19, 383 mg of the ethenyl-thiolactam 13(S)l (Example 1-7) is alkylated to give 402 mg of the compound 15(S)l as an oil (91.5% yield).

MS: m/z 899 (M+), m/z 854 (M+ —OCH$_2$CH$_3$), m/z 842 (M+ —$^t$Bu).

$[\alpha]_D^{23}$ +5.0±0.9° (c=0.504, CHCl$_3$).

IR: $\nu_{max}^{CHCl_3}$ 1729, 1638, 1588, 1112 cm$^{-1}$.

NMR: $\delta_{ppm}^{CDCl_3}$ 0.81 (3H), 1.00 (9H, s), 1.04 (9H, s), 1.24 (3H, t, J=7 Hz), 3.12 (2H, m), 3.79 (1H, m), 3.95–4.2 (1H, m), 4.11 (2H, q, J=7 Hz), 4.6–4.85 (2H, m), 5.30 (2H, m), 5.46–5.8 (1H, m), 7.2–7.75 (20H, m).

Example F-21

Preparation of ethyl 4-[1-cyano-7-hydroxy-6-[(3S)-3-hydroxy-1-octenyl]-2-azabicyclo[3.3.0]oct-2-en-3-yl]thiobutanoate 17(S)m

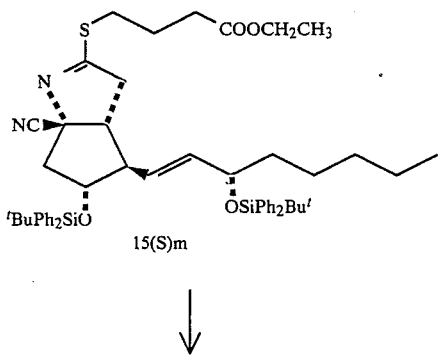

15(S)m

↓

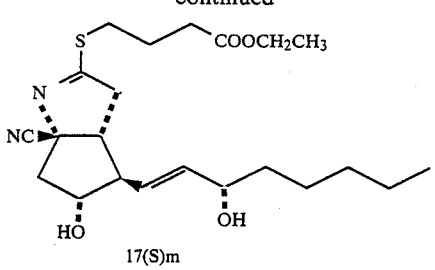

17(S)m

To a solution of 535 mg (0.596 mmol) of the silyl ether 15(S)m (Example F-19) in 15 ml of dry tetrahydrofuran is added 3.6 ml (3.6 mmol) of 1M tetrahydrofuran solution of tetra-n-butylammonium fluoride in an atmosphere of nitrogen and the mixture is stirred at room temperature for 5 hours. A saturated aqueous solution of ammonium chloride is added to the reaction mixture, which is then extracted with ethyl acetate twice. The extract is washed with a saturated aqueous solution of sodium chloride, dried over anhydrous magnesium sulfate, and evaporated to give 593 mg of residue, which is purified by column chromatography (30 g of alumina; eluted with benzene:ethyl acetate=1:1-ethyl acetate:methanol=1:1) to give 230 mg of an oily material. Further purification by column chromatography (Lober column, size B; eluted with benzene:acetone=3:1) affords 209 mg of the compound 17(S)m as an oil (83%) yield).

MS: m/z 422 (M+) m/z 377 (M+−OCH$_2$CH$_3$).
$[\alpha]_D^{21}$+65.4±2.1° (c=0.510, CHCl$_3$).
IR: $\nu_{max}^{CHCl_3}$ 3608, 3420, 2240, 1731, 1575, 1089, 1075, 972 cm$^{-1}$.
NMR: $\delta_{ppm}^{CDCl_3}$ 0.88 (3H), 1.26 (3H, t, J=7 Hz), 3.13 (2H, m), 4.0 (2H, m), 4.14 (2H, q, J=7 Hz), 5.52 (2H, m).

Example F-22

Preparation of ethyl 4-[1-ethenyl-7-hydroxy-6-[(3S)-3-hydroxy-1-octenyl]-2-azabicyclo[3.3.0]oct-2-en-3-yl]thiobutanoate 17(S)l

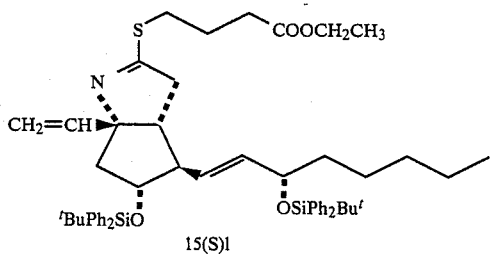

15(S)l

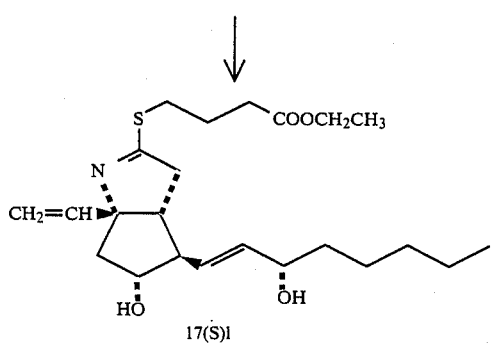

17(S)l

Removal of silyl groups carried out in the same manner as in Example F-21 affords 145 mg of the oily compound 17(S)l (85.5% yield) from 360 mg of the silyl ether 15(S)l (Example F-20).

MS: m/z 423 (M+) m/z 378 (M+−OCH$_2$CH$_3$).
$[\alpha]_D^{21}$+48.5±1.7° (c=0.513, CHCl$_3$).
IR: $\nu_{max}^{CHCl_3}$ 3604, 3424, 1729, 1639, 1585, 1079, 971 cm$^{-1}$.
NMR: $\delta_{ppm}^{CDCl_3}$ 0.88 (3H), 1.24 (3H, t, J=7 Hz), 3.12 (2H, t, J=7 Hz), 3.7-4.2 (2H, m), 4.11 (2H, q, J=7 Hz), 4.8-5.1 (2H, m), 5.50 (2H, m), 5.8-6.1 (1H, m).

Example F-23

Preparation of ethyl 4-[7-tert-butyldiphenylsilyloxy-1-ethynyl-6-[(3S)-3-tert-butyldiphenylsilyloxy-1-octenyl]-2-azabicyclo[3.3.0]oct-2-en-3-yl]thiobutanoate 15(S)g

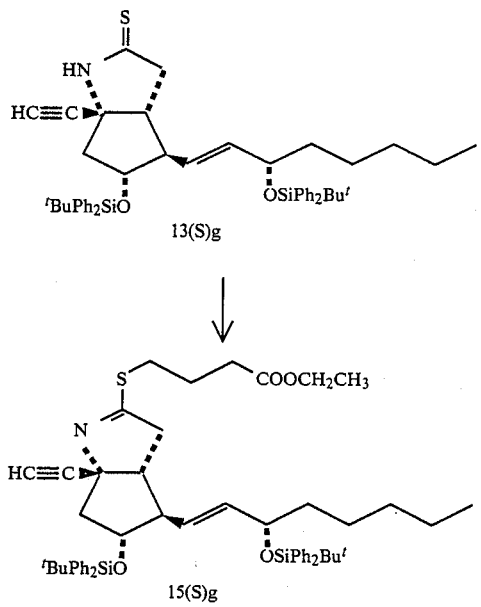

A solution of 126 mg (0.161 mmol) of the thiolactam 13(S)g (Example I-114) in 5 ml of dry N,N-dimethylformamide is cooled in an ice water bath, then 8 mg (0.203 mmol) of 61% sodium hydride is added in an atmosphere of nitrogen thereto, and the mixture is stirred for 2 hours. Then 44 mg (0.224 mmol) of ethyl 4-bromobutyrate is added and the mixture is stirred at the same temperature for 35 minutes. Ice water is added to the reaction mixture, which is then extracted with ethyl acetate twice. The extract is washed with water, dried over anhydrous magnesium sulfate, and evaporated to give 167 mg of residue, which is purified by column chromatography (Lober column, size B; eluted with benzene:ethyl acetate=80:1) to give 134 mg of the compound 15(S)g as an oil (93% yield).

MS: m/z 898 (MH+), m/z 852 (M+−OCH$_2$CH$_3$), m/z 840 (M+−tBu).
$[\alpha]_D^{20}$+6.1±0.8° (c=0.589, CHCl$_3$).
IR: $\nu_{max}^{CHCl_3}$ 3312, 1730, 1589, 1580, 1112 cm$^{-1}$.
NMR: $\delta_{ppm}^{CDCl_3}$ 0.81 (3H), 1.00 (9H, s), 1.03 (9H, s), 1.23 (3H, t, J=7 Hz), 2.29 (1H, s), 3.11 (2H, t, J=7 Hz), 3.97 (2H, m), 4.11 (2H, q, J=7 Hz), 5.28 (2H, m), 7.15-7.75 (20H, m).

Example F-24-F-44 and F-69-F-72

Alkylation is carried out in the same manner as in Example F-23 and results are shown in Tables 15 and 16.

TABLE 15

| Ex. No. | Compound No. | R₂ | R₃, R₄ | R₅ | Yd. (%) | MS [m/z] | Specific Rotation [α]_D | IR ν max [cm⁻¹] | NMR δ ppm |
|---|---|---|---|---|---|---|---|---|---|
| F-25 | 15(S)g-b | CH≡C— | ᵗBuPh₂Si— | CH₃-CH(CH₃)-(CH₂)₃- | 94 | 911 (M⁺), 866 (M⁺—OEt), 854 (M⁺—ᵗBu) | | (CHCl₃) 3312, 1730, 1591, 1580, 1112 | (CDCl₃) 0.8(6H, m), 1.00(9H, s), 1.03(9H, s), 1.23(3H, t, J=7Hz), 2.30 (1H, s), 3.11(2H, t, J=7Hz), 3.90(2H, m), 4.11(2H, q, J=7Hz), 5.23(2H, m), 7.15~7.7(20H, m) |
| F-27 | 15(R)g-c | CH≡C— | ᵗBuMe₂Si— | H₃C-C(CH₃)₂-(CH₂)₃-CH₃ | 90 | 677 (M⁺), 632 (M⁺—OEt), 620 (M⁺—ᵗBu) | +26.2 ± 1.5° (24° C., c = 0.451, CHCl₃) | (CHCl₃) 3312, 1731, 1581, 1473, 1257, 1114, 1102, 1070, 856, 837 | (CDCl₃) −0.02(3H, s), 0.02(3H, s), 0.05(6H, s), 0.77(3H, s), 0.80(3H, s), 0.85(9H, s), 0.88(9H, s), 1.24 (3H, t, J=7Hz), 2.43(1H, s), 3.13(2H, t, J=7Hz), 3.74(1H, m), 4.01(1H, m), 4.14(2H, q, J=7Hz), 5.50(2H, m) |
| F-29 | 15(S)g-d | CH≡C— | ᵗBuPh₂Si— | CH₃-C≡C-CH(CH₃)- | 84.5 | 907 (M⁺), 862 (M⁺—OEt), 850 (M⁺—ᵗBu) | | (CHCl₃) 3312, 1730, 1591, 1580, 1112 | (CDCl₃) 0.84(3H, m), 0.97(9H, s), 1.00(9H, s), 1.22(3H, t, J=7Hz), 1.72 (3H), 2.30(1H, s), 3.11(2H, t, J=7Hz), 3.80(1H, m), 4.08(1H, m), 4.12 (2H, q, J=7Hz), 5.16(2H, m), 7.15~7.75 (20H, m) |
| F-31 | 15(S)g-e | CH≡C— | ᵗBuPh₂Si— | cyclohexyl-H | 93.5 | 910 (MH⁺), 864 (M⁺—OEt), 852 (M⁺—ᵗBu) | +3.4 ± 0.9° (22° C., c = 0.477, CHCl₃) | (CHCl₃) 3312, 1730, 1591, 1580, 1112 | (CDCl₃) 1.00(9H, s), 1.02(9H, s), 1.23(3H, t, J=7Hz), 2.30(1H, s), 3.11 (2H, t, J=7Hz), 3.83(2H, m), 4.11(2H, q, J=7Hz), 5.17(2H, m), 7.15~7.75 (20H, m) |
| F-33 | 15(S)g-g | CH≡C— | ᵗBuPh₂Si— | furyl-propyl | 92 | 921 (M⁺), 876 (M⁺—OEt), 864 (M⁺—ᵗBu) | +14.4 ± 1.1° (24° C., c = 0.478, CHCl₃) | (CHCl₃) 3312, 1730, 1589, 1581, 1113 | (CDCl₃) 0.99(9H, s), 1.03(9H, s), 1.24(3H, t, J=7Hz), 2.31(1H, s), 3.14 (2H, t, J=7Hz), 3.89(1H, m), 4.14(2H, q, J=7Hz), 4.15(1H, m), 5.28(2H, m), 5.81(1H), 6.23(1H), 7.2~7.75 (21H, m) |

TABLE 15-continued

| Ex. No. | Compound No. | R$_2$ | R$_3$, R$_4$ | R$_5$ | Yd. (%) | MS [m/z] | Specific Rotation [α]$_D$ | IR ν max [cm$^{-1}$] | NMR δ ppm |
|---|---|---|---|---|---|---|---|---|---|
| F-35 | 15(S)h-b | CH$_3$—C≡C— | $^t$BuPh$_2$Si— | CH$_3$ (isohexyl) | 77 | | | (CHCl$_3$) 1731, 1591, 1113 | (CDCl$_3$) 0.79(6H, m), 1.00(9H, s), 1.03(9H, s), 1.23(3H, t, J=7Hz), 1.70 (3H, s), 3.13(2H, t, J=7Hz), 3.95(2H, m), 4.13(2H, q, J=7Hz), 5.24(2H, m), 7.15~7.75(20H, m) |
| F-37 | 15(S)h-e | CH$_3$—C≡C— | $^t$BuPh$_2$Si— | cyclohexyl | 94 | 924 (MH$^+$) 866 (M$^+$—$^t$Bu) | −1.1 ± 0.7° (23° C., c = 0.574, CHCl$_3$) | (CHCl$_3$) 1730, 1591, 1113 | (CDCl$_3$) 0.98(9H, s), 1.01(9H, s), 1.23(3H, t, J=7Hz), 1.70(3H, s), 3.10 (2H, t, J=7Hz), 3.7~3.98(2H, m), 4.10 (2H, q, J=7Hz), 5.18(2H, m), 7.22~7.72 (20H, m) |
| F-39 | 15(S)l-b | CH$_2$=CH— | $^t$BuPh$_2$Si— | CH$_3$ (isohexyl) | 80.5 | 914 (MH$^+$) 856 (M$^+$—$^t$Bu) | | (CHCl$_3$) 1731, 1638, 1591, 1111 | (CDCl$_3$) 0.79(6H, m), 1.02(18H, s), 1.23(3H, t, J=7Hz), 2.95~3.40(2H, m), 3.67~4.15(2H, m), 4.14(2H, q, J=7Hz), 4.63~4.91(2H, m), 5.26(2H, m), 5.50~5.73(1H, m), 7.23~7.8(20H, m) |
| F-41 | 15(S)l-d | CH$_2$=CH— | $^t$BuPh$_2$Si— | CH$_3$ (pentynyl) | 77 | 910 (MH$^+$) 852 (M$^+$—$^t$Bu) | | (CHCl$_3$) 1730, 1638, 1590, 1113 | (CDCl$_3$) 0.86(3H, m), 0.99(9H, s), 1.02(9H, s), 1.22(3H, t, J=7Hz), 1.72 (3H, s), 2.83~3.35(2H, m), 3.69(1H, m) 4.09(1H, m), 4.10(2H, q, J=7Hz), 4.58 ~4.85(2H, m), 5.16(2H, m), 5.42~5.77 (1H, m), 7.2~7.72(20H, m) |
| F-43 | 15(S)l-f | CH$_2$=CH— | $^t$BuPh$_2$Si— | cyclopentyl | 78 | 898 (MH$^+$) 840 (M$^+$—$^t$Bu) | −5.0 ± 0.7° (23° C., c = 0.676, CHCl$_3$) | (CHCl$_3$) 1730, 1639, 1590, 1113 | (CDCl$_3$) 1.01(18H, s), 1.23(3H, t, J=7Hz), 2.86~3.38(2H, m), 3.59~4.02 (2H, m), 4.12(2H, q, J=7Hz), 4.61~4.87 (2H, m), 5.19(2H, m), 5.45~5.8(1H, m), 7.2~7.8(20H, m) |
| F-69 | 15(S)g-f | CH≡C— | $^t$BuPh$_2$Si— | cyclopentyl | 92.5 | | −1.3 ± 0.8° (22° C., c = 0.537, CHCl$_3$) | (CHCl$_3$) 3312, 1731, 1591, 1581, 1112 | (CDCl$_3$) 0.99(9H, s), 1.00(9H, s), 1.23(3H, t, J=7Hz), 2.30(1H, s), 3.10(2H, t, J=7Hz), 3.67~4.0(2H, m), 4.11(2H, q, J=7Hz), 5.16(2H, m), 7.15~7.75(20H, m) |

TABLE 15-continued
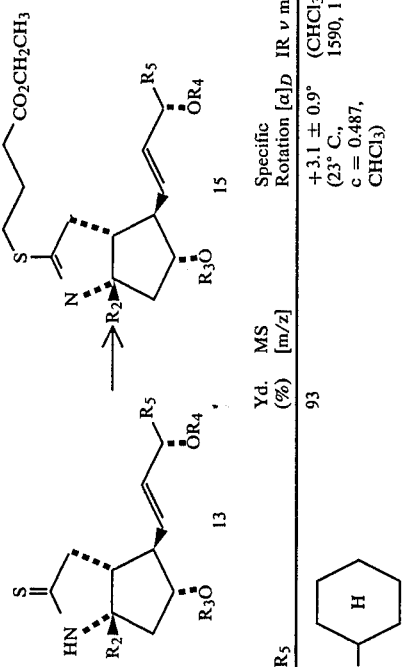
| Ex. No. | Compound No. | $R_2$ | $R_3, R_4$ | $R_5$ | Yd. (%) | MS [m/z] | Specific Rotation $[\alpha]_D$ | IR $\nu$ max [cm$^{-1}$] | NMR $\delta$ ppm |
|---|---|---|---|---|---|---|---|---|---|
| F-70 | 15(S)-e | $CH_2=CH-$ | $^tBuPh_2Si-$ | ![H cyclohexyl] | 93 | | +3.1 ± 0.9° (23° C., c = 0.487, CHCl$_3$) | (CHCl$_3$) 1730, 1639, 1590, 1113 | (CDCl$_3$) 1.00(9H, s), 1.02(9H, s), 1.23(3H, t, J=7Hz), 3.10(2H, m), 3.6–4.0(2H, m), 4.11(2H, q, J=7Hz), 4.58~4.85(2H, m), 5.20(2H, m), 5.42~5.76(1H, m), 7.2~7.75(20H, m) |

TABLE 16

Structure: (starting material 13 with HN-C(=S) thiolactam fused to cyclopentane bearing OR₃ and vinyl-CH=CH-CH(OR₄)-R₅, with R₂ on ring) → (product 15 with S-C(=N)... ring, N-CH₂CH₂CH₂CH₂-CO₂CH₂CH₃ chain, R₂ on ring, OR₃, and vinyl-CH(OR₄)-R₅)

| Ex. No. | Compound Number | R₂ | R₃, R₄ | R₅ | Yd. (%) | MS [m/z] | Specific Rotation [α]_D | IR ν max [cm⁻¹] | NMR δ ppm |
|---|---|---|---|---|---|---|---|---|---|
| F-24 | 15(R)g | CH≡C— | ᵗBuPh₂Si— | —CH₂CH₂CH₂CH₂CH₃ (n-pentyl) | 80.5 | 898 (MH⁺), 840 (M⁺—ᵗBu) | +41.6 ± 1.4° (23° C., c = 0.572 CHCl₃) | (CHCl₃) 3312, 1731, 1732, 1580, 1113 | (CDCl₃) 0.82(3H), 0.97(9H, s), 1.00(9H, s), 1.23(3H, t, J=7Hz), 2.27(1H, s), 3.08(2H, t, J=7Hz), 3.66~4.1(2H, m), 4.11(2H, q, J=7Hz), 4.74(1H, d-d, J=8, 16Hz), 5.36(1H, d-d, J=7, 16Hz), 7.21~7.71(20H, m) |
| F-26 | 15(R)g-b | CH≡C— | ᵗBuMe₂Si— | —CH₂CH₂CH₂CH(CH₃)CH₃ (isohexyl) | 92 | 911 (M⁺), 866 (M⁺—OEt), 854 (M⁺—ᵗBu) | | (CHCl₃) 3312, 1731, 1591, 1579, 1113 | (CDCl₃) 0.85(6H, m), 0.98(9H, s), 1.02(9H, s), 1.24(3H, t, J=7Hz), 2.29(1H, s), 3.09(2H, t, J=7Hz), 3.85(2H, m), 4.12(2H, q, J=7Hz), 4.76(1H, m), 5.43(1H, m), 7.15~7.8(20H, m) |
| F-28 | 15(S)g-c | CH≡C— | ᵗBuMe₂Si— | H₃C—C(CH₃)—CH₂CH₂CH₃ | 88 | 677 (M⁺), 632 (M⁺—OEt), 620 (M⁺—ᵗBu) | +33.0 ± 1.6° (24° C., c = 0.472, CHCl₃) | (CHCl₃) 3312, 1731, 1583, 1473, 1255, 1114, 1099, 1074, 868, 837 | (CDCl₃) −0.02(3H, s), 0.02(3H, s), 0.04(6H, s), 0.77(3H, s), 0.79(3H, s), 0.85(9H, s), 0.88(9H, s), 1.24(3H, t, J=7Hz), 2.44(1H, s), 3.13(2H, t, J=7Hz), 3.70(1H, m), 3.99(1H, m), 4.14(2H, q, J=7Hz), 5.46(2H, m) |
| F-30 | 15(R)g-d | CH≡C— | ᵗBuPh₂Si— | —CH(CH₃)—C≡C—CH₃ | 72 | 907 (M⁺), 862 (M⁺—OEt), 850 (M⁺—ᵗBu) | | (CHCl₃) 3312, 1730, 1591, 1580, 1113 | (CDCl₃) 0.88(3H, m), 0.97(9H, s), 1.00(9H, s), 1.24(3H, t, J=7Hz), 1.78(3H), 2.27(1H, s), 3.07(2H, t, J=7Hz), 3.73(1H, m), 4.05(1H, m), 4.12(2H, q, J=7Hz), 4.67(1H, m), 5.37(1H, m), 7.15~7.8(20H, m) |
| F-32 | 15(R)g-e | CH≡C— | ᵗBuPh₂Si— | cyclohexyl | 92 | 910 (MH⁺), 864 (M⁺—OEt), 852 (M⁺—ᵗBu) | +35.1 ± 1.9° (22° C., c = 0.405, CHCl₃) | (CHCl₃) 3312, 1730, 1591, 1580, 1113 | (CDCl₃) 0.98(9H, s), 1.02(9H, s), 1.24(3H, t, J=7Hz), 2.29(1H, s), 3.09(2H, t, J=7Hz), 3.80(2H, m), 4.13(2H, q, J=7Hz), 4.64(1H, d-d, J=8, 15Hz), 7.15~7.75(20H, m) |

TABLE 16-continued

| Ex. No. | Compound Number | $R_2$ | $R_3, R_4$ | $R_5$ | Yd. (%) | MS [m/z] | Specific Rotation $[\alpha]_D$ | IR $\nu$ max [cm$^{-1}$] | NMR $\delta$ ppm |
|---|---|---|---|---|---|---|---|---|---|
| F-34 | 15(R)g-g | CH≡C— | $^t$BuPh$_2$Si— | (furan with propyl) | 92.5 | 921 (M$^+$)<br>876 (M$^+$—OEt)<br>864 (M$^+$—$^t$Bu) | +38.3 ± 1.5° (24° C., c = 0.540, CHCl$_3$) | (CHCl$_3$) 3312, 1730, 1591, 1580, 1113 | (CDCl$_3$) 0.97(9H, s), 1.02(9H, s), 1.24(3H, t, J=7Hz), 2.30(1H, s), 3.11 (2H, t, J=7Hz), 3.80(1H, m), 4.06(1H, m), 4.14(2H, q, J=7Hz), 4.74(1H, d-d, J=7.5, 15Hz), 5.38(1H, d-d, J=8, 15Hz ), 5.85(1H), 6.26(1H, m), 7.2~7.75 (21H, m) |
| F-36 | 15(R)h-b | CH$_3$—C≡C— | $^t$BuPh$_2$Si— | CH$_3$—CH(CH$_3$)—CH$_2$CH$_2$CH$_2$— | 71.5 | 926 (M$^+$)<br>868 (M$^+$—$^t$Bu) | | (CHCl$_3$) 1731, 1591, 1582, 1113 | (CDCl$_3$) 0.82(6H, m), 0.97(9H, s), 1.01(9H, s), 1.23(3H, t, J=7Hz), 1.71 (3H, s), 3.09(2H, t, J=7Hz), 3.65~4.05 (2H, m), 4.11(2H, q, J=7Hz), 4.57~5.05 (1H, m), 5.24~5.63(1H, m), 7.15~7.75 (20H, m) |
| F-38 | 15(R)h-e | CH$_3$—C≡C— | $^t$BuPh$_2$Si— | cyclohexyl | 91 | 924 (MH$^+$)<br>866 (M$^+$—$^t$Bu) | +32.4 ± 1.2° (23° C., c = 0.624, CHCl$_3$) | (CHCl$_3$) 1730, 1582, 1113 | (CDCl$_3$) 0.96(9H, s), 1.00(9H, s), 1.23(3H, t, J=7Hz), 1.70(3H, s), 3.06 (2H, t, J=7Hz), 3.63~3.95(2H, m), 4.10 (2H, q, J=7Hz), 4.81(1H, d-d, J=8, 16Hz ), 5.37(1H, d-d, J=7, 16Hz), 7.2~7.75 (20H, m) |
| F-40 | 15(R)l-b | CH$_2$=CH— | $^t$BuPh$_2$Si— | CH$_3$—CH(CH$_3$)—CH$_2$CH$_2$CH$_2$— | 84.5 | 914 (MH$^+$)<br>856 (M$^+$—$^t$Bu) | | (CHCl$_3$) 1731, 1638, 1586, 1113 | (CDCl$_3$) 0.85(6H, m), 0.98(9H, s), 1.01(9H, s), 1.23(3H, t, J=7Hz), 2.85 ~3.35(2H, m), 3.53~4.05(2H, m), 4.14 (2H, q, J=7Hz), 4.53~4.97(3H, m), 5.38 ~5.80(2H, m), 7.23~7.78(20H, m) |
| F-42 | 15(R)l-d | CH$_2$=CH— | $^t$BuPh$_2$Si— | CH$_3$—CH(CH$_3$)—C≡C— | 76 | 910 (MH$^+$)<br>852 (M$^+$—$^t$Bu) | | (CHCl$_3$) 1730, 1639, 1585, 1112 | (CDCl$_3$) 0.93(3H, m), 0.97(9H, s), 1.00(9H, s), 1.24(3H, t, J=7Hz), 1.79 (3H), 2.82~3.32(2H, m), 3.63(1H, m), 4.12(2H, q, J=7Hz), 4.13(1H, m), 4.46 ~4.85(3H, m), 5.20~5.74(2H, m), 7.23 ~7.78(20H, m) |

TABLE 16-continued

| Ex. No. | Compound Number | R₂ | R₃, R₄ | R₅ | Yd. (%) | MS [m/z] | Specific Rotation [α]_D | IR ν max [cm⁻¹] | NMR δ ppm |
|---|---|---|---|---|---|---|---|---|---|
| F-44 | 15(R)l-f | CH₂=CH— | ᵗBuPh₂Si— | cyclopentyl | 86.5 | 898 (MH⁺) 840 (M⁺—ᵗBu) | +33.7 ± 1.8° (23° C., c = 0.407, CHCl₃) | (CHCl₃) 1731, 1638, 1586, 1113 | (CDCl₃) 0.97(9H, s), 0.99(9H, s), 1.23(3H, t, J=7Hz), 2.83~3.32(2H, m), 3.50~4.02(2H, m), 4.13(2H, q, J=7Hz), 4.47~4.85(3H, m), 5.26~5.73(2H, m), 7.22~7.8(20H, m) |
| F-71 | 15(R)g-f | CH≡C— | ᵗBuPh₂Si— | cyclopentyl | 84 | | +41.0 ± 1.4° (22° C., c = 0.564, CHCl₃) | (CHCl₃) 3312, 1731, 1591, 1579, 1113 | (CDCl₃) 0.97(9H, s), 1.00(9H, s), 1.23(3H, t, J=7Hz), 2.28(1H, s), 3.07(2H, t, J=7Hz), 3.6~4.0(2H, m), 4.12(2H, q, J=7Hz), 4.62(1H, d-d, J=7.5, 15.5Hz), 5.35(1H, d-d, J=8, 15.5Hz), 7.15~7.75(20H, m) |
| F-72 | 15(R)l-e | CH₂=CH— | ᵗBuPh₂Si— | cyclohexyl (H) | 93 | | | | (CDCl₃) 0.97(9H, s), 1.00(9H, s), 1.23(3H, t, J=7Hz), 3.08(2H, m), 3.5–3.93(2H, m), 4.11(2H, q, J=7Hz), 4.47~4.8(3H, m), 5.26~5.73(2H, m), 7.15~7.75(20H, m) |

Example F-45

Preparation of ethyl 4-[1-ethynyl-7-hydroxy-6-[(3S)-3-hydroxy-1-octenyl]-2-azabicyclo[3.3.0]oct-2-en-3-yl]thiobutanoate 17(S)g

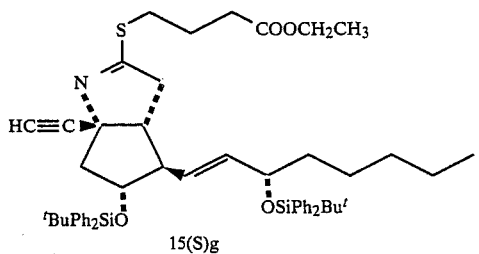

15(S)g

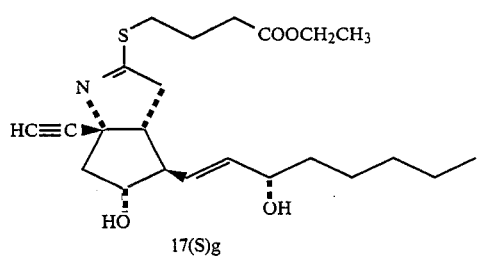

17(S)g

To a solution of 254 mg (0.283 mmol) of the silyl ether 15(S)g (Example I-23) in 8 ml of dry tetrahydrofuran is added 1.7 ml (1.7 mmol) of 1M tetrahydrofuran solution of tetra-n-butyl ammonium fluoride in an atmosphere of nitrogen and the mixture is allowed to stand at room temperature overnight. Saturated aqueous solution of ammonium chloride is added to the reaction mixture, which is then extracted with ethyl acetate twice. The extract is washed with saturated aqueous solution of sodium chloride, dried over anhydrous magnesium sulfate, and evaporated to give 297 mg of a residue, which is applied to column chromatography (15 g of alumina; eluted with benzene: ethyl acetate=1:1-ethyl acetate:methanol=1:1) to give 117 mg of an oily product. Further purification by column chromatography (Lober column, size A, 2 columns; eluted with benzene:ethyl acetate=2:3—ethyl acetate) affords 99 mg of the compound 17(S)g as an oil (83% yield).

MS: m/z 421 (M+), m/z 376 (M+—OCH$_2$CH$_3$).

$[\alpha]_D^{22}$ +45.4±1.2° (c=0.715, CHCl$_3$).

IR: $\nu_{max}^{CHCl_3}$ 3604, 3408, 3312, 1729, 1579, 1084, 1049, 971 cm$^{-1}$.

NMR: $\delta_{ppm}^{CDCl_3}$ 0.88 (3H), 1.25 (3H, t, J=7 Hz), 2.45 (1H, s), 3.13 (2H, m), 3.8–4.25 (2H, m), 4.14 (2H, q, J=7 Hz), 5.53 (2H, m).

Example F-46–F-66 and F-73–F-75

Removal of silyl groups are carried out in the same manner as in Example F-45 and results are shown in Tables 17 and 18.

TABLE 17

[Structure: compound 15 (with R₃O, OR₄, R₅, R₂ substituents, CO₂CH₂CH₃ group) → compound 17 (with OH, R₅, R₂ substituents, CO₂CH₂CH₃ group)]

| Ex. Number | Compd. Number | R₂ | R₅ | Yield (%) | MS [m/z] | Specific Rotation [α]_D | IR ν max [cm⁻¹] | NMR δ ppm |
|---|---|---|---|---|---|---|---|---|
| F-47 | 17(S)g-b | CH≡C— | CH₃ (2-methylpentyl) | 77 | 435 (M⁺) 390 (M⁺—OEt) | | (CHCl₃) 3608, 3428, 3312, 1730, 1581, 1083, 1049, 973 | (CDCl₃) 0.88(6H, m), 1.25(3H, t, J=7Hz), 2.44(1H, s), 3.12(2H, m), 3.88(2H, m), 4.12(2H, q, J=7Hz), 5.52 (2H, m) |
| F-49 | 17(R)g-c | CH≡C— | H₃C CH₃ (2-methylpentyl, stereo) | 74.5 | 449 (M⁺) 404 (M⁺—OEt) | +58.5 ± 1.4° (23° C., c = 0.709, CHCl₃) | (CHCl₃) 3612, 3424, 3312, 1729, 1580, 1085, 1050, 975 | (CDCl₃) 0.81(3H, s), 0.86(3H, s), 0.88(3H), 1.25(3H, t, J=7Hz), 2.44 (1H, s), 3.12(2H, m), 3.76(1H, d, J=7Hz), 4.02(1H, m), 4.12(2H, q, J=7Hz), 5.50(2H, m) |
| F-51 | 17(S)g-d | CH≡C— | CH₃ (with alkyne) | 84 | 431 (M⁺) 386 (M⁺—OEt) | | (CHCl₃) 3608, 3424, 3312, 1731, 1580, 1084, 1051, 973 | (CDCl₃) 0.93(3H, m), 1.23(3H, t, J=7Hz), 1.75(3H, t, J=2.5Hz), 2.44 (1H, s), 3.11(2H, m), 4.0(2H, m), 4.12(2H, q, J=7Hz), 5.55(2H, m) |
| F-53 | 17(S)g-e | CH≡C— | (cyclohexyl) | 86 | 433 (M⁺) 388 (M⁺—OEt) | +50.0 ± 1.8° (24° C., c = 0.500, CHCl₃) | (CHCl₃) 3608, 3424, 3312, 1731, 1581, 1087, 1051, 973 | (CDCl₃) 1.25(3H, t, J=7Hz), 2.43(1H, s), 3.11(2H, m), 3.80(2H, m), 4.11 (2H, q, J=7Hz), 5.48(2H, m) |
| F-55 | 17(S)g-g | CH≡C— | (furyl) | 83 | 445 (M⁺) 400 (M⁺—OEt) | +45.3 ± 2.1° (24° C., c = 0.408, CHCl₃) | (CHCl₃) 3608, 3408, 3312, 1730, 1580, 1080, 1050, 1008, 973 | (CDCl₃) 1.24(3H, t, J=7Hz), 2.46(1H, s), 3.10(2H, m), 3.7~4.2(2H, m), 4.12(2H, q, J=7Hz), 5.53(2H, m), 5.98 (1H, m), 6.27(1H, m), 7.28(1H) |
| F-57 | 17(S)h-b | CH₃—C≡C— | CH₃ | 67 | | | (CHCl₃) 3608, 3424, 1730, 1581, 1083, 1037, 972 | (CDCl₃) 0.88(6H, m), 1.24(3H, t, J=7 Hz), 1.79(3H, s), 3.12(2H, m), 3.75~4.1(2H, m), 4.11(2H, q, J=7Hz), 5.51(2H, m) |
| F-59 | 17(S)h-e | CH₃—C≡C— | (cyclohexyl) | 77.5 | 447 (M⁺) 402 (M⁺—OEt) | +26.6 ± 1.4° (23° C., c = 0.463, CHCl₃) | (CHCl₃) 3608, 3424, 1729, 1582, 1083, 1042, 973 | (CDCl₃) 1.26(3H, t, J=7Hz), 1.80(3H, s), 3.13(2H, m), 3.66~4.10(2H, m), 4.12(2H, q, J=7Hz), 5.50(2H, m) |

TABLE 17-continued

| Ex. Number | Compd. Number | R2 | R5 | Yield (%) | MS [m/z] | Specific Rotation [α]D | IR ν max [cm⁻¹] | NMR δ ppm |
|---|---|---|---|---|---|---|---|---|
| F-61 | 17(S)l-b | CH$_2$=CH— | CH$_3$ branched with CH$_3$ (pentyl) | 78.5 | 437 (M$^+$) 392 (M$^+$—OEt) | | (CHCl$_3$) 3608, 3428, 1730, 1640, 1585, 1081, 1040, 973 | (CDCl$_3$) 0.87(6H, m), 1.24(3H, t, J=7Hz), 3.13(2H, t, J=7Hz), 3.87(2H, m), 4.11(2H, q, J=7Hz), 4.80~5.06 (2H, m), 5.51(2H, m), 5.88(1H, d-d, J=10, 18Hz) |
| F-63 | 17(S)l-d | CH$_2$=CH— | CH$_3$ with C≡C (heptynyl) | 84.5 | 433 (M$^+$) 388 (M$^+$—OEt) | | (CHCl$_3$) 3608, 3428, 1729, 1639, 1585, 1081, 1038, 972 | (CDCl$_3$) 0.94(3H, m), 1.25(3H, t, J=7Hz), 1.77(3H), 3.13(2H, t, J=7Hz), 3.69~4.24(2H, m), 4.12(2H, q, J=7Hz), 4.8~5.07(2H, m), 5.54(2H, m), 5.89(1H, d-d, J=10, 18Hz) |
| F-65 | 17(S)l-f | CH$_2$=CH— | cyclopentyl | 81.5 | 421 (M$^+$) 376 (M$^+$—OEt) | +54.7 ± 1.0° (23° C., c = 0.978, CHCl$_3$) | (CHCl$_3$) 3608, 3420, 1730, 1639, 1585, 1080, 1039, 972 | (CDCl$_3$) 1.25(3H, t, J=7Hz), 3.14(2H, t, J=7Hz), 3.83(2H, m), 4.15(2H, q, J=7Hz), 4.82~5.1(2H, m), 5.53(2H, m), 5.92(1H, d-d, J=10, 18Hz) |
| F-73 | 17(S)g-f | CH≡C— | cyclopentyl | 69.5 | | +49.5 ± 1.2° (23° C., c = 0.725, CHCl$_3$) | (CHCl$_3$) 3608, 3428, 3312, 1730, 1580, 1082, 1049, 972 | (CDCl$_3$) 1.25(3H, t, J=7Hz), 2.44(1H, s), 3.10(2H, m), 3.7~4.0(2H, m), 4.12(2H, q, J=7Hz), 5.51(2H, m) |
| F-75 | 17(S)l-e | CH$_2$=CH— | cyclohexyl | 83 | | | | (CDCl$_3$) 1.24(3H, t, J=7Hz), 3.14(2H, t, J=7Hz), 3.80(2H, m), 4.14(2H, q, J=7Hz), 4.8~5.1(2H, m), 5.50(2H, m), 5.73~6.1(1H, m). |

TABLE 18

Structure 15 → Structure 17

| Ex. Number | Compd. Number | $R_2$ | $R_5$ | Yield (%) | MS [m/z] | Specific Rotation $[\alpha]_D$ | IR $\nu_{max}$ [cm$^{-1}$] | NMR $\delta$ ppm |
|---|---|---|---|---|---|---|---|---|
| F-46 | 17(R)g | CH≡C— | hexyl | 81.5 | 421 (M$^+$), 376 (M$^+$—OEt) | +38.4 ± 2.2° (23 °C, c = 0.365, CHCl$_3$) | (CHCl$_3$) 3608, 3440, 3312, 1730, 1082, 1050, 974 | (CDCl$_3$) 0.87 (3H), 1.24 (3H,t, J=7Hz), 2.46 (1H,s), 3.07 (2H,m), 3.83~4.28 (2H,m), 4.14 (2H,q,J=7Hz), 5.61 (2H,m) |
| F-48 | 17(R)g-b | CH≡C— | 5-methylhexyl | 54 | 435 (M$^+$), 390 (M$^+$—OEt) |  | (CHCl$_3$) 3612, 3440, 3312, 1730, 1081, 975 | (CDCl$_3$) 0.88 (6H,m), 1.25 (3H,t, J=7Hz), 2.46 (1H,s), 3.13 (2H,m), 3.97 (2H,m), 4.12 (2H,q,J=7Hz), 5.59 (2H,m) |
| F-50 | 17(S)g-c | CH≡C— | H$_3$C, CH$_3$ branched chain | 82.5 | 449 (M$^+$), 404 (M$^+$—OEt) | +30.3 ± 1.7° (23 °C, c = 0.416, CHCl$_3$) | (CHCl$_3$) 3612, 3460, 3312, 1730, 1580, 1082, 1051, 975 | (CDCl$_3$) 0.83 (3H,s), 0.86 (3H,s), 0.89 (3H), 1.25 (3H,t,J=7Hz), 2.45 (1H,s), 3.10 (2H,m), 3.82 (1H,d, J=5Hz), 4.03 (1H,m), 4.12 (2H,q, J=7Hz), 5.62 (2H,m) |
| F-52 | 17(R)g-d | CH≡C— | CH$_3$ branched alkyne | 76 | 431 (M$^+$), 386 (M$^+$—OEt) |  | (CHCl$_3$) 3612, 3520, 3312, 1731, 1580, 1078, 974 | (CDCl$_3$) 0.96 (3H,d,J=7Hz), 1.24 (3H, t,J=7Hz), 1.77 (3H,t,J=2.5Hz), 2.47 (1H,s), 3.13 (2H,m), 4.05 (2H,m), 4.14 (2H,q,J=7Hz), 5.63 (2H,m) |
| F-54 | 17(R)g-e | CH≡C— | cyclohexyl | 66.5 | 433 (M$^+$), 388 (M$^+$—OEt) | +32.5 ± 1.6° (24 °C, c = 0.449, CHCl$_3$) | (CHCl$_3$) 3612, 3312, 1731, 1580, 1081, 974 | (CDCl$_3$) 1.25 (3H,t,J=7Hz), 2.46 (1H, s), 3.11 (2H,m), 3.90 (2H,m), 4.11 (2H,q,J=7Hz), 5.57 (2H,m) |
| F-56 | 17(R)g-g | CH≡C— | furyl-propyl | 84.5 | 445 (M$^+$), 400 (M$^+$—OEt) | +34.9 ± 1.7° (24 °C, c = 0.439, CHCl$_3$) | (CHCl$_3$) 3608, 3448, 3312, 1729, 1580, 1078, 1053, 1008, 974 | (CDCl$_3$) 1.24 (3H,t,J=7Hz), 2.46 (1H, s), 3.10 (2H,m), 3.8~4.2 (2H,m), 4.11 (2H,q,J=7Hz), 5.60 (2H,m), 5.95 (1H,m), 6.27 (1H), 7.29 (1H) |

TABLE 18-continued

[Structure: 15 → 17, showing transformation of thiazoline-containing bicyclic compound with CO2CH2CH3 and OR4 groups to compound with OH groups]

| Ex. Number | Compd. Number | R2 | R5 | Yield (%) | MS [m/z] | Specific Rotation [α]D | IR νmax [cm⁻¹] | NMR δ ppm |
|---|---|---|---|---|---|---|---|---|
| F-58 | 17(R) h-b | CH₃—C≡C— | CH(CH₃)CH₂CH₂CH₂CH₃ | 54 | | | (CHCl₃) 3612, 3448, 1730, 1582, 1082, 1038, 975 | (CDCl₃) 0.87 (6H,m), 1.25 (3H, t, J = 1.80 (3H, s), 3.12 (2H,m), 3.83-4.17 (2H, m), 4.12 (2H, q,J=7Hz), 5.58 (2H,m) |
| F-60 | 17(R) h-e | CH₃—C≡C— | cyclohexyl-CH₃ | 65 | 447 (M⁺) 402 (M⁺—OEt) | +15.1 ± 1.3° (21 °C. c = 0.430, CHCl₃) | (CHCl₃) 3612, 3468, 1730, 1582, 1078, 1040, 974 | (CDCl₃) 1.24 (3H,t,J=7Hz), 1.80 (3H, s), 3.10 2H,m), 3.85 (2H,m), 4.11 (2H,q,J=7Hz), 5.57 (2H,m) |
| F-62 | 17(R) l-e | CH₂=CH— | CH(CH₃)CH₂CH₂CH₂CH₃ | 58 | 437 (M⁺) 392 (M⁺—OEt) | | (CHCl₃) 3610, 3450, 1729, 1638, 1583, 1078, 1037, 974 | (CDCl₃) 0.85 (6H,m), 1.24 (3H,t, J=7Hz), 3.13 (2H,t,J=7Hz), 3.93 (2H, m), 4.11 (2H,q,J=7Hz), 4.81~5.07 (2H,m), 5.57 (2H,m), 5.88 (1H,d—d, J=10, 18Hz) |
| F-64 | 17(R) l-d | CH₂=CH— | CH(CH₃)C≡C-CH₂CH₃ | 70 | 433 (M⁺) 388 (M⁺—OEt) | | (CHCl₃) 3612, 3524, 1730, 1640, 1586, 1079, 1039, 974 | (CDCl₃) 0.96 (3H,d,J=7Hz), 1.24 (3H, t,J=7Hz), 1.77 (3H), 3.13 (2H,t, J=7Hz), 3.74~4.25 (2H,m), 4.12 (2H, q,J=7Hz), 4.81~5.07 (2H,m), 5.59 (2H,m), 5.89 (1H,d—d,J=10, 18Hz) |
| F-66 | 17(R) l-f | CH₂=CH— | cyclopentyl | 70.5 | 421 (M⁺) 376 (M⁺—OEt) | +41.4 ± 1.8° (23 °C. c = 0.459, CHCl₃) | (CHCl₃) 3612, 3460, 1730, 1640, 1585, 1079, 1040, 974 | (CDCl₃) 1.24 (3H,t,J=7Hz), 3.13 (2H, t,J=7Hz), 3.90 (2H,m), 4.11 (2H,q, J=7Hz), 4.8~5.06 (2H,m), 5.57 (2H, m), 5.90 (1H,d—d,J=10, 18Hz) |
| F-74 | 17(R) g-f | CH≡C— | cyclopentyl | 64 | | | | (CDCl₃) 1.24 (3H,t,J=7Hz), 2.46 (1H, s), 3.10 2H,m), 3.77-4.1 (2H,m), 4.11 (2H,q,J=7Hz), 5.60 (2H,m) |

Example F-67

Preparation of sodium 4-[1-ethynyl-7-hydroxy-6-[(3S)-3-cyclohexyl-3-hydroxy-1-propenyl]-2-azabicyclo[3.3.0]oct-2-en-3-yl]thiobutanoate 19(S)g−e

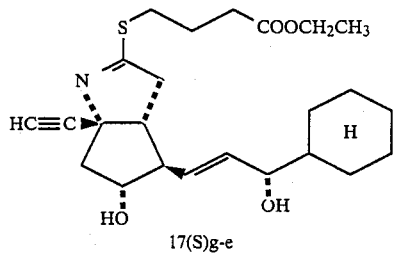
17(S)g-e

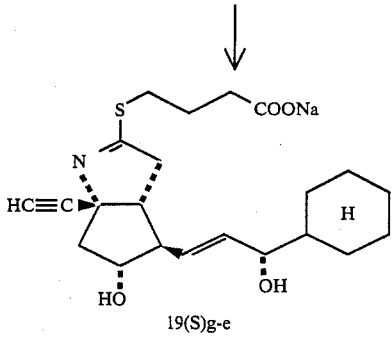
19(S)g-e

To a solution of 57 mg (0.131 mmol) of the ethyl ester 17(S)g−e (Example F-53) in 2 ml of methanol are added 1.27 ml (0.127 mmol) of 0.1N aqueous solution of sodium hydroxide and 0.6 ml of water, and the mixture is allowed to stand for 2 days. The reaction mixture is evaporated under reduced pressure and the residue is washed well with diethyl ether. The insoluble material is dissolved in methanol and the mixture is evaporated again. The residue is washed with diethyl ether. This operation is repeated and the residue is dried to give 47 mg of the compound 19(S)g−e as a foamy material.

IR: $\lambda_{max}^{KBr}$ 3400, 3300, 1573, 1407, 1088 cm$^{-1}$.

NMR: $\delta_{ppm}^{D2O}$ (External Standard) 4.1–4.7 (2H, m), 6.03 (2H, m).

Example F-68

Preparation of sodium 4-[7-hydroxy-6-[(3S)-3-hydroxy-1-octenyl]-1-(1-propynyl)-2-azabicyclo[3.3.0]oct-2-en-3-yl]thiobutanoate 19(S)h

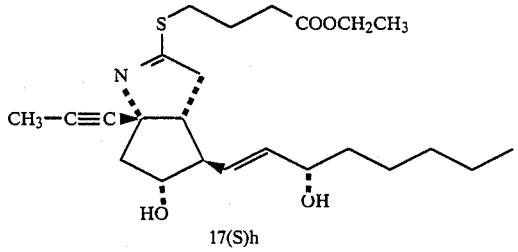
17(S)h

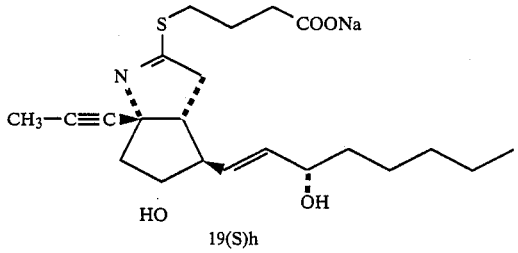
19(S)h

The ethyl ester 17(S)h (64 mg; Example F-13) is allowed to react in the same manner as in Example F-67 to give 50 mg of the compound 19(S)h as a foamy material.

IR: $\nu_{max}^{KBr}$ 3400, 1573, 1405, 1085 cm$^{-1}$.

NMR: $\delta_{ppm}^{D2O}$ (External Standard) 2.30 (3H, s), ~4.50 (2H, m), 6.03 (2H).

Effect of the Invention

The compounds of the present invention are chemically stable analogues of prostacylin (PGI$_2$) which act as agonists to PGI$_2$ receptor. The compounds of the present invention strongly inhibit platelet agglutination as well as PGI$_2$ so that they are expected to be useful as antithrombotic drugs for the improvement of peripheral circulatory insufficiency, extracporeal circulation such as artificial dialysis or ischemic disease, and the like. Besides, having an antiulcer activity, the compounds of the present invention may be used as antiulcer drugs.

The inhibitory activity of the representative compounds of the present invention against platelet agglutination is shown in the following in vitro test.

[Materials tested and Methods]

Mature male rabbits (NIBS-JW, RABITON Institute Inc., weighing 2.2–2.7 kg) were used. Under sodium pentobarbital anesthesia (Somnopentyl, Pitman Movre, about 25 mg/Kg, i.v.), blood was with from the carotid artery by cannulation into centrifuge tubes containg 1/10 vol of a 3.8% sodium citrate solution. (The total volume in each tube was adjusted to 8 ml.) The blood in a tube was gentyl mixed by turing and centrifuged for 10 minutes at 210 g at 20° C. to give platelet rich plasma (PRP). The remaining blood was further centrifuged at 3,000 rpm (about 1,900 g) for 10 minutes at 20° C. to give platelet-poor plasma (PPP).

PRP was diluted with PPP to prepare a blood sample whose platelet number was 50–55×10$^4$/µl. The sample was then subjected to a platelet agglutination test.

The platelet agglutination was examined by the method of Bron [Born, G.V.R., Nature, 194, 927–929 (1962)], using a Type AUTO RAM-61 aggregometer, (Rika Denki Co., Ltd., Tokyo). A volume of 400 µl of PRP, whose platelet number was adjusted to 50–55×10$^4$/µl, was placed in a measuring cuvette and set in the aggregometer. PRP was warmed at 37° C. for 1 minute with stirring at 1,200 rpm, and then a solution of the test compound [dimethylsulfoxide solution (2 µl) of the compound+saline (48 µl); in case of prostaglandin I$_2$ (PGI$_2$) and prostaglandin E$_1$ (PG E$_1$), a solution of each compound (50 µl) in Tris buffer] was added thereto. Exactly 2 minutes later, 50 µl of ADP Pharmacia, U.S.A., (final concentration: 30 µM) or collagen (final muchen, muchen, concentration: 20 µg/ml) or arachidonic acid (sodium salt, Sigma, final concentration (500 µM) was added as a platelet agglutinating agent, and the change in light transmission caused by platelet agglutination was recorded.

The light transmissions of PRP and PPP were taken as 0% and 100% agglutination, respectively, and the maximum light transmission after addition of an agglutinating agent was made to the maxiumum agglutination. The inhibition rate of the platelet agglutination was expressed as the percentage of the maximum agglutination by a test compound to that by a control (Vehicle added group).

[Results]

The results of the test are shown in Table 19.

Prostaglandin (PG) $I_2$ and $E_1$ are served as standard substances.

TABLE 19

| Inhibition Activity against Platelet Agglutination [50% Inhibition Concentration (μM)] | | | |
|---|---|---|---|
| | Platelet Agglutinating Agent | | |
| Test Compound | Arachidonic acid | Collagen | ADP |
| 17(S)a | 21 | 8 | 16 |
| 17(S)b | 16 | 7 | 15 |
| 17(S)d | 160 | 9 | 18 |
| 17(S)e | 4.4 | 0.6 | 1.6 |
| 17(S)g | 0.02 | 0.006 | 0.011 |
| 17(S)h | 0.01 | 0.0013 | 0.006 |
| 17(S)i | 44 | 0.45 | 5.0 |
| 17(S)k | 0.74 | 0.053 | 0.27 |
| 18(S)g | 0.081 | 0.011 | 0.0241 |
| 19(S)g | 0.0093 | 0.0093 | 0.0049 |
| $PGI_2$ (pH8.0) | 0.054 | 0.019 | 0.014 |
| $PGI_2$ (pH10.0) | 0.090 | 0.020 | 0.016 |
| $PGE_1$ (pH7.4) | 0.25 | 0.052 | 0.066 |
| 18c | 0.16 | 0.062 | 0.074 |
| Hoe-892 | | | |
| 17(S)m | 0.332 | 0.044 | 0.167 |
| 17(S)l | 0.70 | 0.10 | 0.42 |
| 17(S)g-b | 0.012 | 0.0013 | 0.0066 |
| 17(S)g-d | 0.018 | 0.0042 | 0.014 |
| 17(S)g-e | 0.146 | 0.0094 | 0.033 |
| 17(S)l-d | 0.36 | 0.048 | 0.13 |
| 17(S)l-f | 1.2 | 0.12 | 0.30 |
| 17(R)g-b | 1.55 | 0.54 | 2.06 |
| 17(R)g-d | 11.7 | 4 | 8.43 |
| 17(R)g-e | 60.6 | 3 | 13.4 |
| 17(R)l-d | 118 | 23 | 55 |
| 17(R)l-f | 443 | 54 | 142 |
| 19(S)h | 0.0035 | 0.0028 | 0.0042 |

*Compound number corresponds to that used in Example or that described below.

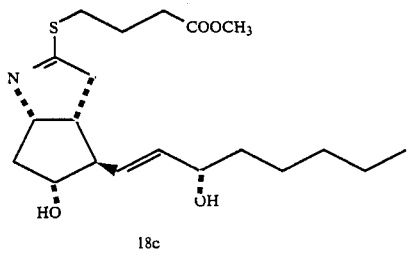

18c

The compounds of the present invention strongly inhibit the platelet agglutination induced by arachidonic acid, collagen and ADP. The compounds of the present invention act as agonist to $PGI_2$ receptor and strongly inhibit the platelet agglutination. Therefore, clinical application of the compounds having such pharmacological action can be expected, that is, the compounds can be used for extracorporeal circulation, e.g., artificial dialysis, pump-oxygenator; prevention of thrombosis caused after operation; or treatment or prevention of peripheral circulatory insufficiency or ischemic disease, e.g., vibration disease, Bueger disease, arteriosclerosis obliteration, plumonary, embolism, plumonary hypertension, angina pectoris, acute myocardial infarction, cerebral thrombosis, cerebral embolism, cerebral infraction.

For oral administration, the compounds are prepared to the dosage forms such as tablets, capsules, pills, granules, fine subtilaes, solutions, or emulsions and for parenteral administration, such as suppositories or onjections, e.g., intravenous, intramuscular or subcutaneous injection. When the pharmaceutical preparations of the compounds are prepared, adequated carriers and fillers are selected from conventionally used carriers and fillers.

The compounds of the present invention are to be orally administered to the adult in a daily dose of about 0.1 mg–500 mg.

What we claim is:

1. A compound represented by the formula:

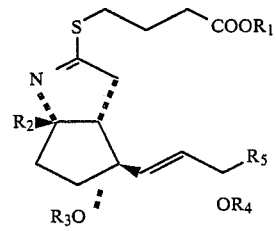

wherein $R_1$ is hydrogen or lower alkyl; $R_2$ is lower alkynyl; $R_3$ and $R_4$ each is hydrogen; $R_5$ is straight or branched $C_1$–$C_8$ alkyl which may be substituted with nitrogen-, oxygen-, or sulfur-containing 5-membered heterocycle, straight or branched $C_2$–$C_8$ alkynyl, or $C_3$–$C_8$ cycloalkyl; the wavy line indicates an R- or S-configuration, or their mixture; or a salt thereof.

2. A compound claimed in claim 1, wherein $R_5$ is straight or branched alkyl which may be substituted with said heterocycle.

3. A compound claimed in claim 1, wherein $R_5$ is straight or branched alkynyl.

4. A compound claimed in claim 1, wherein $R_5$ is straight or branched alkyl which is substituted with said heterocycle.

5. A compound claimed in claim 1 wherein the lower alkynyl of $R_2$ is ethynyl, 1-propynyl, 1,3-butadiynyl, or phenylethynyl.

6. A compound claimed in claim 1, namely, 4-[1-ethynyl-7-hydroxy-6-(3-hydroxy-1-octenyl)-2-azabicyclo[3.3.0]oct-2-en-3-yl]thiobutanoic acid or a salt or ester thereof.

7. A compound claimed in claim 1, namely, 4-[7-hydroxy-6-(3-hydroxy-1-octenyl)-1-(1-propynyl)-2-azabicyclo[3.3.0]oct-2-en-3-yl]thiobutanoic acid or a salt or ester thereof.

8. A compound claimed in claim 1, namely, 4-[1-(1,3-butadiynyl)-7-hydroxy-6-(3-hydroxy-1-octenyl)-2-azabicyclo[3.3.0]oct-2-en-3-yl]thiobutanoic acid or a salt or ester thereof.

9. A compound claimed in claim 1, namely, 4-[1-ethynyl-7-hydroxy-6-(3-hydroxyl-4-methyl-1-octenyl)-2-azabicyclo[3.3.0]oct-2-en-3-yl]thiobutanoic acid or a salt or ester thereof.

10. A compound claimed in claim 1, namely, 4-[7-hydroxy-6-(3-hydroxy-4-methyl-1-octen-6-ynyl)-1-(1-propynyl)-2-azabicyclo[3.3.0]oct-2-en-3-yl]thiobutanoic acid or a salt or ester thereof.

11. A compound claimed in claim 1, namely, 4-[1-ethynyl-7-hydroxy-6-(3-hydroxy-4,4-dimethyl-1-octenyl)-2-azabicyclo[3.3.0]oct-2-en-3-yl]thiobutanoic acid or a salt or ester thereof.

12. A compound claimed in claim 1, namely, 4-[1-ethynyl-7-hydroxy-6-(3-hydroxy-4-methyl-1-octen-6-ynyl)-2-azabicyclo[3.3.0]oct-2-en-3-yl]thiobutanoic acid or a salt or ester thereof.

13. A compound claimed in claim 1, namely, 4-[6-(3-cyclopentyl-3-hydroxy-1-propenyl)-1-ethynyl-7-hydroxy-2-azabicyclo[3.3.0]oct-2-en-3-yl]thiobutanoic acid or a salt or ester thereof.

14. A compound claimed in claim 1, namely, 4-[6-(3-cyclohexyl-3-hydroxy-1-propenyl)-1-ethynyl-7-hydroxy-2-azabicyclo[3.3.0]oct-2-en-3-yl]thiobutanoic acid or a salt or ester thereof.

15. A compound claimed in claim 1, namely, 4-[6-(3-cyclohexyl-3-hydroxy-1-propenyl)-7-hydroxy-1-(1-propynyl)-2-azabicyclo[3.3.0]oct-2-en-3-yl]thiobutanoic acid or a salt or ester thereof.

16. A compound claimed in claim 1, namely, 4-[1-ethynyl-6-[5-(2-furyl)-3-hydroxy-1-pentenyl]-7-hydroxy-2-azabicyclo[3.3.0]oct-2-en-3-yl]thiobutanoic acid or a salt or ester thereof.

17. A compound claimed in claim 2, wherein the lower alkynyl or $R_2$ is ethynyl, 1-propynyl, 1,3-butadiynyl, or phenylethynyl.

18. A compound claimed in claim 3, wherein the lower alkynyl or $R_2$ is ethynyl, 1-propynyl, 1,3-butadiynyl, or phenylethynyl.

19. A compound claimed in claim 4, wherein the lower alkynyl or $R_2$ is ethynyl, 1-propynyl, 1,3-butadiynyl, or phenylethynyl.

20. A compound claimed in claim 1 in which the alkynyl is selected from the group consisting of ethynyl, 1-propynyl, 2-propynyl, 1-butynyl, 2-butynyl, 1-methyl-3-butynyl, 1,1-dimethyl-3-butynyl, 1,3-butadinyl, 1-pentynyl, 2-pentynyl, 3-pentynyl, 4-pentynyl, 1-methyl-3-pentynyl, 1,1-dimethyl-3-pentynyl, 1-hexynyl, 3-hexynyl, 1-methyl-3-hexynyl and 1,1-dimethylhexynyl.

* * * * *